United States Patent
Batchelor et al.

(10) Patent No.: US 11,672,588 B2
(45) Date of Patent: Jun. 13, 2023

(54) PHASE ANGLE MEASUREMENT TECHNIQUES IN ELECTROSURGICAL SYSTEMS

(71) Applicant: GYRUS ACMI, INC., Westborough, MA (US)

(72) Inventors: Kester Julian Batchelor, Mound, MN (US); Wayne Williams, Penarth (GB)

(73) Assignee: Gyrus ACMI, Inc., Westborough, MA (US)

( * ) Notice: Subject to any disclaimer, the term of this patent is extended or adjusted under 35 U.S.C. 154(b) by 427 days.

(21) Appl. No.: 16/874,466

(22) Filed: May 14, 2020

(65) Prior Publication Data

US 2020/0352631 A1 Nov. 12, 2020

Related U.S. Application Data

(63) Continuation of application No. PCT/US2020/031857, filed on May 7, 2020.
(Continued)

(51) Int. Cl.
*A61B 18/12* (2006.01)
*A61B 18/14* (2006.01)
(Continued)

(52) U.S. Cl.
CPC .......... *A61B 18/1206* (2013.01); *A61B 18/00* (2013.01); *A61B 18/1233* (2013.01);
(Continued)

(58) Field of Classification Search
CPC ............ A61B 18/1206; A61B 18/1233; A61B 18/1442; A61B 18/1445;
(Continued)

(56) References Cited

U.S. PATENT DOCUMENTS

| 5,540,684 A | 7/1996 | Hassler, Jr. |
| 5,558,671 A | 9/1996 | Yates |

(Continued)

FOREIGN PATENT DOCUMENTS

| CN | 113811255 A | 12/2021 |
| EP | 1428480 A1 | 6/2004 |

(Continued)

OTHER PUBLICATIONS

"U.S. Appl. No. 16/874,042, Preliminary Amendment filed Oct. 14, 2021", 7 pgs.

(Continued)

*Primary Examiner* — Michael F Peffley
(74) *Attorney, Agent, or Firm* — Schwegman Lundberg & Woessner, P.A.

(57) ABSTRACT

Apparatus and associated methods relate to controlling electrical power of an electrotherapeutic signal that is provided to a biological tissue engaged by an electrosurgical instrument during a medical procedure. Electrical power—a product of a voltage difference across and an electrical current conducted by the engaged biological tissue—is controlled according to a therapeutic schedule. The electrotherapeutic schedule can be reduced or terminated in response to a termination criterion being met. In some examples, the termination criterion is a current characteristic, such as, for example, a decrease in current conducted by the engaged biological tissue. In some examples, the termination criterion is a biological tissue resistance characteristic, such as, for example, an increase in the biological tissue resistance that exceeds a predetermined delta resistance value.

17 Claims, 27 Drawing Sheets

Related U.S. Application Data

(60) Provisional application No. 62/905,345, filed on Sep. 24, 2019, provisional application No. 62/905,337, filed on Sep. 24, 2019, provisional application No. 62/905,366, filed on Sep. 24, 2019, provisional application No. 62/905,318, filed on Sep. 24, 2019, provisional application No. 62/905,360, filed on Sep. 24, 2019, provisional application No. 62/845,647, filed on May 9, 2019.

(51) Int. Cl.
    *A61B 18/00*      (2006.01)
    *A61B 17/00*      (2006.01)

(52) U.S. Cl.
CPC .......... *A61B 18/14* (2013.01); *A61B 18/1442* (2013.01); *A61B 18/1445* (2013.01); *A61B 2017/00017* (2013.01); *A61B 2017/00115* (2013.01); *A61B 2017/00132* (2013.01); *A61B 2017/00154* (2013.01); *A61B 2017/00194* (2013.01); *A61B 2018/0063* (2013.01); *A61B 2018/0072* (2013.01); *A61B 2018/0075* (2013.01); *A61B 2018/00589* (2013.01); *A61B 2018/00595* (2013.01); *A61B 2018/00642* (2013.01); *A61B 2018/00648* (2013.01); *A61B 2018/00654* (2013.01); *A61B 2018/00666* (2013.01); *A61B 2018/00678* (2013.01); *A61B 2018/00684* (2013.01); *A61B 2018/00702* (2013.01); *A61B 2018/00708* (2013.01); *A61B 2018/00714* (2013.01); *A61B 2018/00755* (2013.01); *A61B 2018/00761* (2013.01); *A61B 2018/00767* (2013.01); *A61B 2018/00779* (2013.01); *A61B 2018/00791* (2013.01); *A61B 2018/00827* (2013.01); *A61B 2018/00875* (2013.01); *A61B 2018/00886* (2013.01); *A61B 2018/00898* (2013.01); *A61B 2018/00928* (2013.01); *A61B 2018/00994* (2013.01); *A61B 2018/1455* (2013.01); *A61B 2018/1467* (2013.01)

(58) Field of Classification Search
CPC ........... A61B 2018/00589; A61B 2018/00595; A61B 2018/0063; A61B 2018/00643; A61B 2018/00648; A61B 2018/00654; A61B 2018/00666; A61B 2018/00678; A61B 2018/00684; A61B 2018/00702; A61B 2018/0708; A61B 2018/00779; A61B 2018/0791; A61B 2018/00827; A61B 2018/00869; A61B 2018/00928; A61B 2018/00994; A61B 2018/1455
See application file for complete search history.

(56) References Cited

U.S. PATENT DOCUMENTS

| | | | |
|---|---|---|---|
| 5,769,849 A | 6/1998 | Eggers | |
| 6,398,779 B1 | 6/2002 | Buysse et al. | |
| 6,402,742 B1 | 6/2002 | Blewett et al. | |
| 6,423,057 B1 * | 7/2002 | He | A61B 18/1206 606/49 |
| 6,468,271 B1 * | 10/2002 | Wentzel | A61B 18/1492 606/41 |
| 6,648,883 B2 | 11/2003 | Francischelli et al. | |
| 6,740,079 B1 | 5/2004 | Eggers et al. | |
| 6,790,206 B2 | 9/2004 | Panescu | |
| 6,796,981 B2 | 9/2004 | Wham et al. | |
| 6,830,569 B2 | 12/2004 | Thompson et al. | |
| 6,855,141 B2 | 2/2005 | Lovewell | |
| 6,942,660 B2 | 9/2005 | Pantera et al. | |
| 6,948,503 B2 | 9/2005 | Refior et al. | |
| 6,958,064 B2 | 10/2005 | Rioux et al. | |
| 6,962,587 B2 | 11/2005 | Johnson et al. | |
| 7,037,306 B2 | 5/2006 | Podany et al. | |
| 7,041,096 B2 * | 5/2006 | Malis | A61B 18/1206 606/34 |
| 7,074,218 B2 | 7/2006 | Washington et al. | |
| 7,282,049 B2 * | 10/2007 | Orszulak | A61B 18/1206 606/42 |
| 7,364,577 B2 | 4/2008 | Wham et al. | |
| 7,566,332 B2 | 7/2009 | Jarrard et al. | |
| 7,582,084 B2 | 9/2009 | Swanson et al. | |
| 7,601,149 B2 | 10/2009 | Dicarlo et al. | |
| 7,680,543 B2 | 3/2010 | Azure | |
| 7,722,601 B2 | 5/2010 | Wham et al. | |
| 7,824,399 B2 | 11/2010 | Francischelli et al. | |
| 7,901,400 B2 | 3/2011 | Wham et al. | |
| 7,942,874 B2 | 5/2011 | Eder et al. | |
| 7,972,328 B2 | 7/2011 | Wham et al. | |
| 7,972,334 B2 | 7/2011 | Mcgreevy et al. | |
| 8,105,323 B2 | 1/2012 | Buysse et al. | |
| 8,147,485 B2 | 4/2012 | Wham et al. | |
| 8,152,800 B2 | 4/2012 | Behnke | |
| 8,152,801 B2 | 4/2012 | Goldberg et al. | |
| 8,162,932 B2 | 4/2012 | Podhajsky et al. | |
| 8,167,875 B2 | 5/2012 | Podhajsky et al. | |
| 8,187,263 B2 | 5/2012 | Behnke et al. | |
| 8,211,100 B2 | 7/2012 | Podhajsky et al. | |
| 8,216,223 B2 | 7/2012 | Wham et al. | |
| 8,231,616 B2 | 7/2012 | Mcpherson et al. | |
| 8,241,275 B2 | 8/2012 | Hong et al. | |
| 8,257,350 B2 | 9/2012 | Marion | |
| 8,287,528 B2 | 10/2012 | Wham et al. | |
| 8,290,578 B2 * | 10/2012 | Schneider | A61B 5/053 606/41 |
| 8,317,783 B2 * | 11/2012 | Cao | A61B 18/1206 606/34 |
| 8,333,759 B2 | 12/2012 | Podhajsky | |
| 8,382,751 B2 | 2/2013 | Gilbert et al. | |
| 8,394,092 B2 | 3/2013 | Brannan | |
| 8,419,727 B2 | 4/2013 | Koss et al. | |
| 8,485,993 B2 | 7/2013 | Orszulak et al. | |
| 8,500,727 B2 | 8/2013 | Aramayo | |
| 8,556,891 B2 | 10/2013 | Mathur | |
| 8,556,892 B2 | 10/2013 | Stewart et al. | |
| 8,591,506 B2 | 11/2013 | Wham et al. | |
| 8,617,154 B2 | 12/2013 | Johnston | |
| 8,647,340 B2 | 2/2014 | Blaha | |
| 8,663,214 B2 | 3/2014 | Weinberg et al. | |
| 8,685,016 B2 | 4/2014 | Wham et al. | |
| 8,702,690 B2 | 4/2014 | Paul et al. | |
| 8,728,139 B2 | 5/2014 | Azure et al. | |
| 8,771,269 B2 | 7/2014 | Sherman et al. | |
| 8,795,270 B2 | 8/2014 | Drake | |
| 8,827,992 B2 | 9/2014 | Koss et al. | |
| 8,852,179 B2 | 10/2014 | Ward et al. | |
| 8,858,471 B2 | 10/2014 | Barthe | |
| 8,915,911 B2 | 12/2014 | Azure | |
| 8,920,421 B2 | 12/2014 | Rupp | |
| 8,926,605 B2 | 1/2015 | Mccarthy et al. | |
| 8,961,506 B2 | 2/2015 | Mccarthy et al. | |
| 8,968,297 B2 | 3/2015 | Collins | |
| 8,986,296 B2 | 3/2015 | Peyman | |
| 9,011,337 B2 | 4/2015 | Slayton et al. | |
| 9,011,424 B2 | 4/2015 | Werner | |
| 9,014,814 B2 | 4/2015 | Mccarthy et al. | |
| 9,017,326 B2 | 4/2015 | Dinardo et al. | |
| 9,028,482 B2 | 5/2015 | Collins | |
| 9,037,447 B2 | 5/2015 | Heckel | |
| 9,044,238 B2 | 6/2015 | Orszulak | |
| 9,055,951 B2 | 6/2015 | Deshpande | |
| 9,072,532 B2 | 7/2015 | Van Der Weide et al. | |
| 9,095,350 B2 * | 8/2015 | Condie | A61B 18/1492 |
| 9,125,658 B2 | 9/2015 | Schall | |
| 9,161,813 B2 | 10/2015 | Benamou | |
| 9,168,083 B2 | 10/2015 | Schall et al. | |
| 9,186,200 B2 | 11/2015 | Unger et al. | |
| 9,204,921 B2 | 12/2015 | Sisken | |

(56) References Cited

U.S. PATENT DOCUMENTS

| | | | |
|---|---|---|---|
| 9,232,974 | B2 | 1/2016 | Dycus et al. |
| 9,277,962 | B2 | 3/2016 | Koss et al. |
| 9,314,291 | B2 | 4/2016 | Schall et al. |
| 9,375,250 | B2 | 6/2016 | Krapohl |
| 9,375,270 | B2 | 6/2016 | Wham et al. |
| 9,375,271 | B2 | 6/2016 | Wham et al. |
| 9,463,067 | B2 | 10/2016 | Wham et al. |
| 9,681,883 | B2 | 6/2017 | Windgassen et al. |
| 10,285,750 | B2 | 5/2019 | Coulson et al. |
| 10,512,499 | B2 | 12/2019 | Mchenry et al. |
| 2003/0130711 | A1 | 7/2003 | Pearson et al. |
| 2004/0167508 | A1 | 8/2004 | Wham et al. |
| 2005/0033278 | A1 | 2/2005 | Mcclurken et al. |
| 2007/0173811 | A1 | 7/2007 | Couture et al. |
| 2008/0114351 | A1 | 5/2008 | Irisawa |
| 2009/0048595 | A1* | 2/2009 | Mihori ............... A61B 18/1206 606/49 |
| 2011/0118736 | A1 | 5/2011 | Harper et al. |
| 2012/0150169 | A1* | 6/2012 | Zielinksi ............ A61B 18/1492 606/34 |
| 2013/0197503 | A1 | 8/2013 | Orszulak |
| 2016/0045248 | A1 | 2/2016 | Unger et al. |
| 2016/0058492 | A1 | 3/2016 | Yates et al. |
| 2017/0000554 | A1 | 1/2017 | Yates et al. |
| 2017/0027633 | A1 | 2/2017 | Wham et al. |
| 2017/0196579 | A1 | 7/2017 | Batchelor et al. |
| 2018/0333185 | A1 | 5/2018 | Asher et al. |
| 2018/0250063 | A1 | 9/2018 | Schall et al. |
| 2018/0280071 | A1 | 10/2018 | Nold et al. |
| 2018/0333189 | A1 | 11/2018 | Asher et al. |
| 2019/0200998 | A1 | 7/2019 | Shelton, IV et al. |
| 2019/0201044 | A1 | 7/2019 | Shelton, IV et al. |
| 2020/0046402 | A1 | 2/2020 | Houser |
| 2020/0352618 | A1 | 11/2020 | Batchelor |
| 2020/0352624 | A1 | 11/2020 | Batchelor et al. |
| 2020/0352625 | A1 | 11/2020 | Batchelor et al. |
| 2020/0352626 | A1 | 11/2020 | Batchelor et al. |
| 2020/0352627 | A1 | 11/2020 | Batchelor et al. |
| 2020/0352628 | A1 | 11/2020 | Batchelor et al. |
| 2020/0352629 | A1 | 11/2020 | Batchelor et al. |
| 2020/0352630 | A1 | 11/2020 | Batchelor et al. |
| 2020/0352632 | A1 | 11/2020 | Batchelor et al. |
| 2020/0352635 | A1 | 11/2020 | Batchelor et al. |
| 2020/0352636 | A1 | 11/2020 | Batchelor et al. |
| 2020/0352637 | A1 | 11/2020 | Batchelor |
| 2020/0352638 | A1 | 11/2020 | Batchelor et al. |
| 2020/0352639 | A1 | 11/2020 | Batchelor et al. |

FOREIGN PATENT DOCUMENTS

| | | | |
|---|---|---|---|
| EP | 1472984 | A1 | 11/2004 |
| EP | 1647234 | A1 | 4/2006 |
| EP | 1707144 | A1 | 10/2006 |
| EP | 1715810 | A1 | 11/2006 |
| EP | 1776929 | A1 | 4/2007 |
| EP | 1810632 | A1 | 7/2007 |
| EP | 1810634 | A1 | 7/2007 |
| EP | 1820460 | A2 | 8/2007 |
| EP | 1849425 | A1 | 10/2007 |
| EP | 1862137 | A1 | 12/2007 |
| EP | 1886636 | A1 | 2/2008 |
| EP | 1913889 | A1 | 4/2008 |
| EP | 1943973 | A1 | 7/2008 |
| EP | 1990019 | A2 | 11/2008 |
| EP | 2001385 | A2 | 12/2008 |
| EP | 2033588 | A1 | 3/2009 |
| EP | 2042116 | A1 | 4/2009 |
| EP | 2239009 | A1 | 10/2010 |
| EP | 2249735 | A1 | 11/2010 |
| EP | 2252227 | A1 | 11/2010 |
| EP | 2296572 | A1 | 3/2011 |
| EP | 2307098 | A1 | 4/2011 |
| EP | 2341835 | A1 | 7/2011 |
| EP | 2353534 | A1 | 8/2011 |
| EP | 2417926 | A1 | 2/2012 |
| EP | 2485670 | A2 | 8/2012 |
| EP | 2486884 | A1 | 8/2012 |
| EP | 2510895 | A1 | 10/2012 |
| EP | 2537479 | A1 | 12/2012 |
| EP | 2620113 | A1 | 7/2013 |
| EP | 2709549 | A1 | 3/2014 |
| EP | 2206472 | B1 | 7/2014 |
| EP | 2777578 | A1 | 9/2014 |
| EP | 2853217 | A1 | 4/2015 |
| JP | 2022531724 | A | 7/2022 |
| WO | WO-2020227519 | A1 | 11/2020 |

OTHER PUBLICATIONS

"Dominican Republic Application Serial No. P2021-0231, Office Action dated Nov. 15, 2021", with machine translation, 2 pgs.

"International Application Serial No. PCT/US2020/031857, International Preliminary Report on Patentability dated Nov. 18, 2021", 19 pgs.

"Japanese Application Serial No. 2021-566238, Voluntary Amendment Filed Feb. 3, 2022", w/English claims, 14 pgs.

"U.S. Appl. No. 16/874,293, Restriction Requirement dated Apr. 1, 2022", 9 pgs.

"U.S. Appl. No. 16/874,393, Non Final Office Action dated Apr. 8, 2022", 10 pgs.

"U.S. Appl. No. 16/874,185, Non Final Office Action dated May 9, 2022", 6 pgs.

"U.S. Appl. No. 16/874,145, Non Final Office Action dated May 10, 2022", 12 pgs.

"Singaporean Application Serial No. 11202111518W. Response filed Apr. 27, 2022 to Order Letter mailed Oct. 14, 2021", 26 ogs.

"U.S. Appl. No. 16/874,293, Response filed Jun. 1, 2022 to Restriction Requirement dated Apr. 1, 2022", 9 pgs.

"U.S. Appl. No. 16/874,393, Response filed Jun. 13, 2022 to Non Final Office Action dated Apr. 8, 2022", 11 pgs.

"U.S. Appl. No. 16/874,376, Non Final Office Action dated Jun. 27, 2022", 13 pgs.

"U.S. Appl. No. 16/874,318, Non Final Office Action dated Jul. 15, 2022", 10 pgs.

"International Application Serial No. PCT/US2020/031857, International Search Report dated Oct. 20, 2020", 14 pgs.

"International Application Serial No. PCT/US2020/031857, Invitation to Pay Additional Fees dated Aug. 28, 2020", 25 pgs.

"International Application Serial No. PCT/US2020/031857, Written Opinion dated Oct. 20, 2020", 17 pgs.

"U.S. Appl. No. 16/874,145, Final Office Action dated Sep. 26, 2022", 11 pgs.

"U.S. Appl. No. 16/874,145, Response filed Aug. 9, 2022 to Non Final Office Action dated May 10, 2022", 9 pgs.

"U.S. Appl. No. 16/874,185, Response filed Aug. 9, 2022 to Non Final Office Action dated May 9, 2022", 9 pgs.

"U.S. Appl. No. 16/874,393, Non Final Office Action dated Sep. 14, 2022", 14 pgs.

* cited by examiner

PHASE ANGLE MEASUREMENT TECHNIQUES IN ELECTROSURGICAL SYSTEMS

CLAIM OF PRIORITY

This application is a Continuation of International Patent Application Serial No. PCT/US2020/031857, titled "ELECTROSURGICAL SYSTEMS AND METHODS" to Kester J. Batchelor et al. and filed on May 7, 2020, which is related to (1) U.S. Provisional Application No. 62/845,647, titled "ELECTROSURGICALLY SEALING BIOLOGICAL TISSUE BY CONTROLLING POWER PROVIDED THERETO" to Kester J. Batchelor et al. and filed on May 9, 2019, and to (2) U.S. Provisional Application No. 62/905,318 titled "ELECTROSURGICALLY SEALING BIOLOGICAL TISSUE BY CONTROLLING POWER PROVIDED THERETO" to Kester J. Batchelor et al. and filed on Sep. 24, 2019, and to (3) U.S. Provisional Application No. 62/905,366 titled "CORRECTING TISSUE RESISTANCE MEASUREMENTS USING TEMPORAL DATA" to Huisun Wang et al. and filed on Sep. 24, 2019, and to (4) U.S. Provisional Application No. 62/905,337 titled "PREDICTIVE PHASE CONTROL OF AN ELECTROTHERAPEUTIC PROCEDURE" to Huisun Wang et al. and filed on Sep. 24, 2019, and to (5) U.S. Provisional Application No. 62/905,345 titled "PULSED ELECTRICAL POWER PROVIDED TO SEALED TISSUE TO REDUCE TISSUE STICKING" to Huisun Wang et al. and filed on Sep. 24, 2019, and to (6) U.S. Provisional Application No. 62/905,360 titled "IMPEDANCE PHASE DETECTION FOR SHORT CIRCUIT PREDICTION" to Wayne Williams et al. and filed on Sep. 24, 2019, the entire content of each being incorporated herein by reference in its entirety, and the benefit of priority of each is claimed herein.

BACKGROUND

Electrosurgery is the application of an electrical signal—an electrotherapeutic signal—to produce a change in biological tissue of a surgical patient in some manner. Various electrosurgical techniques are used to cut, coagulate, desiccate, or fulgurate the biological tissue. These electrosurgical techniques and others can be performed during various medical procedures, such as, for example, laparoscopic surgeries. These medical procedures include: appendectomy, cholecystectomy, colectomy, cystectomy, gastric banding, gastric bypass, hernia repair, nephrectomy, Nissen fundoplication, prostatectomy, sleeve gastrectomy, and others. Each of these medical procedures can have one or more electrotherapeutic phases, such as, for example, interrogation phase, heating phase, drying phase, cauterizing phase, etc.

The electrotherapeutic signals used in such medical procedures can be generated by an electrosurgical generator and then provided to the biological tissue via an electrosurgical instrument, which can be electrically connected to the electrosurgical generator. The electrosurgical instrument can be configured to mechanically and electrically engage the biological tissue to which the electrotherapeutic signal is provided. Various types of such electrosurgical instruments can be employed, including, for example, various types of forceps, conductive spatulas, electrical pads, etc.

Different medical procedures can implement different electrotherapeutic signals so as to achieve results specific to these different medical procedures. Various electrical metrics of the electrotherapeutic signals provided to the engaged biological tissue can be used to characterize these electrotherapeutic signals. These electrical metrics include: polarity (monopolar, bipolar), AC and/or DC, frequency, signal amplitude, attack and decay profiles, etc. Electrosurgical generators that generate these various electrotherapeutic signals can control one or more of these electrical metrics so as to provide electrotherapeutic signals that yield efficacious results in the biological tissue engaged by the electrosurgical instrument.

SUMMARY

Apparatus and associated methods relate to a system for providing controlled electrical power to biological tissue. The electrosurgical system includes a forceps having opposable jaw members configured to open and close. The forceps also has a handpiece having a gripping lever configured to cause the opposable jaw members to open and close. The opposable jaw members, when closed, are configured to clamp the biological tissue therebetween in a manner that provides electrical communication between the opposable jaw members via the clamped biological tissue. The electrosurgical system also includes an electrosurgical generator electrically couplable to the forceps. The electrosurgical generator includes an electrical-energy source in electrical communication with the opposable jaw members when the electrosurgical generator is electrically coupled to the forceps. The electrical-energy source is configured to generate electrotherapeutic signals. The electrosurgical generator includes a control circuit configured to cause the electrical-energy source to provide an electrotherapeutic signal to the clamped biological tissue during an electrotherapeutic phase. Electrical power of the provided electrotherapeutic signal is controlled according to an electrotherapeutic schedule.

Some examples relate to an electrosurgical generator for providing controlled electrical power to biological tissue engaged by an electrosurgical instrument. The electrosurgical generator includes an electrical connector configured to electrically couple the electrosurgical instrument to the electrosurgical generator so as to provide electrical communication between the electrosurgical generator and the engaged biological tissue. The electrosurgical generator includes an electrical-energy source electrically coupled to the electrical connector and configured to generate an electrotherapeutic signal. The electrosurgical generator also includes a control circuit configured to cause the electrical-energy source to provide the electrotherapeutic signal to the engaged biological tissue during an electrotherapeutic phase. Electrical power of the electrotherapeutic signal is provided to the engaged biological tissue controlled according to an electrotherapeutic schedule.

Some examples relate to a method for providing controlled electrical power to biological tissue engaged by an electrosurgical instrument. The method includes the step of engaging, via the electrosurgical instrument, the biological tissue in a manner that provides electrical communication between the electrosurgical instrument and the engaged biological tissue. The method proceeds to the step of providing, via an electrical-energy source in electrical communication with the electrosurgical instrument, an electrotherapeutic signal to the engaged biological tissue during an electrotherapeutic phase. The method also includes the step of controlling electrical power of the provided electrotherapeutic signal according to an electrotherapeutic schedule.

DETAILED DESCRIPTION

Figure 1:
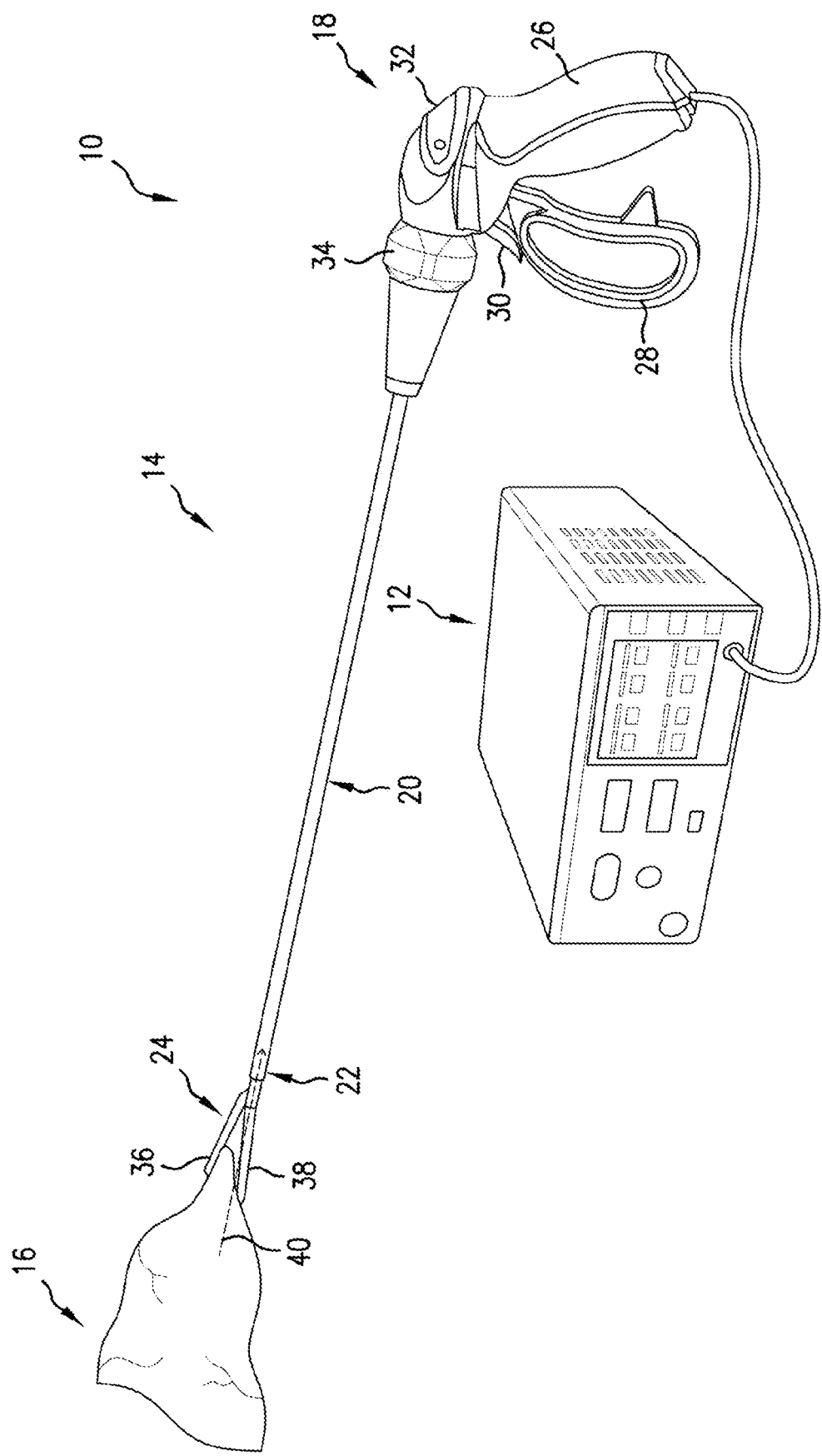
FIG. 1 is a perspective view of an electrosurgical system providing electrotherapy to biological tissue of a surgical patient.

Apparatus and associated methods relate to application of electrotherapeutic signals to biological tissues engaged by an electrosurgical instrument. Control of various electrical metrics of these electrotherapeutic signals will be disclosed below as will the specific electrosurgical techniques that perform such control. This specification is organized into sections titled: i) Electrical Power Control of Electrotherapeutic Signals (FIGS. 1-4); ii) Predictive Phase Control of an Electrotherapeutic Signal (FIGS. 5-6); iii) Correction of Measured Electrical Resistance of Engaged Biological Tissue (FIGS. 7A-7B and 9); iv) Modification of Initial Impedance (FIG. 9); v) Reducing Sticking of Biological Tissue to Electrosurgical Instrument by Pulsing Electrical Power of Electrotherapeutic Signal (FIGS. 10A-10D and 11); vi) Determining Presence or Absence of a Conductive Foreign Body in Biological Tissue Engaged by an Electrosurgical Instrument (FIGS. 12 and 13); vii) Short Circuit Error Trapping with Band Between Trigger and Escape Values (FIG. 14); viii) Open Circuit Check for Impedance Limit Endpoint Waveform (FIGS. 15 and 16); ix) Alternate Power Correction Outputs in Low Accuracy Hardware Systems (FIG. 17); x) Reduced Thermal Margin Combination Energy Device (FIGS. 18 and 19); xi) Staged Impedance Values to Control Thermal Margins in Systems with Slow CPUs (FIGS. 20 and 21); xii) Consumed Energy Monitoring and Open Circuit Evaluation (FIGS. 22A-22D); xiii) Dwell Time Between Pulses; and xiv) Incremental Adjustment of Control Parameter as a Function of a Monitored Variable. The techniques are described in these separate sections for purposes of explanation only. Unless stated explicitly to the contrary, each of these techniques can be used in combination with one or more of the other techniques described in this disclosure.

Electrical Power Control of Electrotherapeutic Signals (FIGS. 1-4)

Electrosurgically sealing or coagulating biological tissue engaged by an electrosurgical instrument is an electrosurgical technique used in various medical procedures. The engaged biological tissue can be electrosurgically sealed by heating the engaged biological tissue in a controlled manner. In some medical procedures, the biological tissue that is being sealed is a vessel. Heating of the vessel causes the collagen found in the vessel walls to become denatured. This denatured collagen forms a gel-like substance acting as glue between the vessel walls. When forced together and maintained together while cooling, opposite walls of a vessel will then form a seal.

Heating of the vessel is carefully controlled so that neither too little nor too much energy is provided to the vessel. If too much energy is provided thereto, then charring and/or burning of the vessel wall can occur. If too little energy is provided thereto, then seal quality of the vessel can be poor. One measure of seal quality is a pressure difference that the sealed vessel can withstand without bursting. Low quality seals can be compromised when the pressure applied thereto exceeds some value.

The rate at which the energy is provided to the vessel can also be carefully controlled so as to facilitate rapid performance of the electrosurgical procedure. Rapid performance of electrosurgical procedures reduces the time and difficulty of these procedures. The rate of heating, however, should not be so rapid as to cause uncontrolled boiling of fluid within the biological tissue. Uncontrolled boiling can rupture engaged or nearby biological tissues and/or compromise the quality of the seal.

Heating of the engaged biological tissue can be controlled by controlling the electrical power of an electrotherapeutic signal provided to and dissipated by the engaged biological tissue. Such electrical power can be controlled according to a sealing schedule. For example, the sealing schedule can be indicative of a product of a voltage difference across and an electrical current conducted by the engaged biological tissue. Thus, the sealing schedule is an electrical-power schedule. In some examples, the electrotherapeutic signal can be reduced or terminated in response to a termination criterion being met. In some examples, the termination criterion is a current characteristic, such as, for example, a decrease in current conducted by the engaged biological tissue. In some examples, the termination criterion is a resistance characteristic, such as, for example, an increase in the electrical resistance of the engaged biological tissue. Such an increase in the electrical resistance in excess of a predetermined delta resistance value can be used as a termination criterion, for example, where the predetermined delta resistance value is the difference between the measured resistance (or impedance) and the lowest value of the resistance (or impedance) measured in the pulse. In some examples, the termination criterion is a temporal condition, such as, for example, a time duration, predetermined or calculated based on some condition.

Electrical impedance is complex and, as such, includes a real component (resistance) and an imaginary component (reactance). This document describes techniques using impedance or resistance. It should be understood that where complex impedance values are available, such values can be used in place of resistance values. Conversely, where no complex impedance values are available, resistance values can be used instead unless otherwise stated.

In addition, many of the techniques below describe delivering electrosurgical energy to biological tissue. Unless indicated to the contrary, each of these techniques can deliver the electrosurgical energy using either power-controlled or voltage-controlled techniques. In a power-controlled implementation, a control circuit can control delivery of electrosurgical energy using a product of the voltage applied across the engaged biological tissue and the electrical current, e.g., according to a plan or schedule. For example, the control circuit can control delivery of a constant power or a monotonically increasing power during a particular phase, e.g., drying phase.

This document describes, among other things, one or more techniques for providing electrotherapy, which can be provided according to a treatment or other plan. The plan can include a recipe, prescription, regimen, methodology, or the like. The plan can include one or more temporal aspects, such as a schedule, such as can include occurrence or recurrence (or inhibition or suppression) timing, frequency, type, relative combination (e.g., coagulation relative to cutting) or the like. The plan can include electrotherapy waveform information, such as can include pulse width, duty cycle, on duration, off duration, repetition rate, amplitude, phase, or the like. The plan need not be static or a priori in nature, but can include one or more dynamic aspects, such as can be modified or governed, such as by diagnostic, operational, or other information obtained during or between electrotherapy delivery instances, including in a closed-loop, or other feedback manner. One or more aspects of the plan can be tailored, such as to the specific patient, to a sub-population of patients such as who share one or more specified characteristics, or a population of patients, such as can be based on stored patient data, or by user input such as which may be provided by the patient or by a caregiver. The plan can include one or more conditional aspects, such as can include one or more branch conditions, such as can be determined using a patient characteristic, a diagnostic measure, an efficacy determination, or an operational characteristic of the device or its environment. Such branch conditions may be determined automatically, by the device, e.g., without requiring user input, or may involve user input, such as can be provided before, during, or after one or more portions of operations of the electrotherapy device according to the plan. The plan can involve communicating with or using another device, such as to receive or provide one or any combination of inputs, outputs, or instructions, operating parameters, or measured data. One or more aspects of the plan can be recorded or encoded onto a medium, such as a computer or other machine-readable medium, such as can be a tangible medium.

In a voltage-controlled implementation, the control circuit can control the voltage of the electrosurgical energy delivered, e.g., according to a plan, regimen, or schedule. For example, the control circuit can control delivery of a constant voltage or a monotonically increasing voltage during a particular phase, e.g., drying phase.

FIG. 1 is a perspective view of an electrosurgical system providing electrotherapy to biological tissue of a surgical patient. In FIG. 1, electrosurgical system 10 includes electrosurgical generator 12 and forceps 14, which is shown engaging biological tissue 16. Electrosurgical generator 12 is generating an electrotherapeutic signal which is provided to engaged biological tissue 16 via forceps 14. Although FIG. 1 depicts forceps 14 engaging and delivering the electrotherapeutic signal to biological tissue 14, various types of electrosurgical instruments, such as those disclosed above, can be used for such purposes.

Various types of forceps as well can be used for delivering the electrotherapeutic signal to biological tissue 14. For example, forceps 14 can be medical forceps, cutting forceps, or an electrosurgical forceps (e.g., monopolar or bipolar forceps). Forceps 14, in some examples, can be used for medically related procedures, such as open and/or laparoscopic medical procedures to manipulate, engage, grasp, cut, cauterize, seal, or otherwise affect a vessel, biological tissue, vein, artery, or other anatomical feature or object.

As illustrated in FIG. 1, forceps 14 includes hand piece 18, shaft assembly 20, knife blade assembly 22, and gripping assembly 24. In some examples, such as the illustrated example of FIG. 1, forceps 14 is electrically connected to electrosurgical generator 12, which generates the electrotherapeutic signal and provides the generated electrotherapeutic signal to forceps 14. Forceps 14 then electrically communicates the electrotherapeutic signal to gripping assembly 24 and/or to a remote pad, which can be employed for various electrosurgical techniques, such as cauterizing, sealing, or other such electrosurgical techniques.

Hand piece 18 includes handle 26, gripping lever 28, knife trigger 30, electrical therapy actuation button 32, and rotation wheel 34. Gripping assembly 24 includes first jaw member 36 and second jaw member 38. Shaft assembly 20 is connected at a proximal end to hand piece 18, and at a distal end to gripping assembly 24. Shaft assembly 20 extends distally from hand piece 18 in longitudinal direction 40 to gripping assembly 24.

Shaft assembly 20 functions to permit a portion of forceps 14 (e.g., gripping assembly 24 and a distal portion of shaft assembly 20) to be inserted into a patient or other anatomy while a remaining portion of forceps 14 (e.g., hand piece 18 and a remaining proximal portion of shaft assembly 20) are outside of the patient or other anatomy. Though illustrated in FIG. 1 as substantially straight, in other examples, shaft assembly 20 can include one or more angles, bends, and/or arcs. Shaft assembly 20 can be a cylinder with a circular, elliptical, or other cross-sectional profile, or other elongated member that extends from hand piece 18 to gripping assembly 24. In some examples, the shaft can be bendable, steerable or otherwise deflectable.

In some examples, such as the example of FIG. 1, shaft assembly 20 can include an elongated hollow member (e.g., a tubular outer shaft) that encloses knife blade assembly 22 and mechanical linkage to couple knife blade assembly 22 with knife trigger 30. In general, shaft assembly can be any elongated member having stiffness sufficient to transfer forces along longitudinal direction 40. Shaft assembly 20 also can include conductive elements (e.g., wires, a conductive outer shaft and/or a conductive inner shaft, etc.) to provide electrical communication between hand piece 18 and gripping assembly 24, so as to communicate an electrotherapeutic signal thereby.

Gripping lever 28, knife trigger 30, electrical therapy actuation button 32, and rotation wheel 34 of hand piece 18, each are configured to cause various actuations, usually at the distal end, of shaft assembly 20. For example, actuation of gripping lever 28 is configured to control operation of gripping assembly 24 at the distal end of shaft assembly 20. Gripping lever 28 is a gripping actuator that is movable between an open configuration position (illustrated in FIG. 1) and a closed configuration position in which gripping lever 28 is moved proximally toward handle 26. Movement of gripping lever 28 proximally toward handle 26 to the closed configuration position causes gripping assembly 24 to transition from the open configuration to the closed configuration. Movement of gripping lever 28 distally (e.g., release of gripping lever 28 to the open configuration position causes gripping assembly 24 to transition from the closed configuration to the open configuration.

Such transitions between the open and closed configurations of gripping assembly 24 are realized by one or more of first and second jaw members 36 and 38 moving between an open configuration (illustrated in FIG. 1), in which first and second jaw members 36 and 38 are spaced apart, and a closed configuration, in which the gap between first and second jaw members 36 and 38 is reduced or eliminated. Various electrosurgical instruments engage biological tissue 16 in various manners. In some electrosurgical instruments, such as the one illustrated in FIG. 1, first and second jaw members 36 and 38 are opposable to one another. In the depicted example first and second jaw members 36 and 38 are configured to clamp biological tissue 16 therebetween in a manner that provides electrical communication between opposable jaw members 36 and 38 via clamped biological tissue 16. Other electrosurgical instruments can engage biological tissue in other manners.

Mechanical linkage within shaft assembly 20 can be configured to cause one or more of first and second jaw members 36 and 38 to move between the open configuration and the closed configuration in response to actuation of gripping lever 28. One example mechanism for causing movement of a gripping assembly between the open and closed configurations can be found in U. S. Patent Publication No. 2017/0196579, entitled "FORCEPS JAW MECHA-NISM" and filed on Jan. 10, 2017 to Batchelor et al., the contents of which are hereby incorporated by reference in their entirety.

Actuation of knife trigger 30 is configured to control operation of knife blade assembly 22 located at the distal end of shaft assembly 20. Knife blade assembly 22 is configured to cut, excise, or otherwise affect biological tissue or other object(s) clamped between first and second jaw members 36 and 38. Knife trigger 30 is a knife blade actuator that is movable between a retracted configuration position (illustrated in FIG. 1) and a deployed or extended configuration position in which knife trigger 30 is moved proximally toward handle 26 to cause knife blade assembly 22 to cut biological tissue 16, which is clamped between first and second jaw members 36 and 38. Movement of knife trigger 30 proximally toward handle 26 to the deployed configuration position causes a cutting blade of knife blade assembly 22 to engage biological tissue 16, thereby cutting biological tissue 16. Movement of knife trigger 30 distally (e.g., release of knife trigger 30) causes the knife blade to retract from clamped biological tissue 16. Mechanical linkage, for example, within shaft assembly 20 can be configured to cause the knife blade to engage and retract from engaged biological tissue 16.

Rotation wheel 34 is configured to control rotational configuration of one or more of knife blade assembly 22, and gripping assembly 24 at the distal end of shaft assembly 20 and/or control rotational configuration of shaft assembly 20. Movement (e.g., rotation) of rotation wheel 34 causes rotation of one or more of shaft assembly 20, knife blade assembly 22, and gripping assembly 24 about an axis extending in longitudinal direction 40. Such rotational control can facilitate alignment of gripping assembly and/or knife blade assembly with clamped biological tissue 16.

Therapy actuation button 32 is configured to control generation and/or delivery of the electrotherapeutic signal to engaged biological tissue 16. Actuation of therapy actuation button 32 causes an electrotherapeutic signal, drawn from e.g., electrosurgical generator 12, to be applied to one or more of first and second jaw member 36 and 38, a remote pad (not illustrated), or other portions of forceps 14 to cauterize, seal, or otherwise electrically affect a patient or other anatomy. One example of a hand piece utilizing a gripping lever, knife trigger, rotation wheel, and therapy actuation button can be found in U.S. Pat. No. 9,681,883, entitled "FORCEPS WITH A ROTATION ASSEMBLY" and issued on Jun. 20, 2017 to Windgassen et al., the contents of which are hereby incorporated by reference in their entirety.

Figure 2:
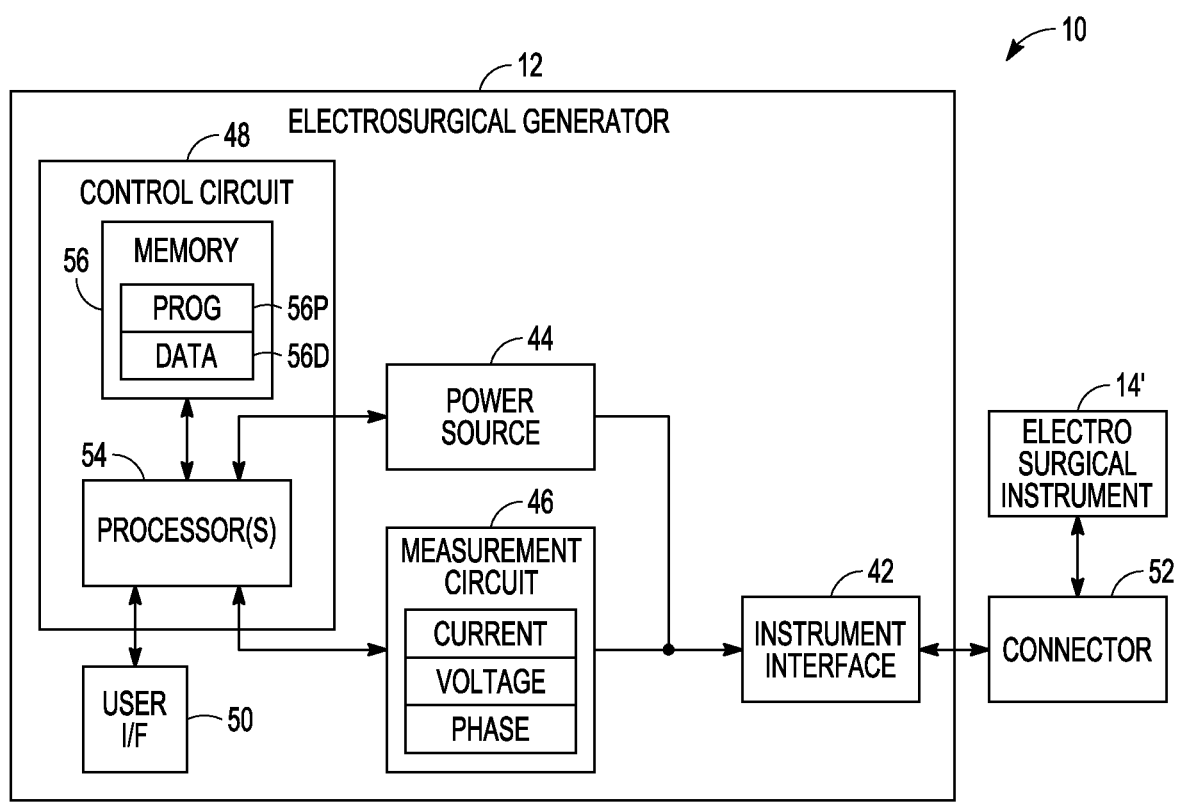
FIG. 2 is a block diagram of an electrosurgical system for sealing biological tissue engaged by an electrosurgical instrument.

FIG. 2 is a block diagram of an electrosurgical system for sealing biological tissue engaged by an electrosurgical instrument. In FIG. 2, electrosurgical system 10 include electrosurgical generator 12 and electrosurgical instrument 14'. Electrosurgical instrument 14' can be any electrosurgical instrument configured to engage and deliver an electrotherapeutic signal to biological tissue. Electrosurgical generator 12 is configured to generate the electrotherapeutic signal, such as a high frequency (AC) electrical signal, that electrosurgical instrument 14' delivers to engaged biological tissue 16.

In some examples, electrosurgical instrument 14' is a forceps having a handpiece coupled to opposable jaw members via a shaft assembly, such as forceps 14 depicted in FIG. 1. In other examples, electrosurgical instrument 14' is a conductive spatula, a conductive pad, or other electrosurgical device. These various types of electrosurgical instruments have various ways of engaging biological tissues (e.g., clamping, touching, surrounding, penetrating, radiating, etc.)

Electrosurgical generator 12 includes instrument interface 42, electrical-energy source 44, measurement circuit 46, control circuit 48, and user interface 50. Instrument interface 42 can include signal drivers, buffers, amplifiers, ESD protection devices, and electrical connector 52, for example. Electrical connector 52 is configured to electrically couple electrosurgical instrument 14' to electrosurgical generator 12 so as to provide electrical communication between electrosurgical generator 12 and electrosurgical instrument 14'. Such electrical communication can be used to transmit operating power and/or electrical signals therebetween. Electrosurgical instrument 14', in turn, can provide electrical communication between electrical connector 52 and biological tissue engaged thereby.

Electrical-energy source 44 is configured to generate an electrotherapeutic signal to be delivered to the engaged biological tissue via electrically connected electrosurgical instrument 14'. The generated electrotherapeutic signal can be controlled so as to obtain the desired result for a specific electrosurgical procedure. In one example, for example, the electrotherapeutic signal is configured to resistively heat the engaged biological tissue so as to surgically affect, such as seal, the engaged biological tissue. Such controlling of the electrotherapeutic signal will be further disclosed below.

Measurement circuit 46 is configured to measure one or more electrical parameters of biological tissue engaged by connected electrosurgical instrument 14'. Measurement circuit 46 is in electrical communication with connected electrosurgical instrument 14' when electrosurgical generator 12 is electrically connected to electrosurgical instrument 14' via electrical connector 52. Various examples of measurement circuit 46 are configured to measure various electrical parameters. For example, measurement circuit 46 can be configured to measure voltage difference delivered across and/or electrical current conducted by the engaged biological tissue. In some examples, measurement circuit 46 can be configured to measure phase angle between voltage difference delivered across and electrical current conducted by the engaged biological tissue. In some examples, measurement circuit 46 is configured to measure DC and or AC electrical parameters of the engaged biological tissue.

Measured parameters, such as voltage difference delivered across and/or electrical current conducted by the engaged biological tissue can be used to determine other electrical metrics. For example, measurements of voltage difference delivered across and/or electrical current conducted by the engaged biological tissue can be used to determine electrical resistance of the engaged biological tissue. Measurements of voltage difference delivered across and electrical current conducted by the engaged biological tissue, as well as the phase angle therebetween can be used to determine complex impedance of the engaged biological tissue. Measurements of voltage difference delivered across and electrical current conducted by the engaged biological tissue, as well as the phase angle therebetween also can be used to determine apparent power (VA) and/or real power (W) provide to the engaged biological tissue.

Such measurements of electrical parameters can be used for controlling an electrotherapeutic signal during delivery to an engaged biological tissue. For example, measurements of the voltage difference delivered across and measurements of the electrical current conducted by the engaged biological tissue can be used to determine and/or control the real power provided to the engaged tissue. This determined real power can then be compared with an electrotherapeutic schedule. Such a comparison could be used to generate an error signal. Measurements of electrical parameters can also be used to determine phase-control criteria for controlling phases of electrotherapy. Phase-control criteria can include criteria for commencement and termination of a phase, as well as criteria for intra-phase control.

Control circuit 48 is configured to control operation of electrical-energy source 44 and/or measurement circuit 46. Control circuit 48 is electrically connected to electrical-energy source 44 and measurement circuit 46. Control circuit 48 causes electrical-energy source to provide an electrotherapeutic signal to biological tissue engaged by electrically connected electrosurgical instrument 14'. Control circuit 48 causes electrical-energy source 44 to generate the electrotherapeutic signal according to an electrotherapeutic schedule such that the generated electrotherapeutic signal is controlled for a specific electrosurgical procedure.

Various electrotherapeutic schedules can be used to effectuate various types of electrotherapy. For example, in some examples, real power (W) of the electrotherapeutic signal provided to the engaged biological tissue is controlled according to an electrical-power schedule. In other examples, voltage difference (V) of the electrotherapeutic signal delivered across the engaged biological tissue is controlled according to a voltage schedule. In other examples, electrical current (A) of the electrotherapeutic signal conducted by the engaged biological tissue is controlled according to an electrical-current schedule. In still other examples, apparent power (VA) of the electrotherapeutic signal provided to the engaged biological tissue can be controlled according to a voltage-amperage schedule.

Control circuit 48, for example, can cause electrical-energy source 44 to provide energy to engaged biological tissue, such that a product of a voltage difference across and an electrical current conducted by the engaged biological tissue is controlled according to the electrotherapeutic schedule. Control circuit 48 can use the comparison of the determined real power with an electrotherapeutic schedule to generate an error signal. Such an error signal can be used in a closed-loop feedback system that includes electrical-energy source 44, so as to generate the electrotherapeutic signal according to the electrotherapeutic schedule.

As illustrated in FIG. 2, control circuit 48 includes processor 54 and memory 56. Control circuit 48 can include a timer and/or a clock. In some examples, the timer and/or the clock are part of processor 54. In other examples, the timer and/or clock are separate from the processor 54. Processor 54, in one example, is configured to implement functionality and/or process instructions for execution within electrosurgical system 10. For instance, processor 54 can be capable of receiving from and/or processing instructions stored in program memory 56P. Processor 54 can then execute program instructions so as to cause electrical-energy source 44 to generate the electrotherapeutic signal according to a predetermined electrotherapeutic schedule. The predetermined electrotherapeutic schedule can be retrieved from data memory 56D, for example. Processor 54 can compare electrical parameters measured by measurement circuit 46 with the retrieved predetermined electrotherapeutic schedule. Processor 54 can send commands to electrical-energy source 44 and/or measurement circuit 46. Processor 54 also can also send or receive information from user interface 50.

In various examples, electrosurgical generator 12 can be realized using the elements illustrated in FIG. 2 or various other elements. For example, processor 54 can include any one or more of a microprocessor, a control circuit, a digital signal processor (DSP), an application specific integrated circuit (ASIC), a field-programmable gate array (FPGA), or other equivalent discrete or integrated logic circuitry.

Memory 56 can be configured to store information within electrosurgical system 10 during operation. Memory 56, in some examples, is described as computer-readable storage media. In some examples, a computer-readable storage media can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, memory 56 is a temporary memory, meaning that a primary purpose of memory 56 is not long-term storage. Memory 56, in some examples, is described as volatile memory, meaning that memory 56 does not maintain stored contents when power to electrosurgical system 10 is turned off. Examples of volatile memories can include random access memories (RAM), dynamic random access memories (DRAM), static random access memories (SRAM), and other forms of volatile memories. In some examples, memory 56 is used to store program instructions for execution by processor 54. Memory 56, in one example, is used by software or applications running on electrosurgical system 10 (e.g., a software program implementing electrical control of an electrotherapeutic signal provide to biological tissue engaged by an electrosurgical instrument) to temporarily store information during program execution, such as, for example, in data memory 56D.

In some examples, memory 56 can also include one or more computer-readable storage media. Memory 56 can be configured to store larger amounts of information than volatile memory. Memory 56 can further be configured for long-term storage of information. In some examples, memory 56 includes non-volatile storage elements. Examples of such non-volatile storage elements can include magnetic hard discs, optical discs, flash memories, or forms of electrically programmable memories (EPROM) or electrically erasable and programmable (EEPROM) memories.

User interface 50 can be used to communicate information between electrosurgical system 10 and a user (e.g., a surgeon or technician). User interface 50 can include a communications module. User interface 50 can include various user input and output devices. For example, User interface can include various displays, audible signal generators, as well switches, buttons, touch screens, mice, keyboards, etc.

User interface 50, in one example, utilizes the communications module to communicate with external devices via one or more networks, such as one or more wireless or wired networks or both. The communications module can include a network interface card, such as an Ethernet card, an optical transceiver, a radio frequency transceiver, or any other type of device that can send and receive information. Other examples of such network interfaces can include Bluetooth, 3G, 4G, and Wi-Fi radio computing devices as well as Universal Serial Bus (USB) devices.

Figure 3A:
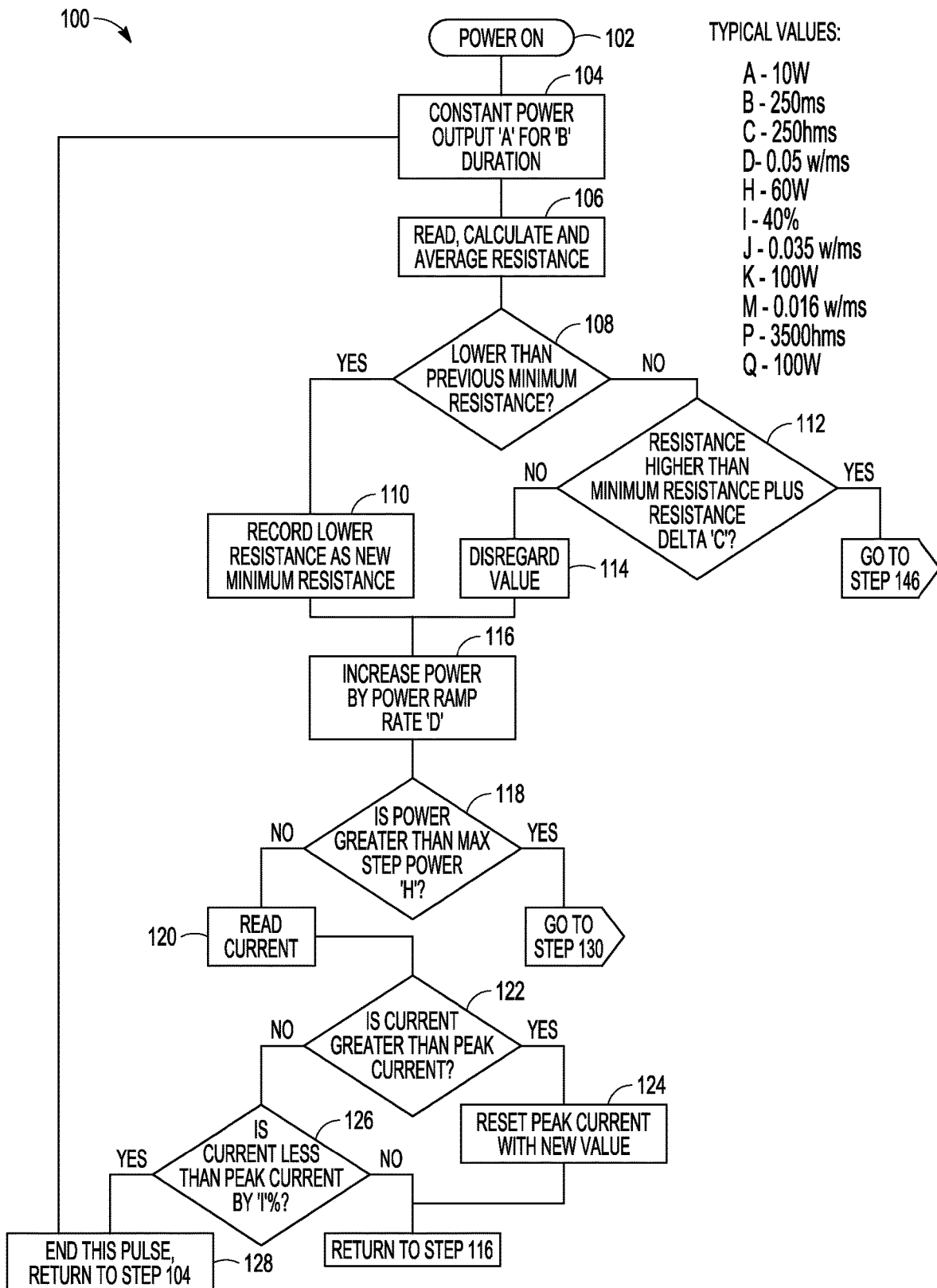
FIGS. 3A-3B are flow charts of a method for sealing a biological tissue engaged by an electrosurgical instrument.
Figure 3B:
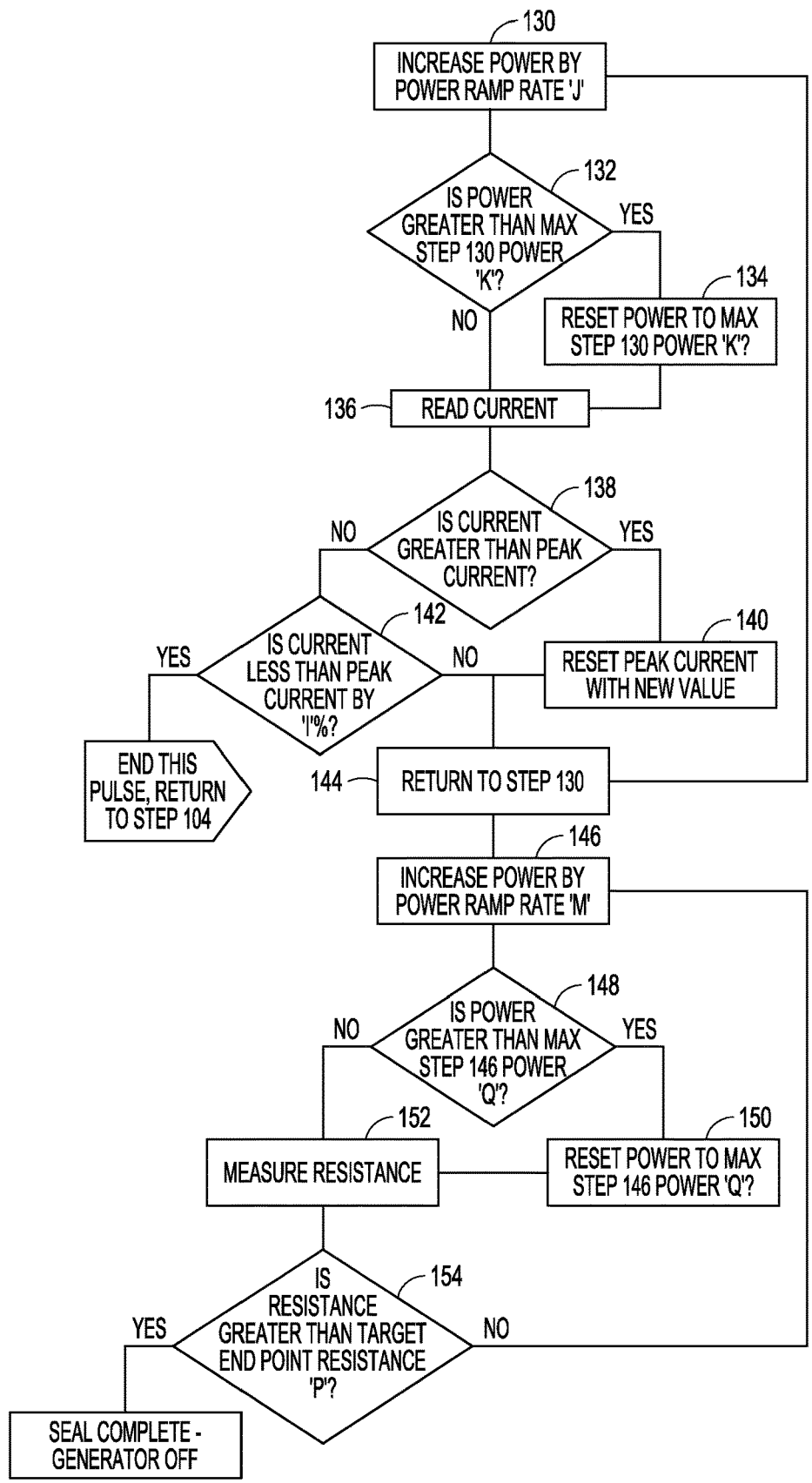

FIGS. 3A-3B are flow diagrams of a non-limiting example of a method for generating an electrotherapeutic signal for sealing a biological tissue engaged by an electrosurgical instrument. Method 100 illustrated in FIGS. 3A-3B can be used with an electrosurgical system such as electrosurgical system 10 depicted in FIGS. 1-2. Using various techniques described below, an electrosurgical generator can control an energy delivery of the therapeutic signal provided to the biological tissue during a portion of a therapeutic phase according to an incremental change in energy delivery as a function of a change in a measured electrical parameter of the biological tissue. In some examples, a control circuit can control the electrical power of the therapeutic signal provided to the biological tissue during a portion of a therapeutic phase according a therapeutic plan, such as by controlling the power during the phase that provides the tissue modification.

For example, a control circuit can incrementally modify the power as a function of current. In some examples, the function of current is a function of a change in current. The change in current can be the change in the current over the course of a pulse and, as such, can look more like a current value. In some examples, the function of current is a function of an instantaneous measured change in current and, as such, can look more like the slope of the current function. The control circuit can modify the power based upon either of these—current or instantaneous change in current. In some examples, the function of the instantaneous measured change in current is a linear function. In other examples, the control circuit can incrementally modify the power as a function of resistance, such as when using a voltage-controlled technique.

Figure 4:
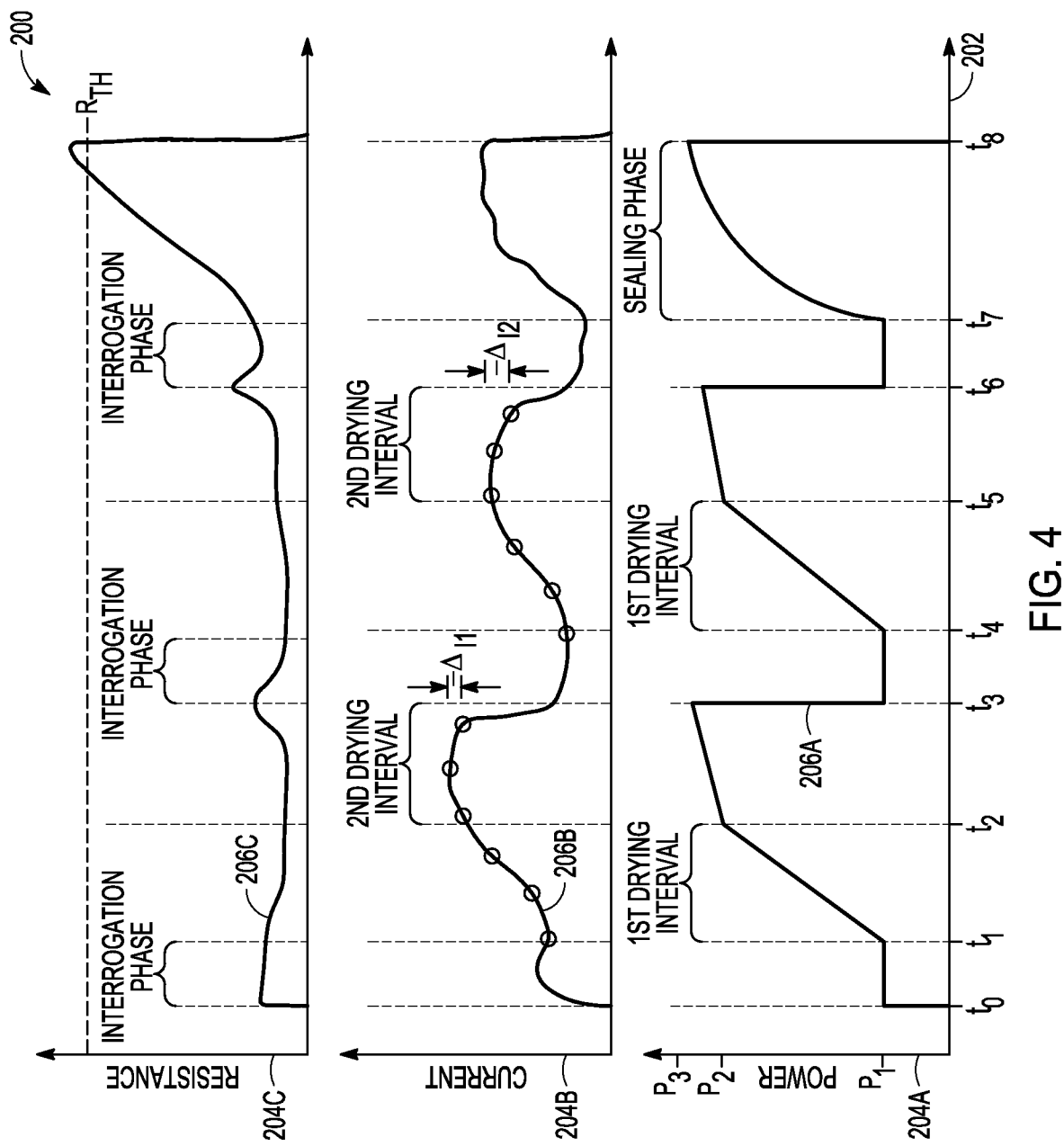
FIG. 4 is a graph depicting examples of an electrical-power schedule used to control electrical power provided to biological tissue being sealed.

As seen in FIG. 4, in some examples, the system can control the electrical power of the therapeutic signal provided to the biological tissue during a portion of the therapeutic phase using a pre-defined power curve. In some examples, the pre-defined power curve can include two or more linear portions.

It should be noted that the FIGS. 3A and 3B and FIG. 4 are non-limiting specific examples used for purposes of explanation.

In some examples, the method can switch from using a power-controlled technique to using a voltage-controlled technique. In a voltage-controlled technique, current can be capped but allowed to move freely according to the responding impedance, which can allow for a variable power delivery. For example, the control circuit can deliver a pulse using power-controlled techniques and as the resistance increases, approaches a boiling condition, or reaches a threshold, the system can switch to a voltage-controlled technique. In this manner, at the beginning the system can take advantage of power-controlled techniques to deliver energy faster, but closer to boiling the system can switch over to voltage-controlled techniques, which can be more responsive. In some implementations that use a voltage-controlled technique, the system can control the electrical power of the therapeutic signal provided to the biological tissue during a portion of the therapeutic phase using a pre-defined voltage curve. In some examples, the pre-defined voltage curve can include two or more linear portions.

In FIG. 3A, method 100 begins at step 102, in which the electrosurgical system 10 (depicted in FIGS. 1-2) is powered on. Then, at step 104, an interrogation phase begins, in which control circuit 48 (depicted in FIG. 2) causes electrical-energy source 44 (depicted in FIG. 2) to provide an interrogation signal, such as an interrogation pulse, to the engaged biological tissue during the interrogation phase. Power (W) of the provided interrogation signal is controlled according to an interrogation schedule. In some examples, the power levels provided to the engaged biological tissue during the interrogation phase can be low so as to cause little or no tissue effect. Such low power levels can be provided for the purpose of obtaining measurements of electrical properties of the engaged biological tissue. Such measurements are sometimes obtained before electrotherapy is provided so as to obtain a pre-electrotherapy measurement. In some examples, the interrogation schedule is indicative of providing constant electrical power during the interrogation phase. Such a schedule can be called a constant power schedule. In some examples, control circuit 48 terminates the interrogation phase after a predetermined time duration.

At step 106, controller 48 causes measurement circuit 46 (depicted in FIG. 2) to measure a first electrical resistance of the engaged biological tissue during an interrogation phase. The first time that step 106 is performed this measured electrical resistance is a reference resistance. Then, at step 108, control circuit 48 compares the measured electrical resistance with a minimum resistance previously measured (if any). If, at step 108, the measured electrical resistance is lower than the minimum resistance, then the method advances to step 110, where the measured electrical resistance is recorded as the new minimum value, and then the method advances to step 116 (where a first interval of the drying or desiccation phase begins). If, however, at step 108, the measured electrical resistance is greater than the minimum resistance, then the method advances to step 112, where control circuit 48 compares the measured electrical resistance with a sum of the minimum resistance and a predetermined resistance delta. If, at step 112, the measured electrical resistance is less than the sum of the minimum resistance and a predetermined resistance delta, then the method advances to step 114, where the measured electrical resistance is disregarded. If, however, at step 112, the measured electrical resistance is greater than the sum of the minimum resistance and a predetermined resistance delta, then the method advances to step 146 illustrated in FIG. 3B.

At step 116, a first interval of the drying or desiccation phase begins, such as where tissue modification occurs, in which control circuit 48 causes electrical-energy source 44 to provide a first drying signal, such as a first drying pulse, to the engaged biological tissue during the first drying interval of the drying phase. Power (W) of the provided first drying signal is controlled according to a first drying schedule or plan, such as using a pre-defined power curve, such as having a linear ramp rate. In some examples, the first drying schedule or plan is a monotonically-increasing power schedule, such as shown in the bottom graph in FIG. 4 between times $t_1$ and $t_2$.

Then, at step 118, control circuit 48 compares the provided power to a first threshold value, such as a first predetermined maximum power. If, at step 118, the provided power is greater than the first predetermined maximum power, then the method advances to step 130 illustrated in FIG. 3B, such as shown in the bottom graph in FIG. 4 between times $t_2$ and $t_3$, which depicts a second drying interval of the drying phase. In some examples that include a second drying interval, the control circuit 48 can reduce the ramp rate at block 130, such as shown in the bottom graph in FIG. 4 between times $t_2$ and $t_3$. In this manner, the control circuit 48 can modify the energy delivery during a first pulse, such as a first drying pulse, in response to the measured, e.g., intermittently, first electrical parameter of the engaged biological tissue meeting a first threshold value.

The system can measure, e.g., intermittently, the first electrical parameter, such as an electrical current and, in response to the measured electrical current of the engaged biological tissue satisfying a first threshold value, such as a predetermined value, reduce or terminate the energy delivery during the therapeutic phase. In some examples, the predetermined value is an absolute current threshold value. In some examples, the predetermined value is a threshold value that can change depending on a pulse count. In some examples, the predetermined value is a change in current relative to an initial current measurement. In some examples, the predetermined value is a change in current relative to a maximum current measurement during a pulse of the therapeutic signal.

If, however, at step 118, the provided power is less than the first predetermined maximum power, then the method advances to step 120, where control circuit 48 causes measurement circuit 46 to measure a first electrical parameter, such an impedance or an electrical current conducted by the engaged biological tissue.

At step 122, control circuit 48 compares the measured electrical current (or impedance), e.g., a first electrical parameter, for this pulse with the maximum electrical current previously measured (if any), e.g., a threshold value. If, at step 122, the measured electrical current is greater than the maximum electrical current, then the method advances to step 124, where the measured electrical current is recorded as the new maximum value, and then the method returns to step 116 so as to continue the first drying interval of the drying phase by modifying the energy delivery during the first pulse. If, however, at step 122, the measured electrical current is less than the maximum electrical current, then the method advances to step 126, where control circuit 48 compares the measured electrical current with a predetermined fraction of the maximum electrical current.

If, at step 126, the measured electrical current, e.g., a measured first electrical current, is greater than the predetermined current threshold, e.g., a measured second electrical current, then the method returns to step 116 so as to continue the first drying interval of the drying phase. In some examples, the predetermined current threshold can be a ratio or fraction of the maximum electrical current, such as 0.9, 0.8, 0.66, 0.5, and 0.4. for example. In other words, control circuit 48 can continue the drying signal or pulse in response to a ratio of the measured first electrical current to the measured second electrical current exceeding a predetermined factor indicating there has not been a phase change of liquid in the engaged biological tissue. In other examples, the predetermined current threshold can be a difference rather than a ratio.

If, however, at step 126, the measured electrical current is less than the predetermined fraction of the maximum electrical current, then the method advances to step 128, where the first drying pulse of the first drying interval of the drying phase is terminated. The method then returns to step 104 so as to repeat the interrogation phase, after which the drying phase can be repeated or a sealing phase can begin. In other words, the system can monitor electrical current during a therapeutic phase to determine when that therapeutic phase should end.

In some examples and in contrast to determining whether the measured electrical current is less than the predetermined faction of the maximum electrical current at step 126, the control circuit 48 can determine whether the measured electrical current is less than the predetermined fraction (or offset) of a current value measured at a predetermined time interval following the initiation of the pulse. For impedance monitoring systems, the control circuit 48 can determine whether the measured impedance is greater than the predetermined fraction (or offset) of a resistance value measured at a predetermined time interval following the initiation of the pulse.

At step 130 (depicted in FIG. 3B), a second interval of the drying phase begins, in which control circuit 48 causes electrical-energy source 44 to provide a second drying signal, such as a second drying pulse, to the engaged biological tissue during the second drying interval of the drying phase. It should be noted that although first and second drying intervals of a drying phase are shown in FIGS. 3A and 3B, there need not be a second drying interval of the drying phase. Rather, in some examples, the drying phase can terminate during the first drying interval. Power (W) of the provided second drying signal, such as a second drying pulse, is controlled according to a second drying schedule or plan, such as using a pre-defined power curve. In a power-controlled (or voltage-controlled or current-controlled) technique, the system can control the setting of the actuation energy level. Power (or voltage or current) constraint refers to a ceiling or threshold that the controlled current is not to cross, or there is an error state.

In other examples, Voltage (V) across the engaged biological tissue is controlled during the second drying interval. In a voltage-controlled technique, the system can control the setting of the actuation energy level. Voltage constraint refers to a ceiling or threshold that the controlled voltage is not to cross, or there is an error state. In voltage-controlled implementations, the control circuit can monitor the voltage of the therapeutic signal and when the threshold or ceiling is met, the control circuit can maintain the voltage at the threshold. In some voltage-controlled implementations, the voltage can be capped at a ceiling. In other voltage-controlled implementations, the voltage can be time variant.

In the depicted example, the second drying interval uses a second drying schedule or plan that is a monotonically-increasing power schedule. In some examples, for example, the second drying schedule or plan is a linearly-increasing power schedule. Then, at step 132, control circuit 48 compares the provided power to a second predetermined maximum power. If, at step 132, the provided power is greater than the second predetermined maximum power, then the method advances to step 134, where control circuit 48 causes electrical-energy source 44 to provide power equal to the second predetermined maximum power, e.g., a power ceiling, and then method 100 advances to step 136. If, however, at step 132, the provided power is less than the second predetermined maximum power, then the method advances to step 136, where control circuit 48 causes measurement circuit 46 to measure electrical current conducted by the engaged biological tissue.

At step 138, control circuit 48 compares the measured electrical current with maximum current previously measured. If, at step 138, the measured electrical current is greater than the maximum electrical current, then the method advances to step 140, where the measured electrical current is recorded as the new maximum value, and then the method returns to step 130 so as to continue the second drying phase. If, however, at step 138, the measured electrical current is less than the maximum electrical current, then the method advances to step 142, where control circuit 48 compares the measured electrical current with a predetermined fraction of the maximum electrical current. If, at step 142, the measured electrical current is greater than the predetermined ratio or fraction of the maximum electrical current, then the method returns to step 130 so as to continue the second drying interval of the drying phase. In other words, control circuit 48 can reduce the drying signal or pulse in response to a ratio of the measured first electrical current to the measured second electrical current exceeding a predetermined factor indicating a phase change of liquid in the engaged biological tissue. In other examples, the predetermined current threshold can be a difference. If, however, at step 142, the measured electrical current is less than the predetermined faction of the maximum electrical current, then the method can exit the second interval of the drying phase and return to step 104 so as to repeat the interrogation phase, after which the drying phase can be repeated or a sealing phase can begin. In other words, the system can monitor electrical current during a therapeutic phase to determine when that therapeutic phase should end.

At step 146, a sealing or coagulation phase begins in which control circuit 48 causes electrical-energy source 44 to provide a sealing signal, such as a sealing pulse, e.g., a second pulse, to the engaged biological tissue during the sealing phase, such as shown in the bottom graph in FIG. 4 between times $t_7$ and $t_8$. Power (W) of the provided sealing signal, such as a sealing pulse, is controlled according to a sealing schedule or plan. In some examples, the sealing schedule or plan is a monotonically-increasing power schedule. Then, at step 148, control circuit 48 compares the provided power to a third predetermined maximum power. It should be note that this is an example of a predetermined power curve, which happens to have a constant power domain. If, at step 148, the provided power is greater than the third predetermined maximum power, then the method advances to step 150, where control circuit 48 causes electrical-energy source 44 to provide power equal to the third predetermined maximum power, and then method 100 advances to step 152 to measure, e.g., intermittently, a second parameter of the engaged biological tissue, such as the resistance of the tissue. If, however, at step 148, the provided power is less than the third predetermined maximum power, then the method advances to step 152, where control circuit 48 causes measurement circuit 46 to measure electrical resistance of the engaged biological tissue.

At step 154, control circuit 48 compares the measured electrical resistance with a second threshold value, such as a calculated termination resistance value. In some examples, the calculated termination resistance value resistance is calculated based on the reference resistance measured at step 106, e.g., the first resistance. For example, the termination resistance value can be a predetermined factor times the measured reference resistance. In some examples, the termination resistance value can be a sum of a predetermined resistance delta and either the measured reference resistance or a minimum value of the resistance measured during that phase or a previous phase. In some examples, the target resistance is the predetermined delta resistance, where the predetermined delta resistance is a change in resistance relative to a minimum resistance measurement during a pulse of the therapeutic signal.

If, at step 154, the measured electrical resistance is less than the calculated termination resistance, then the method returns to step 146 so as to continue the sealing phase. If, however, at step 154, the measured electrical resistance is greater than the calculated termination resistance, then the sealing phase is terminated, and the method ends. In other words, in response to the measured, e.g., intermittently, impedance meeting a second threshold value, such as changing by a predetermined delta impedance value, for example, the method can modify the energy delivery of the second pulse, such as by reducing or terminating the energy delivery during this therapeutic phase, such as a sealing phase.

In some non-limiting examples, the method shown in FIGS. 3A and 3B can be implemented by a system such that the control circuit can monitor a first electrical parameter, such as an electrical current, in a first therapeutic phase, such as a drying phase, and reduce or terminate a first pulse based on the first electrical parameter, and monitor a second electrical parameter, such as an impedance, in a second therapeutic phase, such as a sealing phase, and reduce or terminate a second pulse based on the second electrical parameter.

FIG. 4 is a graph depicting non-limiting examples of an electrotherapeutic schedule or plan used to control electrical power provided to biological tissue being sealed. In FIG. 4, Graph 200 has horizontal axis 202, vertical axes 204A-204C, and functional relations 206A-206C. Horizontal axis 202 is indicative of time (seconds). Horizontal axis has times $t_0$-$t_8$, which signify transition times between the interrogation, drying, and sealing phases disclosed in the discussion pertaining to method 100 for generating an electrotherapeutic signal for treating a biological tissue engaged by an electrosurgical instrument. These phases—the interrogation, first drying, and sealing phases—are also notated at various locations of graph 200. It should be noted that the graph of FIG. 4 is meant for purposes of explanation only. The graph of FIG. 4 depicts an example of a response and different tissues can react differently.

Vertical axis 204A is indicative of electrical power (W) provided to biological tissue engaged by an electrosurgical instrument. Functional relation 206A indicates a non-limiting example of a power/time relation corresponding to the electrotherapeutic signal generated based on the non-limiting example of a method 100 illustrated in FIGS. 3A-3B. Vertical axis 204B is indicative of electrical current conducted by the engaged biological tissue. Functional relation 206B indicates the electrical current/time relation pertaining to the electrical current conducted by the engaged biological tissue to which the electrotherapeutic signal generated via method 100 is provided. Vertical axis 204C is indicative of electrical resistance of the engaged biological tissue. Functional relation 206C indicates electrical-resistance/time relation corresponding to the electrical resistance of the engaged biological tissue to which the electrotherapeutic signal generated via method 100 is provided.

In some examples, the functional relation 206A can be a pre-defined power curve, including an interrogation phase, a drying phase, and a sealing phase. In the specific non-limiting example shown in FIG. 4, the drying phase depicts first and second drying intervals. From times $t_0$ to $t_1$, power/time relation 206A indicates the interrogation phase. In some examples, the duration of the interrogation phase is as short as is needed to obtain a reference measurement of the engaged biological tissue. For example, the duration of the interrogation phase can be less than 1.0, 0.5, 0.25, or 0.1 seconds. As indicated in graph 200, the interrogation phase is a constant-power schedule or plan having power P1 (W). From times $t_0$ to $t_1$, electrical current/time relation 206B indicates an interrogation rapid electrical current rise, followed by an electrical current plateau, which is then followed by a slight decrease in electrical current conducted by the engaged biological tissue. Because power is controlled to be constant throughout this interrogation phase, the voltage applied across the engaged biological tissue is inversely related (in a multiplicative sense as opposed to an additive sense) to the electrical current/time relation. The resistance of the engaged biological tissue can initially decrease as the temperature of the fluid in the tissue increases. Because this is the first time the interrogation phase is performed, the measured electrical resistance is not less than a minimum resistance previously measured, and therefore the method advances to the first drying phase.

From times $t_1$ to $t_2$, power/time relation 206A indicates the first interval of the drying phase. As indicated in graph 200, the first drying interval of the drying phase is an electrical-power schedule or plan that monotonically increases from powers P1 to P2 (W). From times $t_1$ to $t_2$, electrical current/time relation 206B indicates electrical current conducted by the engaged biological tissue increases throughout the first interval of the drying phase. Because power is controlled throughout this first interval of the drying phase according to a drying schedule or plan, a product of the voltage applied across the engaged biological tissue and the electrical current/time relation should yield power/time relation 206A. Although not depicted, in some examples, the electrical-resistance/time relation 206C can indicate that electrical resistance of the engaged biological tissue initially can decrease as the tissue warms, but then can increase as the tissue begins to dry during the first interval of the drying phase. Such increasing electrical resistance can indicate drying of the engaged biological tissue. Because the electrical current does not decrease below a fraction of a previously measured maximum electrical current before power/time relation 206A ramps to a predetermined threshold, the method advances to the second interval of the drying phase. If the current were to have dropped below the fraction of the previously measured maximum electrical current during this first interval of the drying phase, the subsequent second interval of the drying phase would not be necessary (e.g., it could be bypassed).

From times $t_2$ to $t_3$, power/time relation 206A indicates the second interval of the drying phase. As indicated in graph 200, the second interval of the drying phase is an electrical-power schedule or plan that monotonically increases from powers P2 to P3 (W). Using the techniques described above with respect to FIGS. 3A and 3B, a control circuit, such as the control circuit 48 of FIG. 2, can control an energy delivery of the therapeutic signal provided to the biological tissue during a portion of a therapeutic phase according to an incremental change in energy delivery as a function of a change in a measured electrical parameter of the biological tissue. For example, a control circuit can incrementally modify the power as a function of current. In some examples, the function of current is a function of an instantaneous measured change in current. In some examples, the function of the instantaneous measured change in current is a linear function. In other examples, the control circuit can incrementally modify the power as a function of resistance.

From times $t_2$ to $t_3$, electrical current/time relation 206B indicates electrical current conducted by the engaged biological tissue increases at the beginning of the second interval of the drying phase, but peaks and then decreases at the end of the second drying phase. It should be noted that a second interval of the drying phase may not be needed. In some examples, power can be controlled throughout this second interval of the drying phase such that a product of the voltage applied across the engaged biological tissue and the electrical current/time relation can yield a particular power/time relation 206A.

In some examples, the second interval of the drying phase is monotonically increasing, but at a slower rate of increase than that of the first interval of the drying phase. In other examples, the second interval of the drying phase is linearly increasing until the provided power equals a predetermined maximum level, after which time the provided power is held constant. Because the decrease in electrical current ΔI1 e.g., a measured change in current (such as at block 126 in FIG. 3A), results in a current that is less than a predetermined fraction of the maximum electrical current measured, the method returns to the interrogation phase, which is shown at time $t_3$. In other words, the change in electrical current ΔI1 causes the method to enter the interrogation phase at time $t_3$. It should be noted that in the non-limiting example shown in FIG. 4, the change in electrical current ΔI1 that causes the method to enter the interrogation phase is after time $t_2$. However, in other examples, the change in electrical current ΔI1 that causes the method to enter the interrogation phase can be after time $t_1$ during the first interval of the drying phase, and a second interval of the drying phase may not be needed. If, however, the decrease in electrical current ΔI1 had instead been less than the predetermined fraction of the maximum electrical current measured, then the method would have remained in the drying phase.

As seen in FIG. 4, in some examples, the pre-defined power curve 206A can include two or more linear portions, such as shown between $t_1$ and $t_2$ and between $t_2$ and $t_3$.

From times $t_3$ to $t_4$, power/time relation 206A depicts the interrogation phase again. As indicated in graph 200, the interrogation phase is a constant-power schedule of power P1 (W). Because power is controlled to be constant throughout this interrogation phase, the voltage applied across the engaged biological tissue is inversely related (in a multiplicative sense as opposed to an additive sense) to the electrical current/time relation. Electrical-resistance/time relation 206C indicates that the electrical resistance of the engaged biological tissue is decreasing throughout this performance of the interrogation phase. Decreasing electrical resistance can be a result of condensing of fluid in the tissue or migration of fluid into the tissue. Because the measured electrical resistance is not greater than a sum of the reference resistance and a predetermined delta resistance, the method advances again to the first drying phase.

From times $t_4$ to $t_5$, power/time relation 206A indicates another first interval of the drying phase. The power/time relation from times $t_4$ to $t_5$ is similar to the power/time relation 206A from times $t_1$ to $t_2$ and, for purposes of conciseness will not be described in detail again.

From times $t_5$ to $t_6$, power/time relation 206A indicates another second interval of the drying phase. The power/time relation from times $t_5$ to $t_6$ is similar to the power/time relation 206A from times $t_2$ to $t_3$ and, for purposes of conciseness will not be described in detail again. Because power is controlled to be constant throughout this second interval of the drying phase, a product of the voltage applied across the engaged biological tissue and the electrical current/time relation should yield power/time relation 206A. Because the decrease in electrical current ΔI2, e.g., a measured change in current (such as at block 142 in FIG. 3B), is less than a predetermined fraction of the maximum electrical current measured, the method returns to the interrogation phase.

From times $t_6$ to $t_7$, power/time relation 206A indicates another interrogation phase. The power/time relation from times $t_6$ to $t_7$ is similar to the power/time relation 206A from times $t_3$ to $t_4$ and, for purposes of conciseness will not be described in detail again. Because the measured electrical resistance is now greater than a sum of the reference resistance and a predetermined delta resistance, the method advances to the sealing phase.

From times $t_7$ to $t_8$, power/time relation 206A indicates the sealing phase. As indicated in graph 200, the sealing phase is an electrical-power schedule or plan that monotonically increases from power P1 to power P3 (W). From times $t_7$ to $t_8$, electrical current/time relation 206B indicates an increasing electrical current conducted by the engaged biological tissue throughout the sealing phase. Electrical-resistance/time relation 206C indicates that the electrical resistance of the engaged biological tissue is increasing this performance of the sealing phase. Increasing electrical resistance can be a result of drying and thereby sealing of the engaged biological tissue. Because the measured electrical resistance is now greater than a predetermined termination resistance, the sealing phase is terminated, and the method ends.

Figure 5:
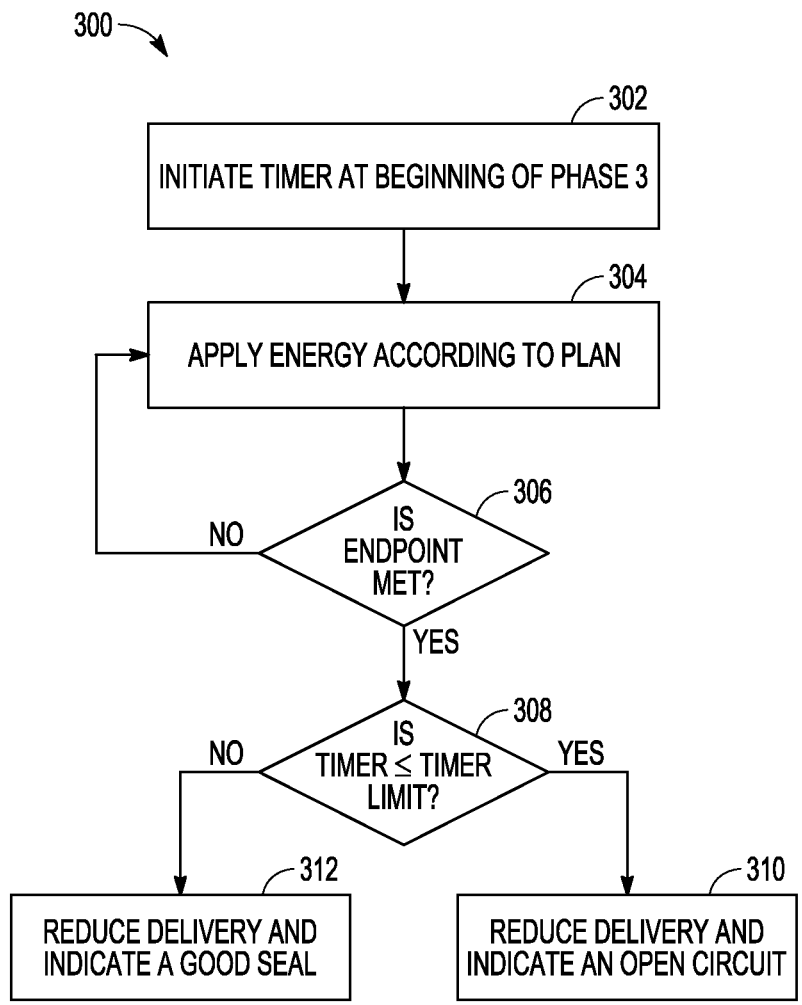
FIG. 5 is a flow diagram depicting an example of open circuit check techniques that can be used in a surgical system.
Figure 6:
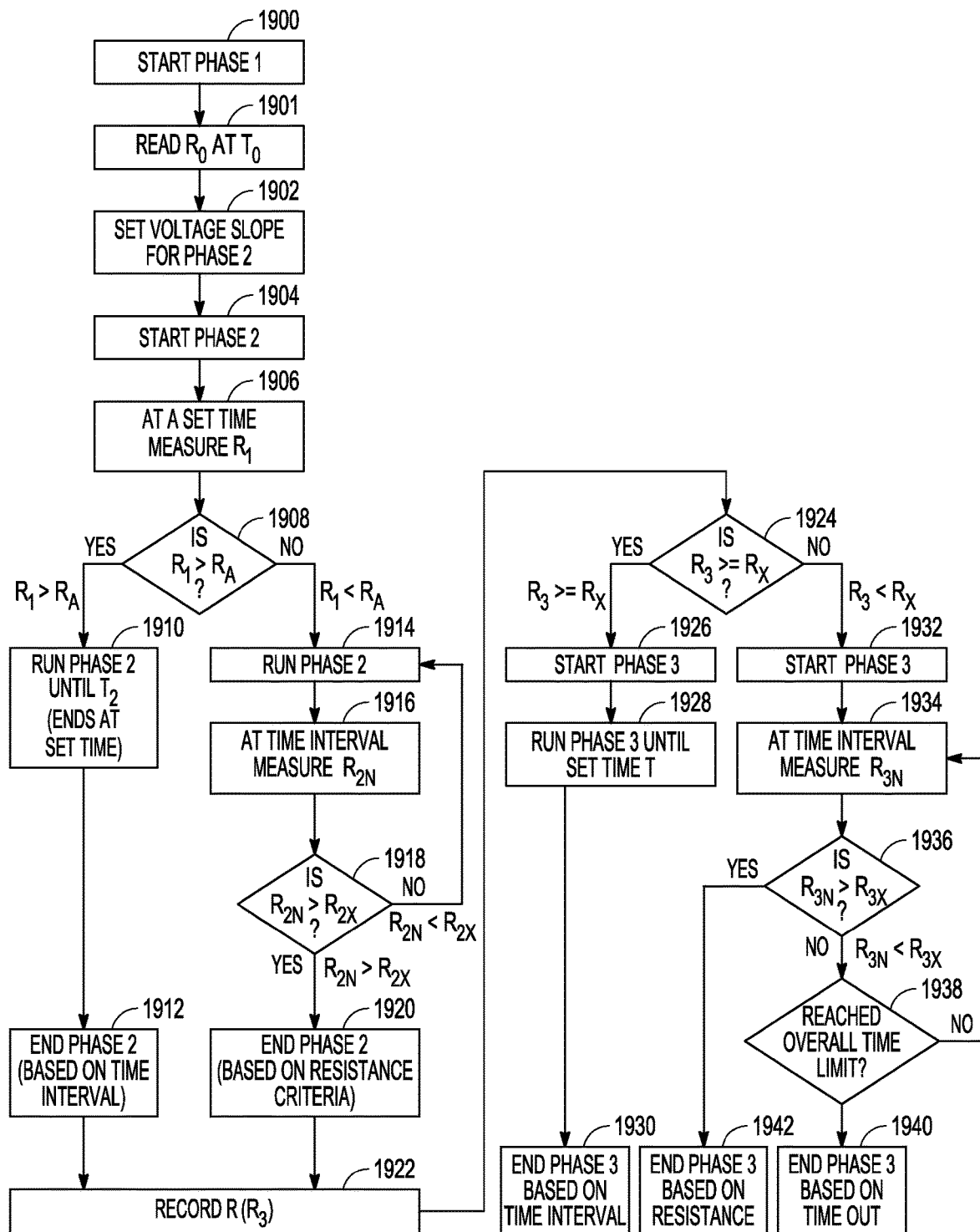
FIG. 6 is a flow chart of a biological tissue-sealing method that uses an electrical-power schedule corresponding to a size of biological tissue engaged by the electrosurgical instrument.

Predictive Phase Control of an Electrotherapeutic Signal (FIGS. 5-6)

An electrosurgical procedure can have one or more electrotherapeutic phase. For example, an electrosurgical tissue-sealing technique can have an interrogation phase, a drying phase, and/or a sealing phase. During each of these electrotherapeutic phases, a corresponding electrotherapeutic signal, such as, for example, an interrogation signal, a heating signal, a drying signal, a cauterizing signal, etc., can be provided to biological tissue engaged by an electrosurgical instrument. The electrotherapeutic signal provided to the engaged biological tissue can be tailored to the technique being performed and/or to the specific tissue. Thus, each electrosurgical signal can be different for different procedures, for different tissue types and quantities, and for different electrotherapeutic phases. These differences in different electrotherapeutic signals can be obtained using different electrotherapeutic schedules and/or different phase-control criteria. Differences between different electrotherapeutic schedules can arise from differences in controlled electrical parameters, and/or differences in phase control criteria. As described above, differences in controlled electrical parameters include apparent power (VA), real power (W), voltage (V) and/or electrical current (A) of the electrotherapeutic signal. Phase-control criteria include criteria for commencement and termination of a phase, as well as criteria for intra-phase control. Such phase-control criteria include contemporaneous phase-control criteria and predictive phase-control criteria.

Contemporaneous phase-control is performed by using a real-time measurement to control a phase. Predictive phase-control is performed by using a reference measurement taken at a reference time to generate a future phase-control criteria. For example, a tissue-resistance measurement taken before or during a drying phase can be used to generate a time duration for continuing the drying phase. In some examples, a tissue-resistance measurement can be used to select one of a plurality of predetermined electrotherapeutic schedules. The selected one of the plurality of predetermined electrotherapeutic schedules can be used in a subsequent electrotherapeutic phase.

The reference measurement of tissue resistance can be indicative of a vessel size, for example. Different size vessels can be heated using different electrotherapeutic schedules or plans, and/or different phase-control criteria. Appropriate electrotherapeutic schedules or plans customized for vessel sizes can lead to more secure sealing and less trauma to nearby tissue. To ensure proper sealing of the engaged vessel, the electrotherapeutic schedule can be tailored according to size of the vessel to be sealed. The vessel size can be estimated based on a measured reference resistance of the engaged vessel. Vessel sealing can then proceed according to the electrotherapeutic schedule that is determined based on the measured reference resistance of the engaged vessel.

Described below with respect to FIG. 6 are, among other things, techniques for predicting and delivering energy based on the size of the tissue detected. After an electrosurgical generator, such as electrosurgical generator 12 of FIG. 2, delivers an initial application of energy to the biological tissue via an electrosurgical device, a control circuit, such as the control circuit 48 of FIG. 2, and a measurement circuit, such as the measurement circuit 46 of FIG. 2, can measure or calculate the tissue impedance at a point in time. The control circuit can then determine the type of tissue, e.g., small vessel or large vessel, in contact with the electrosurgical device, such as between the jaws of electrosurgical device, and then deliver energy for the type of tissue that has been detected.

FIG. 6 is a flow chart of a biological vessel-sealing method that uses an electrical-power schedule corresponding to a size of biological vessel engaged by the electrosurgical instrument. The method FIG. 6 uses three therapeutic phases: Phase 1 is an interrogation phase, Phase 2 is a desiccation or drying phase, and Phase 3 is a vessel welding phase. In Phase 1, the electrosurgical system, such as the electrosurgical system 10 of FIG. 1, can perform error checking and generate and deliver an interrogation signal to the engaged tissue, such as according to an interrogation schedule. Although described in FIG. 6 as being voltage-controlled, the control circuit can deliver the energy using either power-controlled techniques or voltage-controlled techniques. In voltage-controlled techniques, current can be capped but allowed to move freely according to the responding impedance, which can allow for a variable power delivery.

Using the techniques of this disclosure, the method can begin a phase, such as Phase 2, without the control circuit having determined what criteria it will use to terminate the phase. For example, as described in more detail below, the method starts Phase 2 and the control circuit, and the measurement circuit can determine an impedance measurement of the tissue. In response, the control circuit can determine whether to terminate Phase 2 based on a time measurement or based on iterative impedance measurements. In this manner, the method can continue applying power and iteratively comparing an impedance measurement to a threshold impedance value.

If the control circuit determines that the impedance R2N (or any of the subsequent impedance measurements, if needed) is greater than or equal to the impedance R2X ("YES" branch of block 1918), then the control circuit can terminate Phase 2 at block 1920 based on an impedance criterion (in contrast to the time criterion described above for the open loop process).

After the control circuit terminates Phase 2, regardless of whether Phase 2 terminated based on time or an impedance measurement, the control circuit can calculate and store an impedance measurement R3 at block 1922. Next, at block 1924, the control circuit can determine whether the present impedance measurement R3 is less than or equal to an impedance threshold value RX.

If the control circuit determines that the impedance R3 is greater than or equal to the impedance RX ("YES" branch of block 1924), then the tissue is a small vessel and the method can start Phase 3 at block 1926. At block 1928, the control circuit can run Phase 3 as an open loop and continue delivering power until a timer expires at a time T3. At block 1930, Phase 3 ends based on a time interval.

However, if the control circuit determines that the impedance R3 is not greater than or equal to the impedance RX ("NO" branch of block 1924), then the tissue is a large vessel and the method can start Phase 3 at block 1932 and the control circuit can run Phase 3 as a closed loop. At block 1934, the control circuit can measure an impedance R3N at a set time interval. At block 1936, the control circuit can determine whether the present impedance measurement R3N is greater than or equal to an impedance threshold value R3X.

If the control circuit determines that the impedance R3N is not greater than or equal to the impedance R3X ("NO" branch of block 1936), then at block 1938 the control circuit can determine whether a maximum time limit has been reached. If the control circuit determines that the maximum time limit has been reached ("YES" branch of block 1938), then the control circuit can terminate Phase 3 at block 1940. In some examples, the time limit can be an elapsed time from the start of Phase 1.

However, if the control circuit determines that the maximum time limit has not been reached ("NO" branch of block 1938), then the control circuit can continue applying power and return to block 1934. The method can repeat the impedance measurement at a time interval at block 1934 and determine whether the new impedance measurement is greater than or equal to the threshold impedance value R3X at block 1936. In this manner, the method can continue applying power and iteratively comparing an impedance measurement to the threshold impedance value R3X.

If the control circuit determines that the impedance R3N is greater than the impedance R3X ("YES" branch of block 1936), then at block 1942 the control circuit can terminate Phase 3 based on an impedance measurement (in contrast to the time criterion described above for the open loop process of Phase).

Figure 7A:
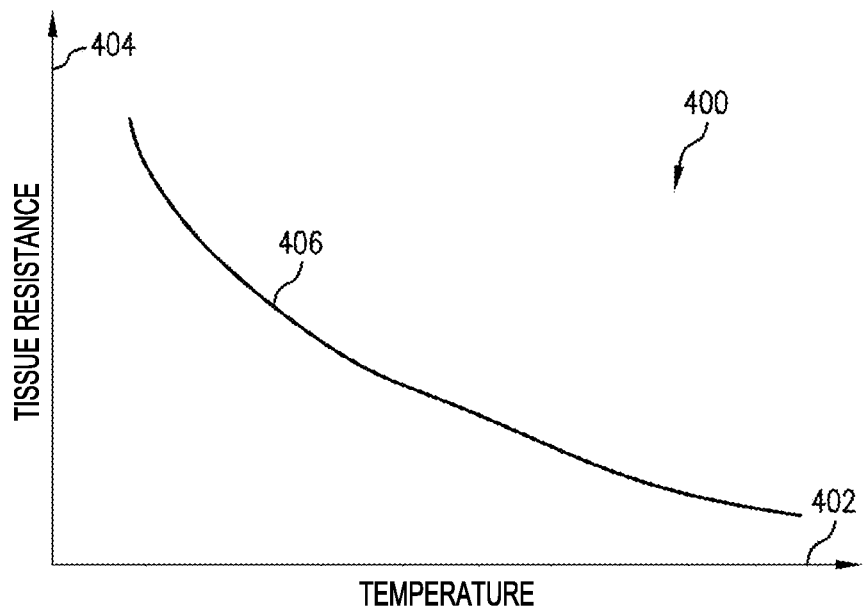
FIG. 7A is a graph depicting measured tissue resistance as a function of jaw temperature of a forceps.
Figure 7B:
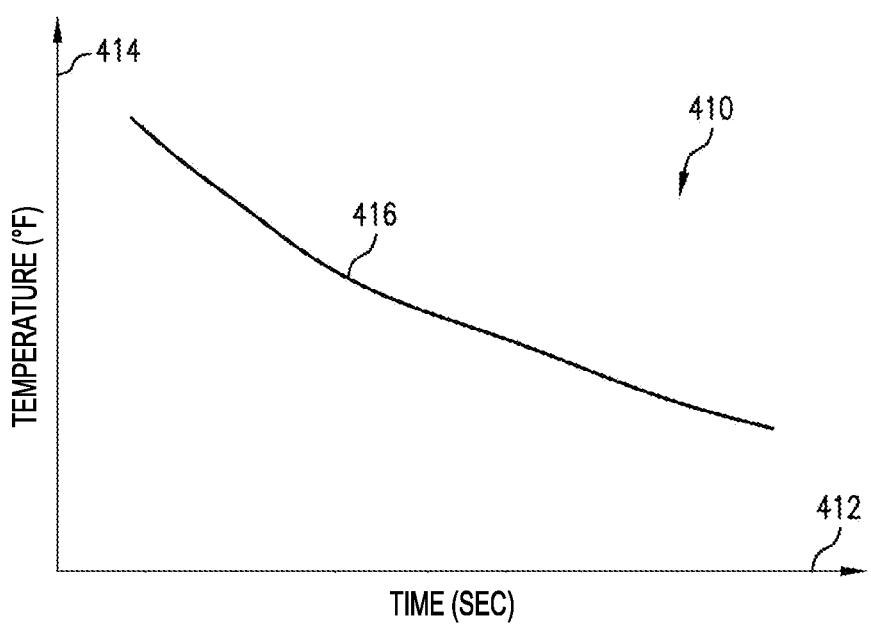
FIG. 7B is a graph depicting jaw temperature vs. time after termination of power application.
Figure 9:
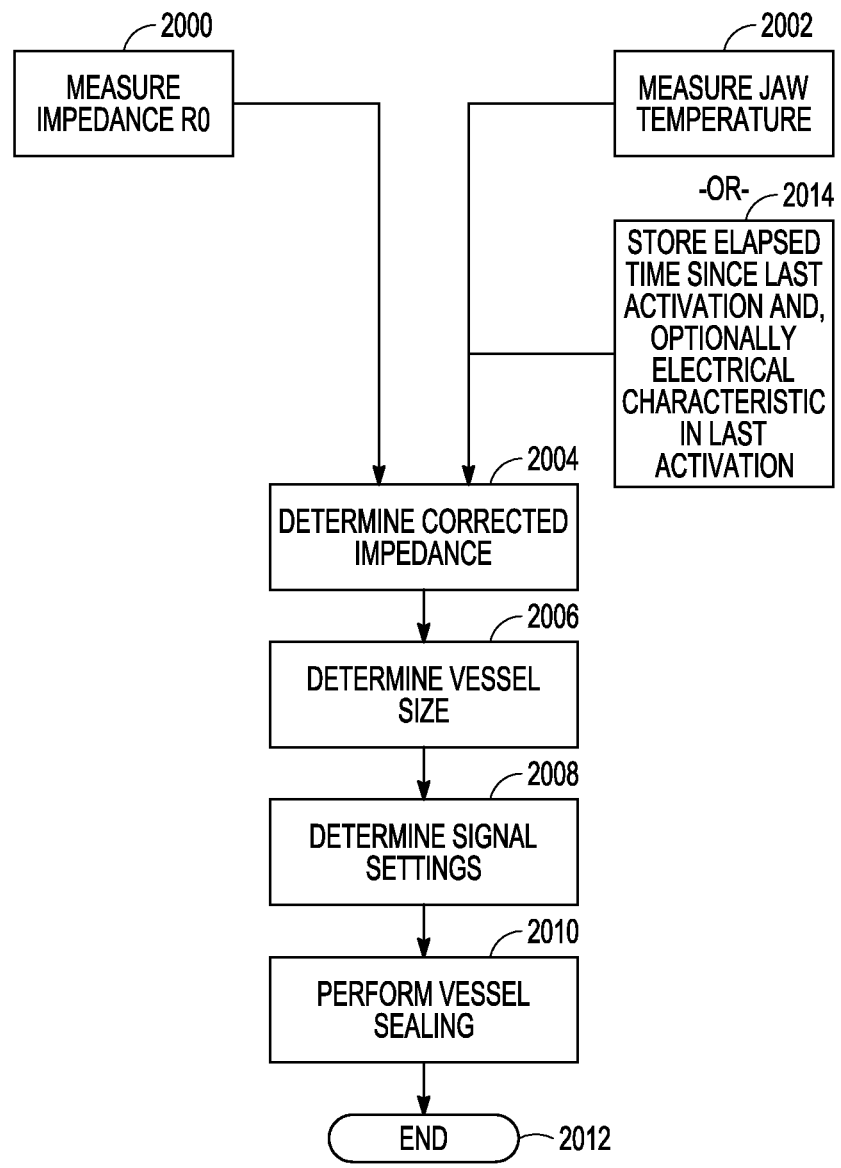
FIG. 9 depicts a flow chart a method for compensating measurements of tissue resistance as a function of time after power application.

Correction of Measured Electrical Resistance of Engaged Biological Tissue (FIGS. 7A-7B and 9)

The various electrical measurements described above can be used in the determination of an electrotherapeutic schedule and/or in the determination of phase-control criteria. As such, accurate measurements facilitate the generation of an electrotherapeutic signal that will succeed in its therapeutic purpose. Temperatures of an electrosurgical instrument and of biological tissue engaged thereby affect electrical measurements of the engaged biological tissue. Such temperature/measurement relations can introduce uncertainty and/or complication in using such electrical measurements in determining an electrotherapeutic schedule and/or phase-control criteria. For example, comparison of two electrical measurements of an engaged tissue taken when the engaged tissue and/or the electrosurgical instrument is at different temperatures can be complicated.

Some examples correct electrical measurements of engaged tissue so as to account for temperatures of electrosurgical instruments and/or of biological tissues. Measured electrical resistance of biological tissue, for example, can be corrected based on actual temperature measurements of the electrosurgical instrument. In some examples the electrosurgical instrument will be equipped with a temperature sensor in thermal communication with the distal end that engages the biological tissue. In other examples, the measured electrical resistance of biological tissue can also be corrected based on predicted temperature of the tissue and/or the electrosurgical instrument base on various indirect measurements. For example, measured tissue resistance can be corrected based on a time interval between a reference time and a measurement time, between which electrical power has been delivered to the biological tissue. In some examples the measured tissue resistance can be corrected based on calculation of energy provided to the engaged tissue prior to the electrical measurement.

FIG. 7A is a graph depicting measured tissue resistance as a function of jaw temperature of a forceps. In FIG. 7A, graph 400 includes horizontal axis 402, vertical axis 404 and electrical-resistance/temperature relation 406. Horizontal axis 402 is indicative of jaw temperature of a forceps. Vertical axis 404 is indicative of measured electrical resistance of a tissue clamped between opposable jaw members of a forceps, such as forceps 14 depicted in FIG. 1. Electrical-resistance/temperature relation 406 depicts measurements of a specific biological tissue clamped by the opposable jaw members, which have been heated to various temperatures. Electrical-resistance/temperature relation 406 depicts a monotonically-decreasing function, in which the measured electrical resistance decreases as jaw temperature increases. Such variations in measured electrical resistance can arise from many factors, including electrical resistance dependencies on tissue temperature, tissue-liquid phase, jaw-tissue interface, jaw temperature, etc.

Such variations in measured tissue resistance can introduce uncertainty and/or complication in using such measured electrical resistance to determine an electrotherapeutic schedule and/or phase-control criteria. Some of the electrical resistance dependencies are undesirable, in that they are not indicative of therapeutic effects upon the biological tissue. Therefore, compensation of these undesirable dependencies can improve the quality of such electrical resistance measurements. Various methods of compensating electrical measurements of biological tissue can be performed so as to provide measurements that better indicate the therapeutic effects of an electrotherapy treatment.

FIG. 7B is a graph depicting jaw temperature vs. time after termination of power application. In FIG. 7B, graph 410 includes horizontal axis 412, vertical axis 414 and temperature-time relation 416. Horizontal axis 412 is indicative of time after application of an electrotherapeutic signal has been provided to a biological tissue. During this post-therapy time, no power is delivered to the biological tissue. Vertical axis 414 is indicative of measured temperature of the opposable jaw members of a forceps used to provide the electrotherapeutic signal to the tissue. Temperature-time relation 416 depicts measurements of jaw temperature at various post-therapy times. Temperature-time relation 416 is a monotonically-decreasing function of time that asymptotically approaches room temperature. Such a temperature-time relation can be characterized by a time constant indicative of a rate of decay.

The relations depicted in graphs 400 and 410 can be used in modeling the jaw temperature as a function of power application and time duration post-power application. For example, the power dissipated by biological tissue engaged by an electrosurgical instrument can be used to predict temperature of that biological tissue, as well as the temperature of the engaging portion (e.g., opposable jaw members 36 and 38 depicted in FIG. 1) of the electrosurgical instrument. Such jaw temperature-power application relation can be determined theoretically (e.g., using the tissue volume within the engagement of the opposable jaw members) as well as empirically (e.g., by characterizing the instrument). In some examples, the position of the engaged jaw members can be used in determining the tissue volume within the engagement of the jaw members, for example. In some examples, combinations of theoretical and empirical characterization can be used to model the relation between jaw temperature and power application. The jaw temperature-time post-therapy can similarly be characterized empirically and/or theoretically.

Furthermore, the electrical resistance dependencies that are undesirable, in that they are not indicative of therapeutic effects upon the biological tissue, can be characterized empirically and/or theoretically. These various characterizations or models can then be combined to determine a compensated resistance value, based on the measured resistance value. For example, measurements of tissue resistance taken during application of an electrotherapeutic signal to the biological tissue can use a calculated jaw temperature based on the electrotherapeutic schedule for compensation. After application of the electrotherapeutic signal to the biological tissue, measurements of tissue resistance can be compensated using a post-therapy time duration.

Figure 8:
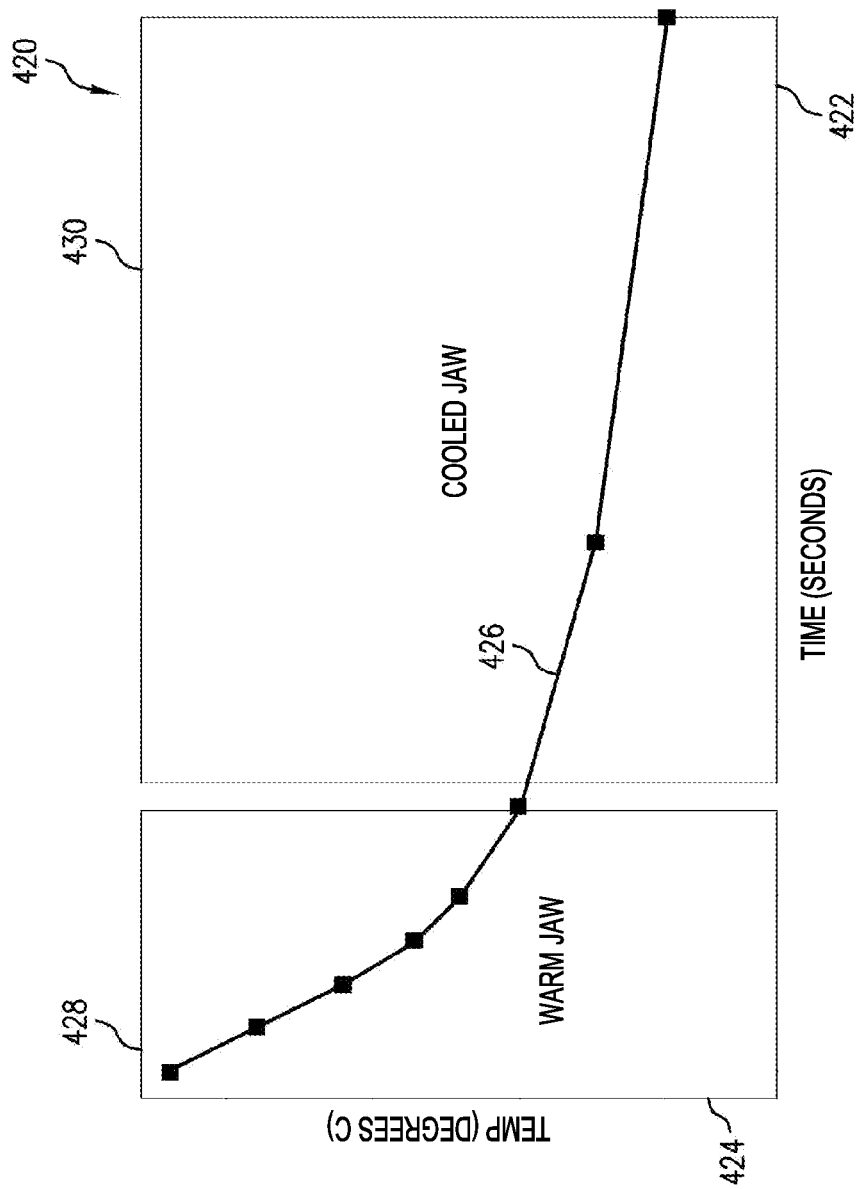
FIG. 8 is a graph depicting resistance compensation vs. time after power application.

FIG. 8 is a graph depicting electrical resistance compensation vs. time after power application. In FIG. 8, graph 420 includes horizontal axis 422, vertical axis 424 and delta resistance/time relation 426. Horizontal axis 422 is indicative of time after application of an electrotherapeutic signal has been provided to a biological tissue. During this post-therapy time, no power is delivered to the biological tissue. Vertical axis 424 is indicative of delta resistance needed to compensate the measured tissue resistance. In some examples, instead of using an additive delta-resistance corrective, a multiplicative factor can be used. Delta-resistance/time relation 426 depicts the delta-resistance correction factor need to compensate for jaw temperature at various post-therapy times. Delta-resistance/time relation 426 is a monotonically-decreasing function of time that asymptotically approaches zero.

In one example, measured tissue resistance can be compensated when electrosurgical instrument is hotter that a predetermined threshold, but not when the electrosurgical instrument is cooler than the predetermined threshold. FIG. 8 depicts operating zones 428 and 430, delimiting these two compensation regimes (e.g., hot and cold instrument regimes). Operating zone 428 spans from times immediately after application of electrotherapeutic signal to a biological tissue until a predetermined time post-application of the electrotherapeutic signal to a biological tissue. During this hot-instrument regime, measurements of tissue resistance are compensated by adding a predetermined delta-resistance value to the measured tissue-resistance values. In the example depicted in FIG. 8, the time delimiting the transition from hot instrument to cold instrument regimes is around 30 seconds post-therapy. No compensation of measurements of tissue resistance are performed in the cold-instrument regime.

Modification of Initial Impedance (FIG. 9)

The control circuit of an electrosurgical generator, such as the control circuit 48 of the electrosurgical generator 12 of FIG. 2, can use a predictive algorithm to generate and deliver an electrotherapeutic signal to biological tissue engaged to an electrosurgical device, such as between the jaws of the forceps 14 of FIG. 1. The predictive algorithm can include multiple phases. For example, Phase 1 can use low power energy to initially access the vessel impedance and various energy delivery parameters. Based on the initial impedance determined in Phase 1, the system can determine the size of the vessel to be sealed, set the parameters in a Phase 2 to dry the vessel tissue, and provide a proper energy level and duration in a Phase 3 to seal the vessel.

It can be challenging to accurately predict the vessel sizes, however. For example, the initial vessel impedance, which can be used to determine the vessel sized, can be affected by the jaw temperature of the electrosurgical device. The jaw can have a high temperature if the user tries to seal a second vessel right after sealing a first vessel. The high temperature can affect the initial vessel impedance measurement.

The present inventors have recognized a need to reduce the temperature effects of the initial impedance measurement and improve vessel size prediction. As described in more detail below, the present inventors have recognized that in some examples, a temperature of the jaw can be determined using a temperature sensor coupled to the jaw and then the measured impedance can be modified using a correction factor based on the jaw temperature. In other examples, the present inventors have recognized that the measured impedance can be modified using a correction factor based on one or both of an elapsed time from a previous activation or electrical characteristic(s) of the previous activation. Using the modified impedance value, the electrosurgical system can more accurately predict the size of the vessel, which can be used for determining settings for the electrosurgical generator.

FIG. 9 is a flow diagram of a biological vessel-sealing method that can compensate measurements of tissue impedance after power application. At block 2000, a control circuit and a measurement circuit, such as the control circuit 48 and the measurement circuit 46 (both of FIG. 2) can measure, in Phase 1, an initial impedance R0 of the biological tissue engaged to the electrosurgical device, such as the forceps 14 of FIG. 1. At block 2002, the control circuit and the measurement circuit can measure, in Phase 1, a temperature of a jaw of the electrosurgical device using a temperature sensor coupled to the jaw.

At block 2004, using the measured impedance and the measured jaw temperature, the control circuit can query a stored data log or set, such as a look-up table, and determine or select a adjusted or correct impedance that is a modification of the initial impedance R0 to account for the temperature of the jaws.

At block 2006, the control circuit can determine a vessel size using the determined adjusted impedance. For example, using an algorithm or another stored data set, the control circuit can determine the vessel size using the adjusted impedance.

Then, at block 2008, the control circuit can use the determined vessel size to determine various electrical parameters that define the electrosurgical signal that the electrosurgical generator will generate and deliver to the biological tissue of the vessel. In some examples, the vessel size can be determined to be either a small vessel or a large vessel and there can be two electrosurgical signal settings that correspond to those two vessel sizes. In other examples, there can be continuum of vessel sizes and electrosurgical settings that correspond to those vessel sizes.

At block 2010, the control circuit can control the delivery of the electrosurgical signal to the vessel using the determined signal settings to perform sealing and the method can end at block 2012.

As shown at block 2014, instead of using the jaw temperature, some examples can store an elapsed time since the last activation. The longer the elapsed time, the more the jaws have cooled. In this way, the elapsed time since the last activation can be used as a proxy for the jaw temperature.

At block 2004, the control circuit can use the measured initial impedance R0 and the elapsed time from the last activation to determine an adjusted impedance. In some examples, the control circuit can compare the elapsed time to a time T, e.g., 20 seconds, and if the elapsed time is greater than or equal to T, then the control circuit can use the initial impedance as the adjusted impedance. However, if the elapsed time is not greater than or equal to T, then the control circuit can add a compensation value to the initial impedance R0 to determine the adjusted impedance. As an example, the compensation value can be between about 80-90 ohms. It should be noted that the compensation value and the time T can depend on the design of the jaw.

In some examples, rather than adding a compensation value to determine the adjusted impedance, the control circuit can query a stored data log or set, such as a look-up table, and determine or select a adjusted impedance that is a modification of the initial impedance R0 to account for the elapsed time since the previous activation.

After the control circuit determines the adjusted impedance, the method can proceed to block 2006 and beyond, as described above, to determine the vessel size, signal settings, and perform vessel sealing.

At block 2014, in some examples, one or more electrical characteristics from the previous activation can be used in addition to the elapsed time since the last activation. For example, the control circuit can use the amount of energy or a current from the previous activation to determine whether the previous activation generated a large amount of heat on the jaw. If the activation was accidental or quickly terminated, little energy or current would have been delivered to the tissue and the jaw would not be heated significantly.

In some examples, the control circuit can determine the amount of energy from the previous activation by integrating the power curve of the previous activation. In other examples, the control circuit can determine the amount of energy from the previous activation by retrieving from a stored data set the application time and the average power delivered and multiplying the time and average power delivered. The elapsed time information combined with the energy or current information from the previous activation can improve the accuracy of the initial impedance R0 measurement and can increase the capability of the system to determine the vessel size. The elapsed time, temperature, and the electrical characteristics, such as energy and current, can be more generally referred to as "sealing parameters".

In some examples that use both the elapsed time and an electrical characteristic, the control circuit can use the initial impedance R0 as the adjusted impedance if the electrical characteristic, such as energy or current, is below a threshold value. If the electrical characteristic is not below the threshold value, then the method can then use the elapsed time to determine the adjusted impedance.

If the elapsed time is greater than a threshold, which would indicated that the jaws have cooled sufficiently, the control circuit can use the initial impedance R0 as the adjusted impedance. However, if the elapsed time is not greater than a threshold, the control circuit can add a compensation value, between about 80-90 ohms, to the initial impedance R0 to determine the adjusted impedance.

In some examples, rather than adding a compensation value to determine the adjusted impedance, the control circuit can query a stored data log or set, such as a look-up table, and determine or select a adjusted impedance that is a modification of the initial impedance R0 to account for the elapsed time since the previous activation and an electrical characteristic, such as energy or current, from the previous activation.

After the control circuit determines the adjusted impedance, the method can proceed to block 2006 and beyond, as described above, to determine the vessel size, signal settings, and perform vessel sealing.

In the examples described above, if the control system was unable to definitively determine the elapsed time (and, if used, the electrical characteristic, such as energy or current), the control circuit can determine an adjusted impedance that corresponds with a large vessel. Defaulting to a large vessel setting can enhance the safety of vessel sealing.

By using the techniques described above, the control circuit can deliver an electrotherapeutic signal to biological tissue engaged to the electrosurgical device, measure an impedance of the engaged biological tissue, measure an electrosurgical device sealing parameter, and determine an adjusted impedance based on a relationship between the electrosurgical device sealing parameter and the measured impedance.

Reducing Sticking of Biological Tissue to Electrosurgical Instrument by Pulsing Electrical Power of Electrotherapeutic Signal (FIGS. 10A-10D and 11)

Figure 10A:
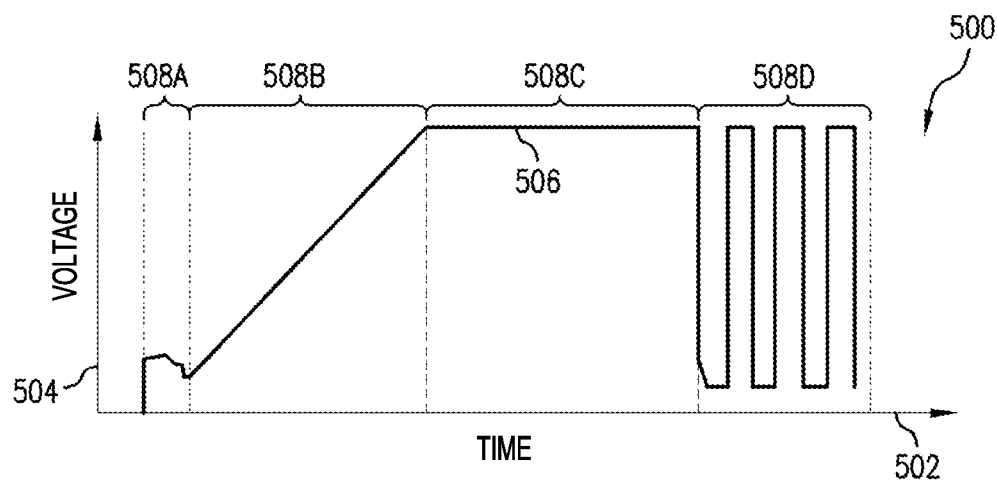
FIGS. 10A-10D are graphs of electrical parameters of an electrotherapeutic signal of an electrotherapy having a pulsed sticking reduction portion

FIGS. 10A-10D are graphs of electrical parameters of an electrotherapeutic signal of an electrotherapy having a pulsed sticking reduction portion. In FIG. 10A, graph 500 includes horizontal axis 502, vertical axis 504 and voltage/time relation 506. Horizontal axis 502 is indicative of time. Vertical axis 504 is indicative of voltage of an electrotherapeutic signal provided to tissue engaged by an electrosurgical instrument. Voltage/time relation 506 depicts measurements of a voltage difference taken at times indicated by horizontal axis 502. The voltage difference is applied across tissue engaged by an electrosurgical instrument. As shown in graph 500, voltage/time relation has four phases 508A-508D. The first phase 508A is an interrogation phase, during which a modest voltage is provided to the engaged tissue, so as to obtain an initial measurement of tissue resistance.

Following interrogation phase 508A is second phase 508B, which is a drying phase. During drying phase 508B, the voltage difference provided across the engaged tissue is monotonically increasing. In the depicted example, the voltage difference provided across the engaged tissue is linearly increasing. In some examples, drying phase 508B will have an initial slope that is greater than a final slope. In some examples, instead of controlling the voltage difference applied across the engaged tissue during the drying phase, another electrical parameter is controlled. For example, in some examples, the current conducted by or the power (real or apparent) provided to the engaged tissue is controlled.

Each of the controlled parameters provides various advantages and disadvantages as compared with the other controlled parameters. For example, controlling the voltage difference across the engaged tissue requires measurements of only the voltage difference provided thereacross. As the tissue heats, however, the tissue resistance generally increases, thereby causing a reduced current to flow therethrough. The rate of heating is thus slowed as the power provided to the tissue decreases in response to increased tissue resistance.

Controlling the current conducted by the engaged tissue requires measurements of only the current conducted thereby, which can be readily performed by measuring voltage through a small series resistor, for example. As disclosed above, heating of the tissue generally causes an increase of the tissue resistance, thereby causing an increased voltage difference thereacross. The rate of heating is thus accelerated as the power provided to the tissue increases in response to increased tissue resistance.

Controlling real power provided to the engaged tissue, however, requires measurements of both voltage difference across and current conducted by the engaged tissue. As the tissue heats, and the tissue resistance changes, both the voltage applied across and the current conducted by the engaged tissue is adjusted so as to maintain power according to an electrotherapeutic schedule. The rate of heating is proportional to the power provided to the engaged tissue, and therefore is controlled, such as, for example, real power (W) or electrical current (I).

Following drying phase 508B is third phase 508C, which is a sealing phase. During sealing phase 508C, the voltage difference provided across the engaged tissue is constant. In some examples, sealing phase 508C will not be constant. In some examples, instead of controlling the voltage difference applied across the engaged tissue during the sealing phase, another electrical parameter is controlled.

Following sealing phase 508C is fourth phase 508D, which is a sticking-reduction phase. During sticking-reduction phase, the voltage is pulsed between voltage maxima and voltage minima. Such pulsing alternately heats and permits cooling of the engaged tissue. The sticking-reduction plan can have alternating electrical-power minima and maxima, where each of the electrical-power minima are below a predetermined threshold configured to permit a temperature of the clamped biological tissue to fall below a liquid/gas phase-change threshold so as to permit liquid to exist in the clamped biological tissue. In some examples, each of the electrical-power minima of the sticking-reduction plan is maintained for a first predetermined time duration. In some examples, the first predetermined time duration is greater than or equal to 5 milli-seconds. In some examples, the first predetermined time duration is greater than or equal to 10 milli-seconds. In some examples, the first predetermined time duration is greater than or equal to 50 milli-seconds.

During the cooling portions of the pulsed waveform, liquid, which had been previously driven out of the engaged tissue, can return to the engaged tissue. In the depicted example, the pulsed waveform is periodic, in that each cycle is identical to the cycle preceding it. In some examples, the pulsed waveform is not periodic. For example, each pulse maxima can be less than the preceding pulse maxima.

Sticking-reduction phase 508D can be initiated in various manners. Sticking-reduction phase commences after proper sealing of the engaged tissue has been completed. In some examples, predictive phase control can be used to initiate or commence sticking reduction phase 508D. For example, tissue resistance can be measured at a reference time during interrogation phase 508A, drying phase 508B, or sealing phase 508C. Time duration of the sealing phase can be predicted based on the tissue resistance measured at the reference time. Sticking reduction phase 508D can commence in response to the predicted time duration of the sealing phase having elapsed. In some examples, tissue therapy can continue during the sticking reduction phase.

Figure 10B:
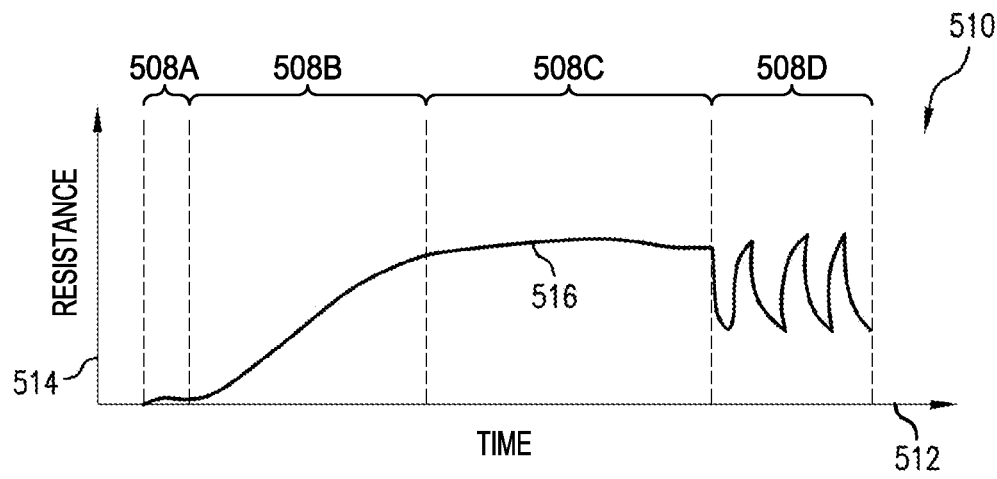

In FIG. 10B, graph 510 includes horizontal axis 512, vertical axis 514 and tissue-resistance/time relation 516. Horizontal axis 512 is indicative of time. Vertical axis 514 is indicative of electrical resistance of the tissue engaged by an electrosurgical instrument. Tissue-resistance/time relation 516 depicts measurements of tissue resistance taken at times indicated by horizontal axis 512. As shown in graph 510, tissue resistance is low during interrogation phase 508A, increases during drying phase 508B, and remains high throughout sealing phase 508C. During sticking-reduction phase 508D, tissue resistance alternates between low and high values. The low measurements of tissue resistance obtained at during the minima of the pulsed waveform are indicative of liquid returning to the engaged tissue.

Figure 10C:
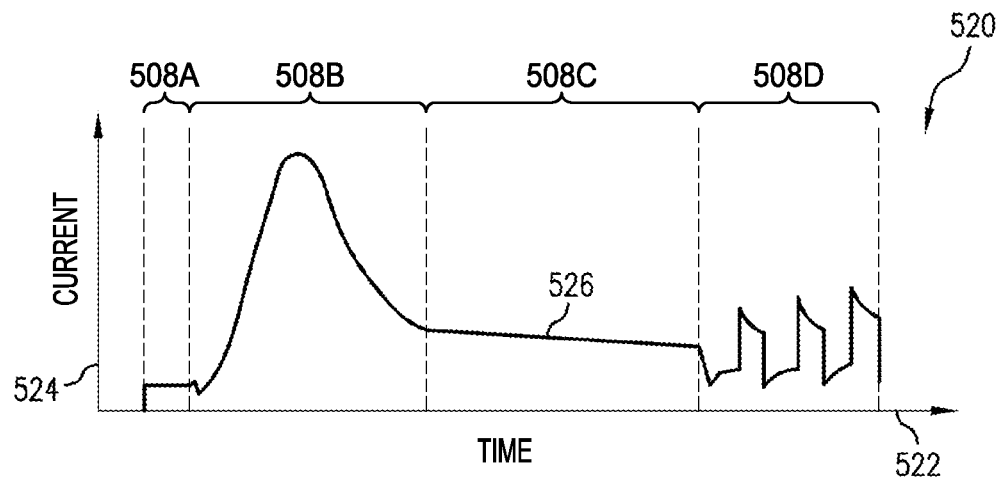

In FIG. 10C, graph 520 includes horizontal axis 522, vertical axis 524 and current/time relation 526. Horizontal axis 522 is indicative of time. Vertical axis 524 is indicative of current conducted by the tissue engaged by an electrosurgical instrument. Current/time relation 526 depicts measurements of current taken at times indicated by horizontal axis 522. As shown in graph 520, current increases at the beginning of drying phase 508B, but then decreases at the end of drying phase 508B as the tissue resistance increases. The current then remains low throughout sealing phase 508C. During sticking-reduction phase 508D, current is substantially periodic with maxima that are greater than the current values obtained during sealing phase 508C.

Figure 10D:
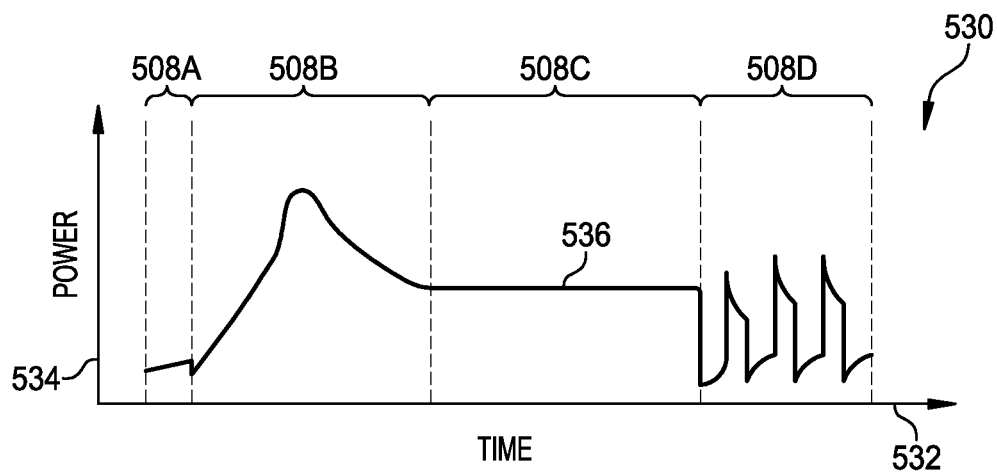

In FIG. 10D, graph 530 includes horizontal axis 532, vertical axis 534 and power/time relation 516. Horizontal axis 512 is indicative of time. Vertical axis 514 is indicative of real power of the tissue engaged by an electrosurgical instrument. Power/time relation 516 depicts measurements of power provided to engaged tissue taken at times indicated by horizontal axis 532. As shown in graph 530, power increases at the beginning of drying phase 508B, but then decreases at the end of drying phase 508B as the tissue resistance increases. During sticking-reduction phase 508D, power is substantially periodic with maxima that are greater than the power values obtained during sealing phase 508C. The power has peaks at the beginning of the maxima. These peaks of power correspond to the peaks in current that occur before liquid is driven from the engaged tissue.

Figure 11:
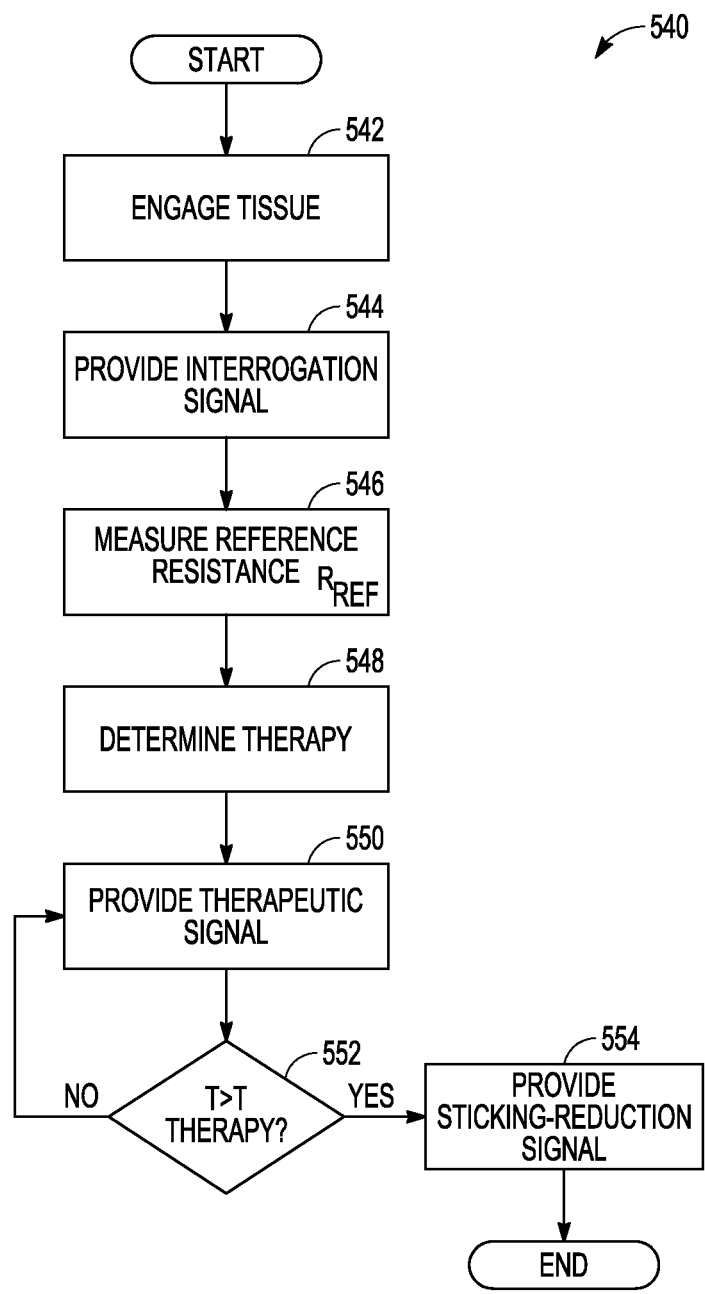
FIG. 11 is a flow chart of a method for reducing sticking between biological tissue and an electrosurgical instrument.

FIG. 11 is a flow chart of a method for reducing sticking between biological tissue and an electrosurgical instrument. In FIG. 11, method 540 begins at step 542, in which biological tissue is engaged by an electrosurgical instrument. Then, at step 544, control circuit 48 (depicted in FIG. 2) causes electrical-energy source 44 (depicted in FIG. 2) to provide an interrogation signal to the engaged biological tissue during an interrogation phase. Then, at step 546, control circuit 48 causes measurement circuit 46 (depicted in FIG. 2) to measure a reference tissue resistance $R_{REF}$. Then at step 548, a therapy time duration $T_{THERAPY}$ is determined based on the measured reference resistance $R_{REF}$.

At step 550, control circuit 48 causes electrical-energy source 44 to provide an electrotherapeutic signal to the engaged biological tissue during an electrotherapeutic phase. Then, at step 552, an elapsed therapy time $T_{ELAPSED}$ is compared with the therapy time duration $T_{THERAPY}$ determined at step 548. If, at step 552, the elapsed therapy time $T_{ELAPSED}$ is less than the determined therapy time duration $T_{THERAPY}$, then the method returns to step 550, where the electrotherapeutic signal is provided to the engaged biological tissue. If, however, at step 552, the elapsed therapy time $T_{ELAPSED}$ is greater than the determined therapy time duration $T_{THERAPY}$, then method 540 advances to step 554, where control circuit 48 causes electrical-energy source 44 to provide a pulsed sticking-reduction signal to the engaged biological tissue during a sticking reduction phase. After the sticking-reduction phase, the method ends. The pulsed sticking-reduction signal can be determined according to a sticking-reduction schedule. The sticking reduction schedule can be configured to reduce sticking, and in some examples to simultaneously provide additional tissue therapy.

Figure 12:
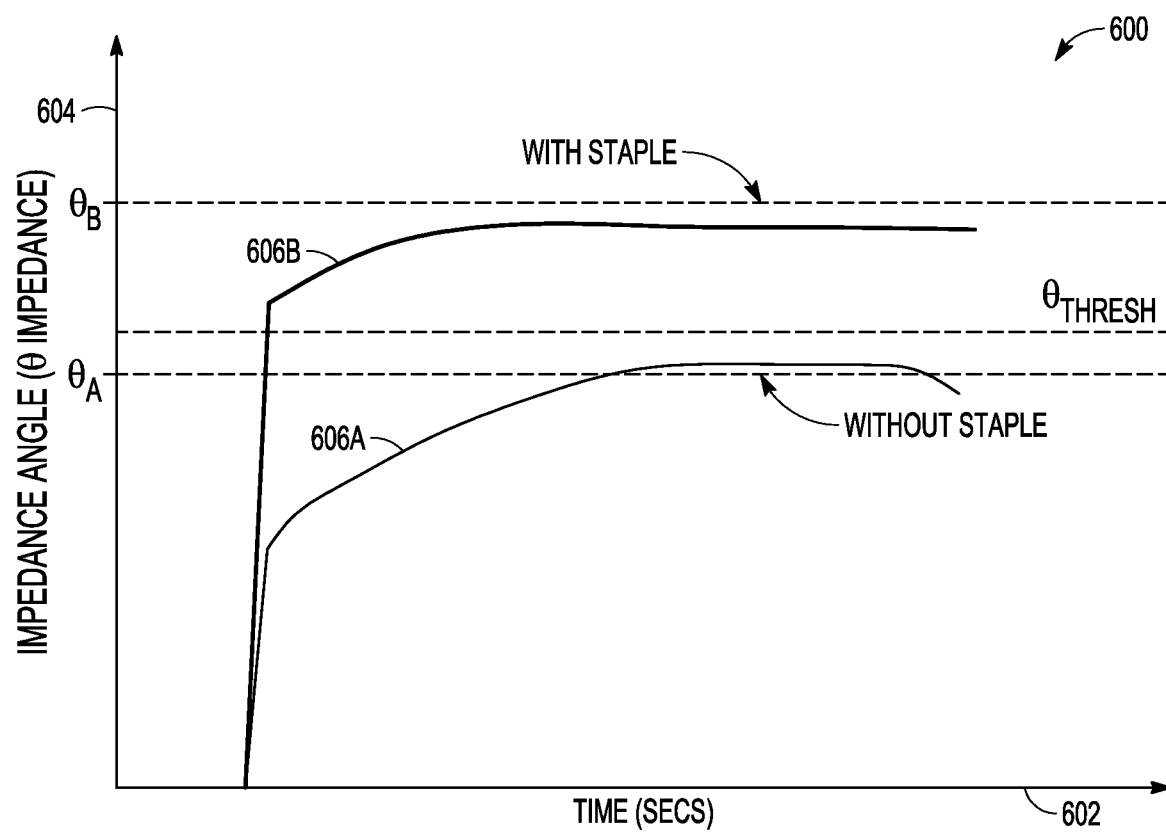
FIG. 12 is a graph depicting examples of impedance-angle/time relations of biological tissues with and without metal objects therein.
Figure 13:
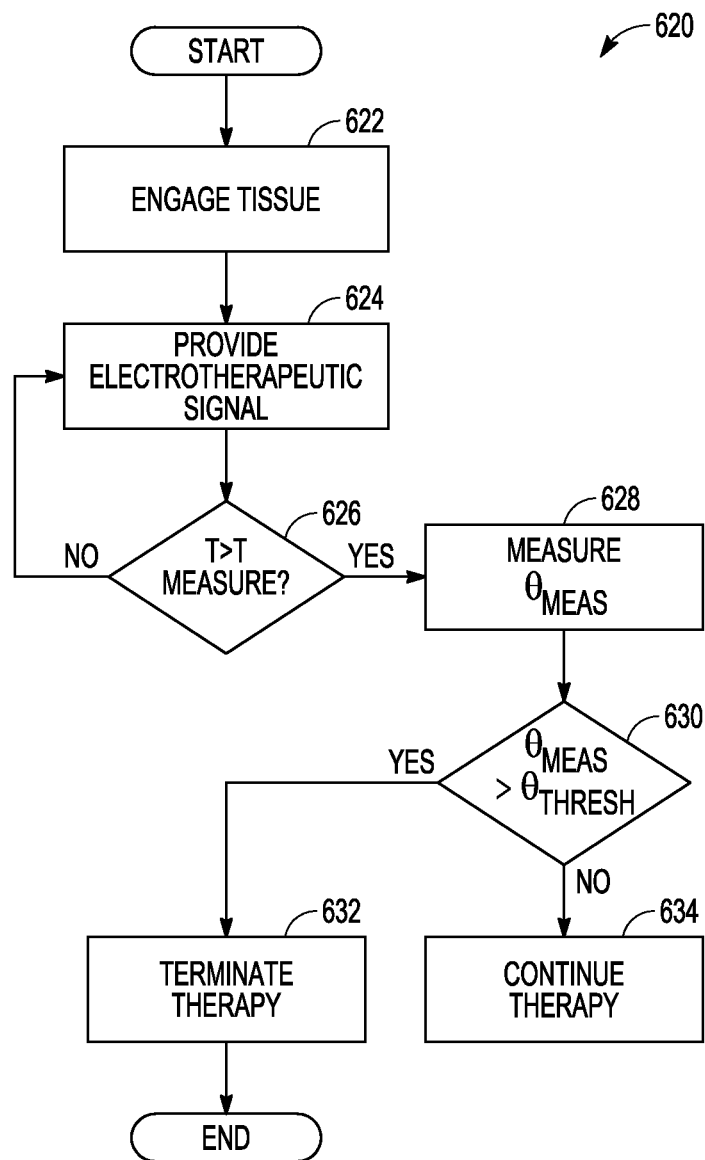
FIG. 13 is a flow chart of a method for determining presence or absence of a metal object in biological tissue engaged by an electrosurgical instrument.

Determining Presence or Absence of a Conductive Foreign Body in Biological Tissue Engaged by an Electrosurgical Instrument (FIGS. 12 and 13)

In various surgical procedures, artificial devices are implanted into a patient. For example, broken bones can be set with screws, bolts, shims, and other mechanical members. Staples can be used to maintain a desired arrangement of tissues that have been treated during surgery. Pacemakers and other electronic devices can be implanted into the patient for various purposes. Many of these artificial devices are or contain electrically conductive elements. Electrically conductive objects can interfere with electrosurgical procedures, should one be found in tissue engaged by the electrosurgical instrument.

Determining an environmental condition of the electrosurgical instrument, such as a presence or absence of a conductive foreign body within the engaged tissue before providing an electrotherapeutic signal to the engaged tissue, can prevent undesirable tissue modification. Presence or absence of a conductive foreign body in biological tissue engaged by an electrosurgical instrument can be determined based on angle of an impedance measurement of the engaged biological tissue. Therefore, interrogation of the angle of tissue impedance before an electrotherapeutic phase can prevent such undesirable tissue modification.

FIG. 12 is a graph depicting examples of impedance-angle/time relations of biological tissues with and without metal objects therein. In FIG. 12, graph 600 includes horizontal axis 602, vertical axis 604 and impedance-angle/time relations 606A-606B. Horizontal axis 602 is indicative of time. Vertical axis 604 is indicative of impedance angle of a biological tissue engaged by an electrosurgical instrument. Impedance-angle/time relations 606A-606B depicts measurements of an impedance angle taken during an electrotherapeutic phase at times indicated by horizontal axis 602. The impedance angle of the biological tissue is indicative of the ratio of a reactive component of the tissue impedance to the resistive component of the tissue impedance. For example, an impedance angle of −90° indicates purely capacitive tissue impedance, an impedance angle of +90° indicates purely inductive tissue impedance, and an impedance angle of 0° indicates purely resistive tissue impedance. In some examples, a measured reference impedance angle is substantially equal to an angular difference between a voltage across and current conducted by the engaged biological tissue as measured by a measurement circuit.

Impedance-angle/time relation 606A corresponds to a tissue in which no conductive foreign body is present. Impedance-angle/time relation 606B corresponds to a tissue in which a conductive foreign body is present. As shown in graph 600, both of impedance-angle/time relations 606A and 606B indicate the impedance angle changes during an initial or transient portion of the electrotherapeutic phase, and then remains substantially constant during the final or steady-state portion of the electrotherapeutic phase. The steady-state value of the impedance angles of impedance-angle/time relations 606A and 606B, however, differ from one another. Impedance-angle/time relation 606A indicates a steady-state value of impedance angle $\theta_A$ that is smaller than the steady-state value of impedance angle $\theta_B$ indicated by impedance-angle/time relation 606B.

Such a difference in impedance angles $\theta_A$ and $\theta_B$ can be used to determine presence or absence of a conductive foreign body within tissue engaged by an electrosurgical instrument. For example, a predetermined threshold value of impedance angle $\theta_{THRESH}$ can be compared with the measured impedance angle of the biological tissue. If the measured steady-state impedance angle is less than the predetermined angle threshold $\theta_{THRESH}$, as it is in impedance-angle/time relation 606A, then absence of a conductive foreign body can be determined. If, however, the measured steady-state impedance angle is greater than the predetermined angle threshold $\theta_{THRESH}$, as it is in impedance-angle/time relation 606B, then presence of a conductive foreign body can be determined. In response, a control circuit, such as the control circuit 48 of FIG. 2, can generate an error notification that indicates a presence of a conductive foreign body in the engaged biological tissue and reduce or terminate delivery of the therapeutic signal. However, if a similar impedance is identified without a steady state impedance angle greater than the predetermined threshold, than the control circuit can continue to allow delivery of the therapeutic signal. Energy can be applied and increased until boiling is detected. As resistance is low in this state, current would be at the high end of its typical value until boiling starts.

In some examples, impedance or resistance of the engaged biological tissue is measured during an interrogation phase. If the magnitude of the measured impedance or resistance of the engaged biological tissue is less than a predetermined resistance value, then the phase angle of the impedance will be determined and compared with the predetermined threshold $\theta_{THRESH}$.

In some examples, if the measured steady-state impedance angle is less than the predetermined angle threshold $\theta_{THRESH}$, as it is in impedance-angle/time relation 606A, then an open circuit can be determined. In response, the control circuit can generate an error notification that indicates an open circuit and can reduce or terminate the delivery of the therapeutic signal. In some examples, in response to the measured reference impedance angle being greater than a first angle, e.g., angle $\theta_A$, and less than a second angle, e.g., angle $\theta_B$, the control circuit can reduce a power level of the therapeutic signal. In some examples, the first angle can be about 70 degrees, which can be device dependent.

In this manner, the system can compare the measured reference impedance angle with the predetermined angle threshold $\theta_{THRESH}$ and generate a response indicative of an environmental condition of the instrument based on the comparison of the measured reference impedance angle with the angle threshold. The response can include a reduction in power and/or produce a signal indicative of the environmental condition. The response can include a notification signal, such as to indicate the condition to the user.

FIG. 13 is a flow chart of a method for determining presence or absence of a metal object in biological tissue engaged by an electrosurgical instrument. In FIG. 13, method 620 begins at step 622, in which biological tissue is engaged by an electrosurgical instrument. Then, at step 624, control circuit 48 (depicted in FIG. 2) causes electrical-energy source 44 (depicted in FIG. 2) to provide an electrotherapeutic signal to the engaged biological tissue during an electrotherapeutic phase. Then, at step 626, the elapsed therapy time T is compared with a predetermined time threshold $T_{MEASURE}$ at which time steady-state tissue impedance has been reached. If, at step 626, elapsed therapy time T is less than time threshold $T_{MEASURE}$, then method 620 returns to step 624 where the electrotherapeutic schedule continues.

If, however, at step 626, elapsed therapy time T is greater than time threshold $T_{MEASURE}$, then method 620 advances to step 628 where control circuit 48 causes measurement circuit 46 (depicted in FIG. 2) to measure impedance angle $\theta_{MEAS}$ of the engaged biological tissue. Then, at step 630, the measured impedance angle $\theta_{MEAS}$ of the engaged biological tissue is compared to a predetermined reference angle $\theta_{REF}$. If, at step 630, the measured impedance angle $\theta_{MEAS}$ is greater than the predetermined reference angle $\theta_{REF}$, then the control circuit can generate an error notification and the method 620 advances to step 632 where therapy is terminated. For example, the control circuit can generate an error notification that indicates a presence of a conductive foreign body in the engaged biological tissue.

In some examples, a predetermined range of reference angles (e.g., $\theta_{MIN} < \theta_{MEAS} < \theta_{MAX}$) can be used to determine whether a conductive foreign body is engaged by the electrosurgical instrument. If, however, at step 630, the measured impedance angle $\theta_{MEAS}$ is less than the predetermined reference angle $\theta_{REF}$, then method 620 advances to step 634, where therapy is continued.

The predetermined impedance angle that defines the border separating presence and absence of a conductive foreign body can vary depending on the particular electrosurgical instrument, the electrical parameters of the particular electrosurgical signal, the type of biological tissue, etc. For example, the frequency of the electrosurgical signal can be related to the impedance angle defining the presence/absence threshold.

Figure 14:
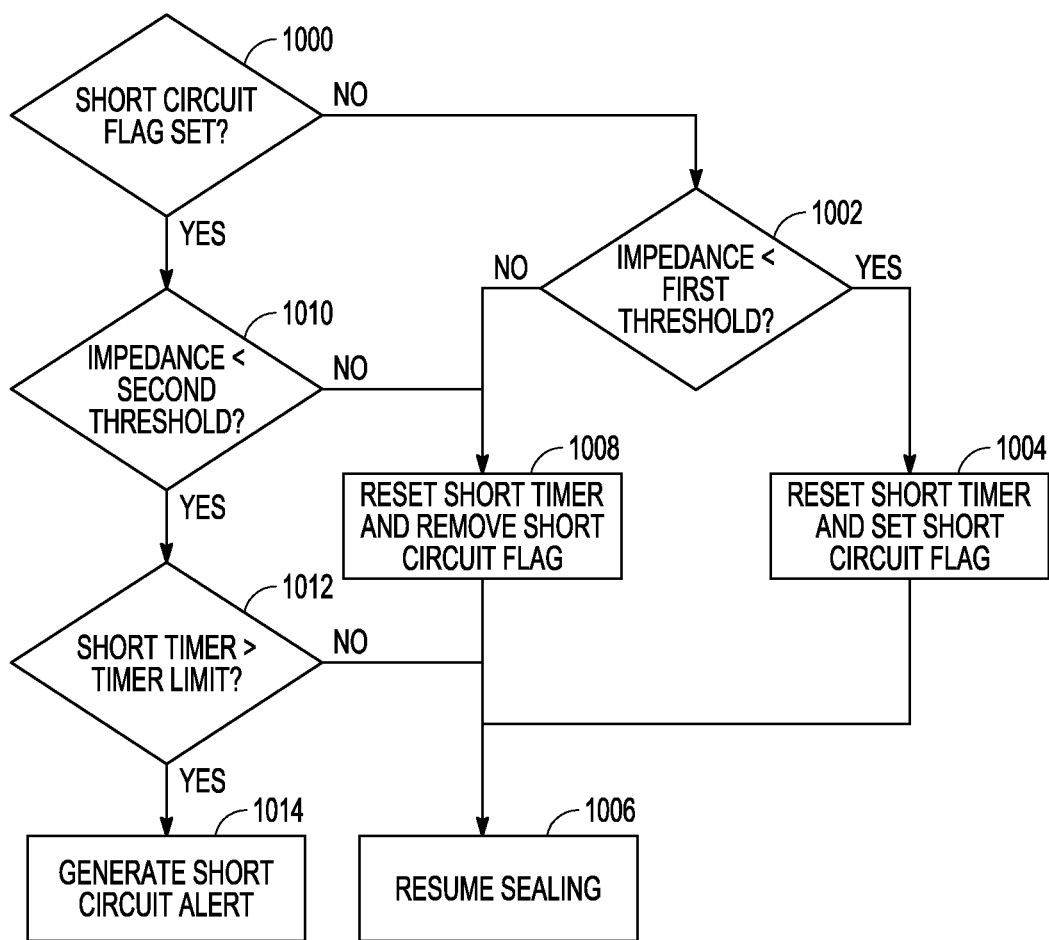
FIG. 14 is a flow diagram depicting an example of a two-boundary technique that can be used in a surgical system.

Short Circuit Error Trapping with Band Between Trigger and Escape Values (FIG. 14)

As described above, the electrosurgical generator, e.g., the electrosurgical generator 12 of FIG. 2, can coagulate or seal vessels or otherwise modify tissues through the application of electrical energy via electrotherapeutic signals. One of the problems with such energy application is that if electrodes coupled to or integrated with the electrosurgical instrument become shorted, the electrical energy passes predominately through the shorted area rather than through the tissue surrounding the shorted area. In such a case, the tissue is largely unaffected by the application of the electrical energy.

In one approach, insulated standoffs can be used to prevent opposing electrodes from contacting one another and energy being diverted through a contact point instead of through the tissue. However, electrically conductive elements can be found in surgery that, when grasped by the electrosurgical instrument, can result in a similar undesirable channeling of the energy. Examples of such elements include other surgical tools, metal clips, and staples.

In some systems, the electrosurgical generator can monitor for a specific (low) electrical impedance (referred to collectively as impedance) and can inform the user, e.g., surgeon or technician, that such undesired channeling of energy is currently occurring. If the electrosurgical generator determines such a low electrical impedance is present, the electrosurgical generator can start a timer and alert the user of the issue via audible and/or visual notifications, for example.

The electrosurgical generator can include a delay prior to any notification of an occurrence of low impedance to prevent other incidences of similar low impedances from falsely signaling a "true short circuit" incidence. Other incidences of low impedances can occur due to, for example, saline added at the surgical site, highly electrically conductive secretions (such as Gall bladder bile) or thin, moist tissue, such as abdominal omentum surrounding the kidney, especially when used with large electrical surface contact area electrodes.

When such environments are encountered, an extended application of energy can raise their electrical impedances by driving out fluid or converting fluids into gases through phase change. This is usually achieved within a set period of time, or the user is advised to dry the tip of the electrosurgical instrument and/or grasp the tissue in an alternative area, for example. Hence, it is preferable to gain an intended modified tissue by continuing to apply energy during this initial short condition when the cause is tissue derived and not a foreign object.

During the application of energy during a tissue-derived initial short circuit condition, a fluctuation in the impedance can occur in which the impedance increases sufficiently to exceed a short circuit trigger value but is still in a situation where the low impedance environment cannot be overcome by the power applied. In this situation, in place of a fairly rapid short circuit error, such as around three seconds, the energy can be applied until other times are reached such as no tissue effect or maximum activation time errors are met. However, this can extend the procedure, which can frustrate the user and create a negative user experience. Applying a filter to this situation can only do so much as a more positive indicator of driving out of the low impedance environment is more valuable.

The present inventors have recognized the desirability of providing a system having an improved indication of whether a low impedance environment short has been overcome or whether small increases (followed by decreases) in the environmental impedance has been achieved. These improvements can be particularly desirable in some systems, such as systems where the ability to measure and act upon the impedance feedback is less accurate. For example, a system can suffer from inaccuracy as a result of its inability to attain accurate impedance readings due to the low voltage applied during low impedance situations, which can result in greater difficulty in detecting phase angle shift caused by the system's inherent inductive nature as well as the inductance created by the material between the devices jaws.

The present inventors have recognized that a two-boundary threshold can be used to provide an improved indication of whether a low impedance environment short has been overcome or whether small increases (followed by decreases) in the impedance has been achieved. As described in more detail below, the system can monitor for two impedance values: a trigger value and an escape value. The system can use a first impedance value (a "trigger" value) to trigger a short circuit and the system can use a second impedance value (an "escape" value) greater than the first impedance value to exit an error clock timing routine.

The present inventors have recognized that a clinician can be locally boiling fluid, which can create bubbles that have an impedance. At this point, there is an apparent increase in the impedance that can push the impedance reading above the first impedance value but not necessarily out of a short circuit condition. The present inventors have recognized that a second impedance value can be important because it ensures that the system is drying out the tissue during a waiting time. By using the two-boundary threshold techniques of this disclosure, a short circuit condition can be quickly communicated to the user, thereby allowing the procedure to continue more quickly than using other techniques.

FIG. 2, described above, depicts an example of a surgical system that can be used to implement various aspects of the two-boundary threshold techniques of this disclosure. As shown in FIG. 1, the surgical system of FIG. 1 can include an electrosurgical device such as the forceps 14. The forceps 14 can include two jaws, e.g., the first jaw member 36 and the second jaw member 38. In some examples, one of the two jaws can be moveable, and the other jaw can be stationary. In other examples, both jaws can be moveable.

It should be noted that the two-boundary threshold techniques of this disclosure are not limited to electrosurgical devices that include jaws. Rather, the two-boundary threshold techniques can be implemented using devices such as spatulas and snares.

The electrosurgical device, e.g., the forceps 14, can include two or more electrodes sized, shaped, and/or otherwise configured to deliver the electrotherapeutic signal to the biological tissue, e.g., the tissue 16 of FIG. 1. In some examples, the electrodes can be integral with the jaws, e.g., the first jaw member 36 and the second jaw member 38, as in FIG. 1. In other examples, the electrodes can be coupled to the jaws.

An output circuit, such as including the power source 44 of FIG. 2, can be configured to generate and deliver electrosurgical energy to an output terminal, e.g., the instrument interface 42 of FIG. 2, for delivery to a patient. The output terminal can be configured to couple to an electrosurgical device, such as the forceps 14 of FIG. 1, and deliver electrosurgical energy, e.g., high frequency, such as RF energy, to biological tissue vie electrotherapeutic signals.

A control circuit of the surgical system, e.g., the control circuit 48 of the surgical system of FIG. 1, can be coupled to the output circuit and the control circuit can be configured to perform various aspects of the two-boundary threshold techniques. For example, a user, such as a surgeon or clinician, can initiate ongoing delivery of electrosurgical energy to the biological tissue of a patient, such as tissue positioned between two jaws of the electrosurgical device. In some examples, a processor, e.g., the processor 54 of the control circuit 48 of FIG. 2, can control a measurement circuit, e.g., the measurement circuit 46 of FIG. 2, to measure a first impedance value of the tissue in conducive communication with the two electrodes of the electrosurgical device, e.g., the forceps 14 of FIG. 1. In some examples, the tissue can be positioned between two electrodes of the electrosurgical device The processor can compare the first measured impedance value of the tissue to a first threshold value, e.g., the trigger value. In a non-limiting example for purposes of illustration, the trigger value can be about 5 ohms. When the first measured impedance value is less than or equal to the first threshold value, the processor e.g., the processor 54 of the control circuit 48 of FIG. 2, can initiate a short circuit timer, such as included in the processor. In a non-limiting example for purposes of illustration, a time limit of the timer can be about 3,000 milliseconds (ms) to about 6,000 ms.

The processor can control the measurement circuit to measure a second impedance value of the tissue positioned between the two electrodes of the electrosurgical device. Then, the processor can compare the second measured impedance value of the tissue to a second threshold value, e.g., the escape value, where the second threshold value (the escape value) is greater than the first threshold value (the trigger value). In a non-limiting example for purposes of illustration, the escape value can be about 10 ohms.

The trigger and escape values are representative of typical values but are not absolute and can depend on many factors, such as the impedance within the device, the exposed contact area, the ability of the processor to measure from feedback the impedance values, and the cable length of the attached device, among other factors. The trigger and escape values can be tuned or adjusted for various systems. In addition, the value of the timer limit can be tuned or adjusted and can depend on a manufacturer's understanding of surgeon perception and willingness to wait to see if a short error will be indicated or a longer period of power application (waiting) is preferred.

When the second measured impedance value is less than the second threshold value and the timer has not met the time limit, the surgical system can continue the delivery of electrosurgical energy. However, when the second measured impedance value is less than the second threshold value and the timer has met the time limit, the control circuit can control the output circuit to reduce or terminate the delivery of electrosurgical energy. In some examples, the control circuit can increase the power or current limit or both for a short period of time to continue the delivery of energy to overcome the wet environment. In some examples, when the timer has met the time limit, the surgical system can generate an indication to a user. For example, a user interface, e.g., the user interface 50 of the surgical system of FIG. 2, can generate one or both of an audible indication and a visual indication to the user to indicate that the delivery of the electrosurgical energy has been reduced or terminated.

The delivery of energy can occur during an interrogation phase in which the amount of energy delivered is low, but not zero. For example, during an interrogation phase, the energy delivered is not sufficient to effect tissue.

In some examples, the control circuit can be configured to adjust at least one of the first threshold value (the trigger value), the second threshold value (the escape value), and the time limit based on at least one characteristic of the electrosurgical device. For example, current density can affect the amount of power of the delivered electrotherapeutic signal, which can affect the amount of energy the system delivers to the biological tissue. As an example, the surface area of the electrodes of the electrosurgical device can affect the current density. For example, for an electrosurgical device having a large surface area and a low power electrosurgical generator, there can be insufficient current to quickly burn off liquids in the tissue. As such, it can be desirable for the system to wait for a longer period of time before reducing or terminating the delivery of energy to the tissue. To that end, the control circuit can adjust at least one of the first threshold value (the trigger value), the second threshold value (the escape value), and the time limit using the surface area of the electrode(s). For example, the control circuit can retrieve various one or more parameters of the electrosurgical device stored in a memory device, where the one or more parameters can include the surface area of the electrode(s) associated with the electrosurgical device.

In addition, a jaw force of the electrosurgical device can affect the current density. For example, a stronger jaw force can increase the amount of tissue in contact with the electrodes, which can affect the boiling point of the tissue. As such, the control circuit can adjust at least one of the first threshold value (the trigger value), the second threshold value (the escape value), and the time limit for electrosurgical devices with a greater jaw force. An electrosurgical device, such as the forceps 14 of FIG. 1, can include a jaw force sensor configured to sense a jaw force, where the jaw force sensor is in communication with a control circuit, such the control circuit 48 of FIG. 2.

In addition to characteristics of the electrosurgical device, at least one of the first threshold value (the trigger value), the second threshold value (the escape value), and the time limit can be procedure dependent. For example, some procedures and/or tissues are more wet than others. As an example, hepatic procedures can involve significant blood from the liver. In some procedures, the clinician can introduce significant fluid to clean tissue. As such, it can be desirable during some procedures for the system to wait for a longer period of time before terminating the delivery of energy to the tissue. To that end, in some examples, the control circuit can adjust at least one of the first threshold value (the trigger value), the second threshold value (the escape value), and the time limit to allow the electrosurgical generator additional time to burn off excess fluid, if needed.

Alternatively, or in addition to, the characteristic(s) of the electrosurgical device can be used to adjust the threshold values or time limit. For example, the output current of the electrosurgical generator can affect the amount of power of the delivered electrotherapeutic signal, which can affect the amount of energy the system delivers to the biological tissue. In some examples, based on the output current, for example, the control circuit can adjust at least one of the first threshold value (the trigger value), the second threshold value (the escape value), and the time limit to allow the electrosurgical generator additional time to burn off excess fluid, if needed.

In some examples, the two-boundary threshold techniques of this disclosure can be used during an initial tissue interrogation phase at the beginning of the procedure. In other examples, the techniques can be used partway through the procedure, such as during the heating or drying phases.

For purposes of explanation, non-limiting examples of a system with and without the escape value will now be described. Initially, a clinician can press an activation button and energy is attempted to be delivered to electrosurgical device, e.g., to the jaw. But, due to the highly conductive nature of the saline and blood washing over the electrosurgical device, the electrosurgical generator identifies that the impedance is 4 ohms and a short circuit timer begins.

For a system without an escape value, the electrosurgical generator can provide energy and at 1,000 ms of applied energy time, through the short circuit timer, a bubble is created, e.g., at the device jaw, which increases the impedance to 6 ohms. The bubble is transitionary, but because the impedance is now above a 5-ohm threshold, the short circuit timer is reset and the electrosurgical generator starts its 3,000 ms countdown again.

The transitionary bubble can appear a number of times, but it can be knocked away from the jaw again and again, resetting the short circuit timer each time, until eventually another alarm, such as an extended activation time alarm, is triggered, such as between about 12,000 ms to about 30,000 ms. The clinician can become frustrated by this experience and realize that they have to extract some of the surrounding saline or grasp the tissue differently to achieve a good seal.

For a system without an escape value, as described above, the electrosurgical generator can provide energy and at 1,000 ms of applied energy time, through the short circuit timer, a bubble is created, e.g., at the device jaw, which can increase the impedance to 6 ohms. However, because an escape value, e.g., 10 ohms, is needed to exit the short circuit loop, the short circuit timer continues. Another bubble is created that can again increase the impedance to 6 ohms, which is again ignored by the short circuit timer because the impedance has not met the escape value, or the upper boundary requirement. At 3,000 ms the short circuit alarm is presented to the clinician and the clinician now knows that either the fluid must be removed, or the tissue grasped in a different way. This reaction is much quicker due to the upper boundary "escape" value of the 10 ohms, allowing the procedure to continue more quickly.

The two-boundary threshold techniques described above can also be incorporated into other systems that utilize short circuit triggers. For example, if the trigger value is met, then the system, while waiting to see if the short circuit timer or the escape value will be met first, can also interrogate the feedback to determine and interpret the phase angle at that point in time. If the phase angle is above a particular threshold, then the system can determine that the frequency of phase angle, coupled with the low impedance, indicates that a metal object is inadvertently (or otherwise) grasped by the electrosurgical device. The system can continue monitoring the phase angle until the upper escape value has met or the short circuit timer, e.g., 3,000 ms, is met.

FIG. 14 is a flow diagram depicting an example of the two-boundary technique described above. At block 1000, a processor, e.g., the processor 54 of the control circuit 48 of FIG. 2, can determine whether a short circuit flag is set. If the short circuit flag is not set ("NO" branch of block 1000), the processor can compare a measured impedance to a first impedance threshold, e.g., a 5-ohm threshold, at decision block 1002.

If the processor determines that the impedance is less than the first threshold ("YES" branch of block 1002), then the processor resets the short circuit timer and sets the short circuit flag at block 1004 and sealing can resume at block 1006. If the processor determines that the impedance is not less than the first threshold ("NO" branch of block 1002), then the processor resets the short circuit timer and removes the short circuit flag at block 1008 and sealing can resume at block 1006.

However, if the short circuit flag is set ("YES" branch of block 1000), the processor can compare a measured impedance to a second impedance threshold, e.g., a 7-ohm threshold, at decision block 1010. If the processor determines that the impedance is not less than the second threshold ("NO" branch of block 1010), then the processor resets the short circuit timer and resets the short circuit flag at block 1008 and sealing can resume at block 1006. If the processor determines that the impedance is less than the second threshold ("YES" branch of block 1010), then the processor can compare the short circuit timer to a timer limit, e.g., 3000 ms, at block 1012.

If the processor determines that the short circuit timer is greater than the timer limit ("YES" branch of block 1012), then the processor can generate a short circuit alert, e.g., audible and/or visual notification, to notify the user at block 1014. If the processor determines that the short circuit timer is not greater than the timer limit ("NO" branch of block 1012), then sealing can resume at block 1006.

In this manner, if the impedance is less than the first impedance threshold, e.g., 5 ohms, consistently for a duration of at least that defined by the short circuit timer, e.g., 3000 ms, a short-circuit alert can be generated and the electrotherapeutic signal will be reduced or terminated. There can be a hysteresis between the first and second impedance thresholds, e.g., 5 ohms and 7 ohms, such that a timer, e.g., having a 3000 ms timer limit, will be started when the impedance falls below the first threshold, e.g., 5 ohms, and reset when the measured impedance rises above the second threshold, e.g., 7 ohms.

Figure 15:
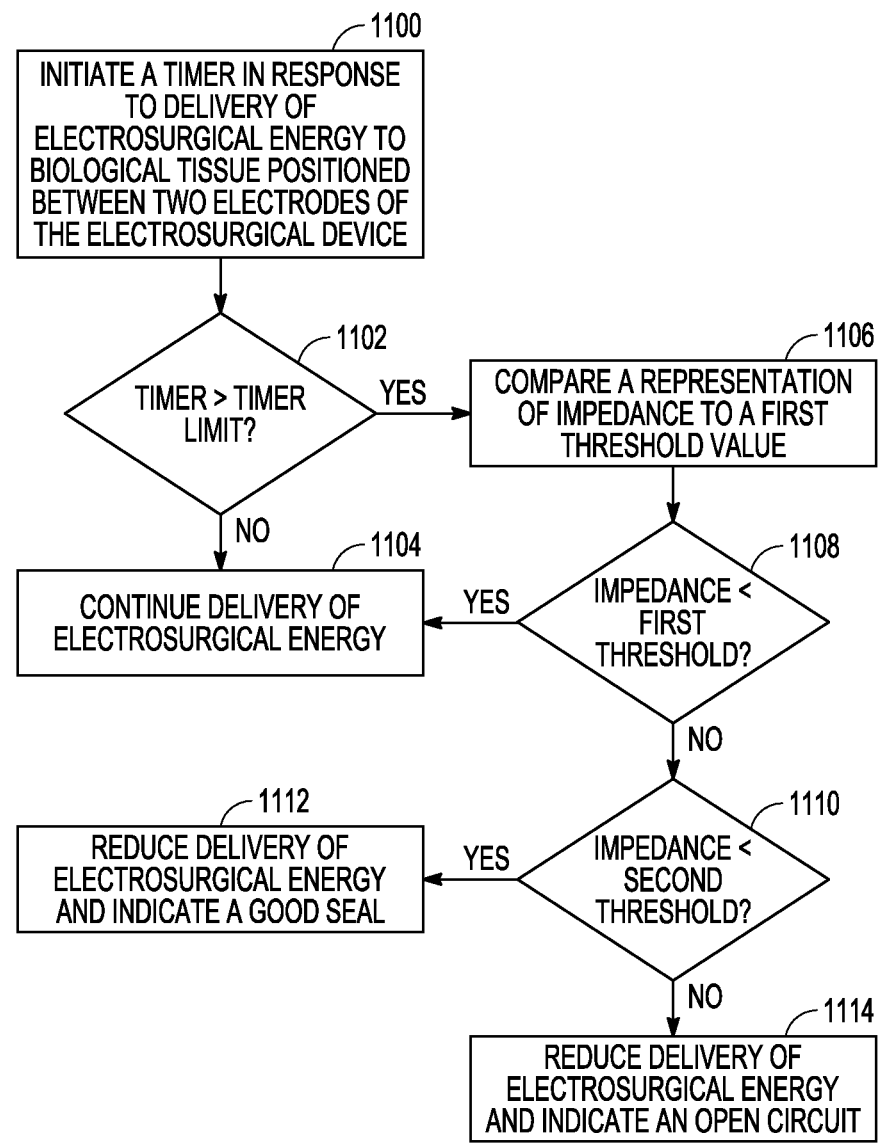
FIG. 15 is a flow diagram depicting an example of open circuit check techniques that can be used in a surgical system.
Figure 16:
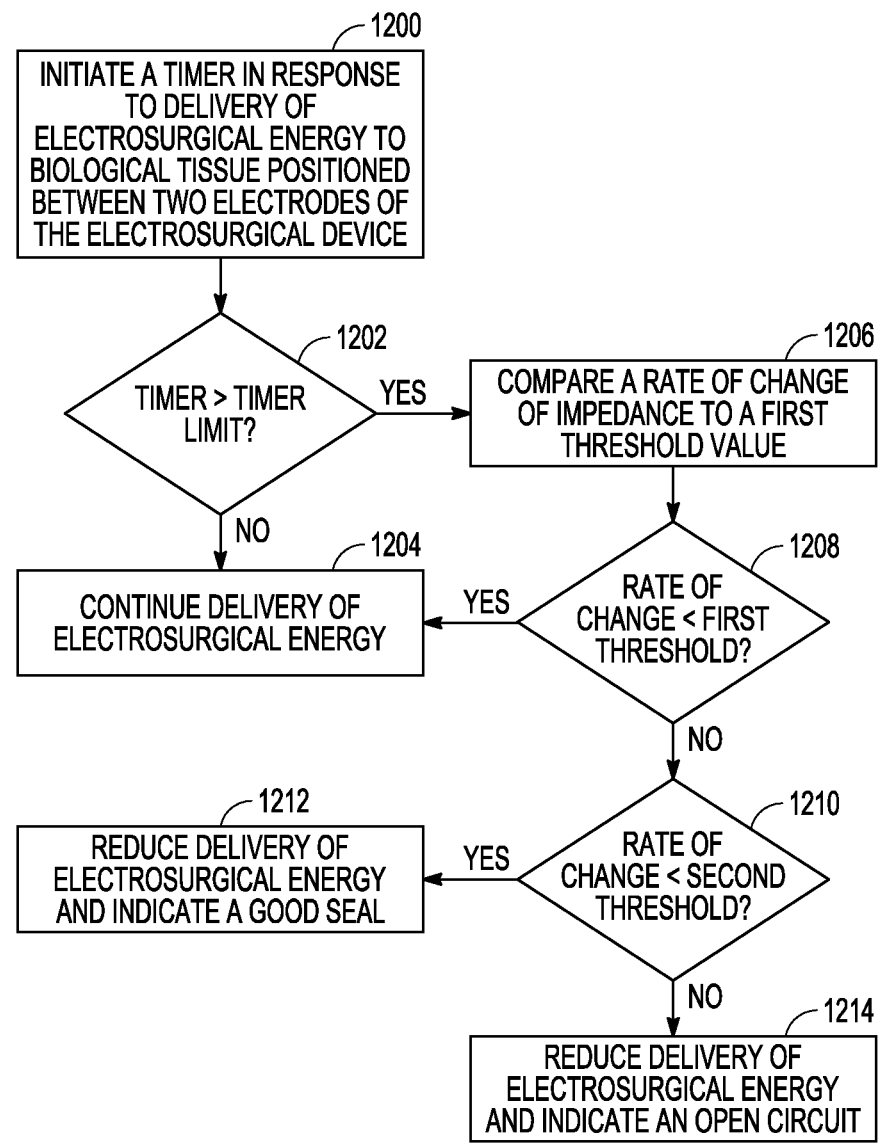
FIG. 16 is a flow diagram depicting another example of the open circuit check techniques that can be used in a surgical system.

Open Circuit Check for Impedance Limit Endpoint Waveform (FIGS. 15 and 16)

RF vessel sealing devices often use either a fixed maximum impedance value, such as to indicate that the tissue is appropriately affected, or an impedance delta to detect when the tissue has been adequately affected. Impedance can also be used to identify if the device jaws have been opened during activation. For example, the system can attempt to detect an impedance above a set point to identify an "open circuit," which signifies that the jaws are open.

In some cases, however, opening the jaws during activation can result in a "false positive" in which the generator signals a good seal but, in reality, the user has just opened the device jaws. For example, with the system monitoring for a "good seal" end point, e.g., of 350 ohms, and an "open circuit" error value, e.g., of 2000 ohms, the system can react in this false positive way during activation. The user controls application of energy to the tissue and the system can monitor for both the endpoint and the open circuit. In a correct activation, the energy application can initially lower the impedance, e.g., from 30 ohms to 15 ohms, and then can raise the impedance of the tissue as the energy dries out the tissue. The energy rise can meet the endpoint value of 350 ohms and the generator can stop applying power and send a signal to the user indicating that the seal is complete.

In another example, the user controls application of energy to tissue and the energy application can initially lower the impedance of the tissue, e.g., from 30 ohms to 15 ohms, and then the impedance starts to rise. During this rise period, the user slowly (or rapidly) opens the jaws. The impedance value can increase rapidly, passing first through the required 350-ohm boundary, at which time the system turns off the power and reports a good seal. Because the energy is turned off (and continued energy application can create a "sticky tissue to jaw" situation if a greater than 350-ohm tissue situation is created) and the impedance will not reach the "open circuit" error value of 2000 ohms, the system erroneously reports a good seal.

The present inventors have recognized the need to include an open circuit check that begins with initiating a timer when a user initiates an ongoing delivery of electrosurgical energy to biological tissue. When the timer reaches a timer limit (or "times out"), the system can determine the impedance value and determine if the impedance value represents an open circuit. If the impedance value does represent an open circuit, the system can reduce or terminate delivery of energy and, if not, the system can allow continued application of energy until the impedance meets an endpoint value.

Using the proposed timer techniques, an electrosurgical generator, e.g., electrosurgical generator 12 of FIG. 2, can apply energy to the system and to biological tissue in contact with an electrosurgical device, such between the jaws of the forceps 14 of FIG. 1. A processor, e.g., the processor 54 of the control circuit 48 of FIG. 2, system can set a timer, e.g., 50-100 ms, when the control circuit has determined that the tissue is ready to be driven to a final impedance end point value or impedance delta value.

When the timer "times out", a measurement circuit, e.g., the measurement circuit 46 of FIG. 2, to measure an impedance value. The processor can determine whether the measured impedance represents an open circuit and energy delivery should be reduced or terminated, or whether the measured impedance is below an open circuit value and energy delivery can continue until the impedance meets the required endpoint value. By using these techniques, there is a minimum period of time in which neither the endpoint value nor an open circuit value can be achieved but depending on the impedance measured at the end of this period, the processor can decide whether to flag an "open circuit" error and reduce or terminate delivery of energy or continue delivering energy to the complete seal cycle endpoint impedance value.

Several possible scenarios will now be described that can occur using the open circuit check techniques. In a first scenario, the user applies energy to the tissue, e.g., between the jaws of the electrosurgical device, and the impedance of the tissue decreases and then increases. The processor can recognize that the tissue is suitably affected and can then start the timer. After a time limit, e.g., 50 ms, the impedance is below the "open circuit" value, e.g., an absolute value of 2000 ohms or an impedance delta value, but is also below the target tissue endpoint value (or an impedance delta value). As such, the processor continues to control the application of power until the target endpoint value is achieved. The processor terminates application of power and indicates to the user that a good seal has been achieved.

In some examples, a rate of change of impedance can be a triggering variable. For example, if the impedance rate of change exceeds a preset value, the generator can report an open circuit and then modify the energy output (or terminate or significantly reduce).

In a second scenario, the user applies energy to the tissue, e.g., between the jaws of the electrosurgical device, and the impedance of the tissue decreases and then increases. The processor can recognize that the tissue is suitably affected and can start the timer. After a time limit, e.g., 50 ms, the impedance is below the "open circuit" value, e.g., an absolute value of 2000 ohms or an impedance delta value, but the tissue is at or greater than the tissue endpoint value, e.g., 350 ohms. The processor terminates application of power and indicates to the user that a good seal has been achieved.

In a third scenario, the user applies energy to the tissue, e.g., between the jaws of the electrosurgical device, and the impedance of the tissue decreases and then increases.

The processor can recognize that the tissue is suitably affected and can then start the timer. The user releases the tissue prematurely, e.g., by opening the device jaws, and the impedance increases rapidly through the endpoint value, then through the open circuit value, e.g., an absolute value of 2000 ohms or an impedance delta value. After 50 ms, for example, the processor can determine that the impedance is in excess of the open circuit value, terminate application of power, and indicate an incomplete seal "open circuit" error message to the user.

The duration of the timer can be important to the success of correctly identifying an open circuit and a good seal. If the duration is too long, small amounts of tissue can rapidly reach impedance values greater than the open circuit value, such as when the user is attempting to affect thin fascia material on the internal wall of the pelvic cavity. Although such tissue is typically initially very electrically conductive, the fluid content can rapidly boil and the impedance of a portion of such thin material, e.g., within the device jaws, leads to a rapidly rising impedance. If the timer duration is 200 ms, for example, a good seal or tissue modification of a thin fascia material on the internal wall of the pelvic cavity, would lead to an error message, rather than an appropriate good seal tone.

If the timer is too short, a false positive is possible. For example, if the timer is set to 10 ms, then the following scenario can occur. The user applies energy to tissue and the impedance decreases and then increases. As the impedance increases, the processor determines that the tissue is ready to be driven to the endpoint and starts the timer. If the jaws are opened slowly, an impedance ramp rate of the jaws does not meet the open circuit value within the 10 ms and therefore the control circuit continues applying energy. As the impedance continues toward the open circuit value of 2000 ohms, for example, the impedance value passes through the 350-ohm endpoint value and stops applying power, incorrectly giving a good seal tone at the end.

The value of the timer, the endpoint impedance, and the open circuit impedance can depend on a number of factors such as the following (alone or in combination): 1) the amount of power being applied to the tissue at the time (and may be either a set power or a power that takes into consideration the power and adjusts the timer and or the impedance values accordingly); 2) the target tissue (prior power feedback can provide an indication of the type of tissue between the jaw and predict the likely or expected impedance ramp rate and adjust the timer and or the impedance value accordingly; and 3) the surface area of the electrodes and or the force that the electrode jaws apply in their fully closed position.

Using the open circuit check techniques described in more detail below, the electrosurgical system, e.g., the system 10 in FIG. 2, can set a timer, e.g., 50 ms-100 ms, when the tissue is ready to be driven to an endpoint value (of a seal). When the timer reaches a limit and "times out", the system can measure the impedance (or a rate of change with respect to time of impedance) and determine whether the value represents an open circuit condition or whether to allow continued application of energy until the impedance meets the endpoint value, which indicates a good seal. In this way, there is a minimum period of time in which neither the endpoint value nor an open circuit value can be achieved. But, depending on the impedance determined at the end of the timer, the system can determine whether to continue to a complete seal cycle endpoint value or indicate that an open circuit is present.

FIG. 15 is a flow diagram depicting an example of the open circuit check techniques described above that can be used in a surgical system. As shown in FIG. 1, the surgical system of FIG. 1 can include an electrosurgical device such as the forceps 14. The forceps 14 can include two jaws, e.g., the first jaw member 36 and the second jaw member 38. In some examples, one of the two jaws can be moveable and the other jaw can be stationary. In other examples, both jaws can be moveable.

It should be noted that the open circuit check techniques of this disclosure are not limited to electrosurgical devices that include jaws. Rather, the open circuit techniques can be implemented using devices such as spatulas and snares.

The electrosurgical device, e.g., the forceps 14, can include two or more electrodes sized, shaped, and/or otherwise configured to deliver the electrotherapeutic signal to the biological tissue, e.g., the tissue 16 of FIG. 1. In some examples, the electrodes can be integral with the jaws, e.g., the first jaw member 36 and the second jaw member 38, as in FIG. 1. In other examples, the electrodes can be coupled to the jaws.

An output circuit, such as including the power source 44 of FIG. 2, can be configured to generate and deliver electrosurgical energy to an output terminal, e.g., the instrument interface 42 of FIG. 2, for delivery to a patient. The output terminal can be configured to couple to an electrosurgical device, such as the forceps 14 of FIG. 1, and deliver electrosurgical energy, e.g., high frequency, such as RF energy, to biological tissue vie electrotherapeutic signals. A control circuit of the surgical system, e.g., the control circuit 48 of the surgical system of FIG. 1, can be coupled to the output circuit and the control circuit can be configured to perform various aspects of the open circuit check techniques.

Referring now to FIG. 15, at block 1100, the control circuit can initiate a timer when a user, such as a surgeon or clinician, initiates an ongoing delivery of electrosurgical energy to biological tissue positioned between two electrodes of the electrosurgical device. In some examples, the timer can be included in the processor, such as in the processor 54 in FIG. 2. In some examples, the control circuit can set the timer when the control circuit has determined that the tissue is ready to be driven to a final impedance end point value (or impedance delta value). In some examples, a processor, e.g., the processor 54 of the control circuit 48 of FIG. 2, can control a measurement circuit, e.g., the measurement circuit 46 of FIG. 2, to measure an impedance value of the tissue positioned between two electrodes of the electrosurgical device, e.g., the forceps 14 of FIG. 1.

At block 1102, the processor can determine whether the timer is greater than the timer limit, e.g., 50 ms-100 ms. If the timer has not exceeded the time limit ("NO" branch of block 1102), then system can continue the delivery of electrosurgical energy at block 1104. If the timer has met the time limit ("YES" branch of block 1102), then the processor can compare a representation of the measured impedance to a first threshold value (the endpoint value), e.g., 250-350 ohms, at block 1106. The first threshold value can be stored in memory, such as in memory 56 in FIG. 2.

At block 1108, if the processor determines that the representation of the measured impedance is less than the first threshold value ("YES" branch of block 1108) (the endpoint value), then the processor can continue the delivery of electrosurgical energy. If the processor determines that the representation of the measured impedance is not less than the first threshold value ("NO" branch of block 1108), then the processor can compare a representation of the measured impedance to a second threshold value (the open circuit value), e.g., 2000 ohms, at block 1110. The second threshold value can be stored in memory, such as in memory 56 in FIG. 2.

If the processor determines that the representation of the measured impedance is less than the second threshold value ("YES" branch of block 1110), then the processor can reduce or terminate the delivery of electrosurgical energy at block 1112. Here, the measured impedance is greater than the first threshold value (the endpoint value) and less than the second threshold value (the open circuit value), which indicates that a good seal has been achieved. In some examples, the control circuit can generate a notification to the user to indicate a good seal.

If the processor determines that the representation of the measured impedance is not less than the second threshold value ("NO" branch of block 1110), then the processor can reduce or terminate the delivery of electrosurgical energy at block 1114. Here, the measured impedance is greater than the first threshold value (the endpoint value) and also equal to or greater than the second threshold value (the open circuit value), which indicates that there is an open circuit. In some examples, the surgical system can generate an indication to the user to indicate an open circuit. For example, a user interface, e.g., the user interface 50 of the surgical system of FIG. 2, can generate one or both of an audible indication and a visual indication to the user to indicate that the delivery of the electrosurgical energy has been reduced or terminated and an open circuit was detected.

As indicated above, in some examples a processor, e.g., the processor 54 of the control circuit 48 of FIG. 2, can control a measurement circuit, e.g., the measurement circuit 46 of FIG. 2, to measure the impedance value of the tissue and the processor can determine whether a representation of the measured impedance exceeds a threshold value. In some examples, the representation of impedance includes a value of the impedance, such as an absolute value of impedance. In other examples, the representation of impedance includes a change with respect to time in the value of the impedance (or "delta"), such as a first derivative of impedance with respect to time.

FIG. 5 is a flow diagram depicting another example of the open circuit check techniques described above that can be used in a surgical system. In the method 300, at block 302, the control circuit can initiate a timer at the beginning of Phase 3. At block 304, the control circuit can apply electrosurgical energy to biological tissue positioned between two electrodes of the electrosurgical device. At block 306, the control circuit can determine whether an endpoint is met. If the control circuit determines that an endpoint has not been met ("NO" branch of block 306), then the control circuit can return to block 304 and continue to apply electrosurgical energy to the biological tissue. However, if the control circuit determines that an endpoint has been met ("YES" branch of block 306), then the method proceeds to block 308.

At block 308, the control circuit can determine whether an elapsed time is less than or equal to a timer limit. If the control circuit determines that the elapsed time is less than or equal to a timer limit ("YES" branch of block 308), then the control circuit can reduce the delivery of electrosurgical energy and indicate an open circuit at block 310. If the control circuit determines that the elapsed time is not less than or equal to a timer limit ("NO" branch of block 308), then the control circuit can reduce the delivery of electrosurgical energy and indicate a good seal is present at block 312.

FIG. 16 is a flow diagram depicting another example of the open circuit check techniques described above that can be used in a surgical system. FIG. 16 is similar to FIG. 15 except that in FIG. 16 the control circuit can compare a rate of change of impedance with respect to time of the biological tissue, e.g., 40 kiloohms per second, to a threshold value.

Referring now to FIG. 16, at block 1200, the control circuit can initiate a timer in response to a delivery of electrosurgical energy to biological tissue positioned between two electrodes of the electrosurgical device. In some examples, the timer can be included in the processor, such as in the processor 54 in FIG. 2. In some examples, the control circuit can set the timer when the control circuit has determined that the tissue is ready to be driven to a final impedance end point value (or impedance delta value). In some examples, a processor, e.g., the processor 54 of the control circuit 48 of FIG. 2, can control a measurement circuit, e.g., the measurement circuit 46 of FIG. 2, to measure an impedance value of the tissue positioned between two electrodes of the electrosurgical device, e.g., the forceps 14 of FIG. 1.

At block 1202, the processor can determine whether the timer is greater than the timer limit, e.g., 50 ms-100 ms. If the timer has not exceeded the time limit ("NO" branch of block 1202), then system can continue the delivery of electrosurgical energy at block 1204. If the timer has met the time limit ("YES" branch of block 1202), then the processor can compare a rate of change with respect to time of the measured impedance to a first threshold value (the endpoint value) at block 1206. The first threshold value can be stored in memory, such as in memory 56 in FIG. 2. A non-limiting example of a rate can be 2000 ohms over a time period of 50 ms, or 40,000 ohms/s.

At block 1208, if the processor determines that the rate of change of the measured impedance is less than the first threshold value ("YES" branch of block 1208)(the endpoint value), then the processor can continue the delivery of electrosurgical energy at block 1204. If the processor determines that the rate of change of the measured impedance is not less than the first threshold value ("NO" branch of block 1208), then the processor can compare the rate of change of the measured impedance to a second threshold value (the open circuit value) at block 1210. The second threshold value can be stored in memory, such as in memory 56 in FIG. 2.

If the processor determines that the rate of change of the measured impedance is less than the second threshold value ("YES" branch of block 1210), then the processor can reduce or terminate the delivery of electrosurgical energy at block 1212. Here, the rate of change is greater than the first threshold value (the endpoint value) and less than the second threshold value (the open circuit value), which indicates that a good seal has been achieved. In some examples, the control circuit can generate a notification to the user to indicate a good seal.

If the processor determines that the rate of change of the measured impedance is not less than the second threshold value ("NO" branch of block 1210), then the processor can reduce or terminate the delivery of electrosurgical energy at block 1214. Here, the rate of change is greater than the first threshold value (the endpoint value) and also equal to or greater than the second threshold value (the open circuit value), which indicates that there is an open circuit. In some examples, the surgical system can generate an indication to the user to indicate an open circuit. For example, a user interface, e.g., the user interface 50 of the surgical system of FIG. 2, can generate one or both of an audible indication and a visual indication to the user to indicate that the delivery of the electrosurgical energy has been terminated and an open circuit was detected.

By using the open circuit check techniques described above, the system can provide fewer erroneous good seal indications.

Figure 17:
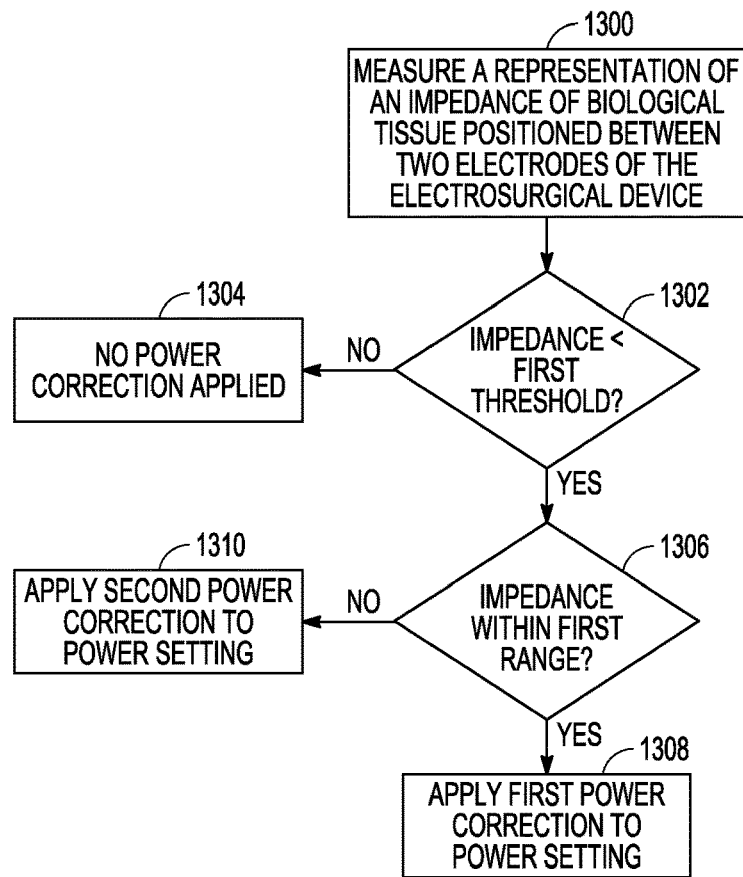
FIG. 17 is a flow diagram depicting an example of power correction techniques that can be used in a surgical system.

Alternate Power Correction Outputs in Low Accuracy Hardware Systems (FIG. 17)

Electrosurgical generators are constantly evolving with new "state of the art" hardware that allows the generators to be ever more accurate and responsive to the feedback from the tissues that they intend to modify. The improvement in hardware architecture can provide many benefits over their less advanced or historical counterparts, such as providing greater CPU speed, which can allow faster responses in collecting, analyzing, and reacting to data, as well as new functionality that permit phase angle calculations, for example, which can provide more accurate indications of feedback-based derived data such as power delivery, impedance, etc.

There is often a desire to gain the performance of new "state of the art" hardware with existing hardware that is already placed in the hospital, providing the same performance to the user with this older placed capital equipment rather than having to update to new capital equipment. Such performance improvements can be important in some electrosurgical applications to ensure the best possible tissue modification performance for the patient.

For example, appropriate power delivery can be important in providing optimal tissue performance in vessel sealing. Too much energy delivered too quickly can result in tissue damage from steam pockets within the tissue. Slow application of energy can significantly extend procedure times and result in longer periods in which the patient is under anesthesia, which can result in reduced benefits of surgical outcomes and higher risk of patient recovery issues. From a competitive standpoint, quick tissue modification with a high level of confidence of resultant correct tissue effect can be central to having a market acceptable device.

Many older electrosurgical systems may not have the ability to accurately measure the phase angle of the RF output. During the sealing process, the variation of the tissue grasped between the jaws and its interaction with the inherent inductance and capacitance in the output circuit can cause phase angle changes in the RF waveform. Calculations of power and load resistance can be inaccurate if this phase angle is not considered and therefore measuring this parameter can increase the accuracy of the system.

When the voltage ("E") leads the current ("I"), helpfully remembered with the mnemonic "ELI", the load is considered to be inductive. When the current ("I") leads the voltage ("E"), helpfully remembered with the mnemonic "ICE", the load is considered to be capacitive. In either the "ELI" or "ICE" scenario, the outcome of a phase angle offset is a reduction in actual power delivery compared to the apparent power delivery that the electrosurgical generator believes it is providing due to the misalignment of the peaks of the current and voltage.

The accuracy of the voltage applied can further compound the issue. The accuracy of voltage application of older systems can become difficult as the voltage decreases—especially when the voltage has been created to control high rates intended for monopolar outputs, e.g., 4000V or higher, which are then applied to bipolar outputs that can go as low as tens of volts or less. This can result in hardware manufacturers creating "tuned hardware" that is tuned for accuracy within certain impedance and voltage ranges within which devices are typically required to work, with expected phase shifts. In lower ranges of impedance, the accuracy of the calculated power delivery can become very difficult due to voltage levels being so low.

As an example, to supply a specific power, e.g., 100 W, a system supplies a current (I) at a voltage (V) to meet the power requirement. The impedance determines the makeup of the voltage and the current to deliver the required power. For example, if the impedance is 5 ohms, then the electrosurgical generator can provide a 4.5 A output at 22.22V.

As another example, if the same system attempts to deliver 30 W (31.25 W) into an impedance of 5 ohms, then the electrosurgical generator can provide approximately a 2.5 A output at 12.5V. Consider this 12.5V output on a system set to provide as much as 4000V in some cases. A typical impedance range for which older electrosurgical systems become less accurate is about 0-50 ohms. For such an impedance range, an older electrosurgical system can struggle to apply enough current to burn off fluid in the tissue to provide a good seal because the electrosurgical generator's power output is not sufficiently accurate.

The present inventors have recognized the need to improve the power control in legacy electrosurgical systems. To solve this need, the present inventors have recognized that applying a power correction at lower impedance values can improve the power control in legacy electrosurgical systems and overcome their lack of accuracy.

As shown in FIG. 1, the surgical system of FIG. 1 can include an electrosurgical device such as the forceps 14. The forceps 14 can include two jaws, e.g., the first jaw member 36 and the second jaw member 38. In some examples, one of the two jaws can be moveable, and the other jaw can be stationary. In other examples, both jaws can be moveable.

It should be noted that the power correction techniques of this disclosure are not limited to electrosurgical devices that include jaws. Rather, the power correction techniques can be implemented using devices such as spatulas and snares.

The electrosurgical device, e.g., the forceps 14, can include two or more electrodes sized, shaped, and/or otherwise configured to deliver the electrotherapeutic signal to the biological tissue, e.g., the tissue 16 of FIG. 1. In some examples, the electrodes can be integral with the jaws, e.g., the first jaw member 36 and the second jaw member 38, as in FIG. 1. In other examples, the electrodes can be coupled to the jaws.

An output circuit, such as including the power source 44 of FIG. 2, can be configured to generate and deliver electrosurgical energy to an output terminal, e.g., the instrument interface 42 of FIG. 2, for delivery to a patient. The output terminal can be configured to couple to an electrosurgical device, such as the forceps 14 of FIG. 1, and deliver electrosurgical energy, e.g., high frequency, such as RF energy, to biological tissue vie electrotherapeutic signals. A control circuit of the surgical system, e.g., the control circuit 48 of the surgical system of FIG. 1, can be coupled to the output circuit and the control circuit can be configured to perform various aspects of the power correction techniques.

FIG. 17 is a flow diagram depicting an example of power correction techniques that can be used in a surgical system. At block 1300, a measurement circuit, e.g., the measurement circuit 46 of FIG. 2, to measure a representation of an impedance of the tissue positioned between two electrodes of the electrosurgical device, e.g., the forceps 14 of FIG. 1. In some examples, the control circuit can measure a central tendency, such as a mean, median, mode, or other central tendency, during a portion of the output, such as during the last 50 ms of output, and store these values, such as in the memory 56 of FIG. 2.

At block 1302, the control circuit can compare the measured representation of impedance to a first threshold, e.g., about 50 ohms, stored in memory, such as the memory 56 of FIG. 2. The first threshold, e.g., 50 ohms, can be based on an impedance value below which a power correction is needed for an electrosurgical system. The first threshold can be adjusted based on the electrosurgical system.

If the impedance is not less than the first threshold ("NO" branch of block 1302), then the impedance is high enough that the control circuit does not need to apply a power correction to the power control of the electrosurgical generator, as shown at block 1304. The electrosurgical system can apply power via a normal operation.

However, if the impedance is less than the first threshold ("YES" branch of block 1302), then the control circuit can apply a power correction to the power control of the electrosurgical generator. For example, as shown at block 1306, the control circuit can determine whether the measured impedance is within a first range of impedances, e.g., 0-100 ohms. If the measured impedance is within the first range of impedances ("YES" branch of block 1306), then the control circuit can select a first power correction associated with the first range of impedances and apply the selected first power correction at block 1308.

If the measured impedance is not within the first range of impedances ("NO" branch of block 1306), then the control circuit can select a second power correction associated with a second range of impedance, e.g., 20-100 ohms, when the representation of the impedance is within the second range, e.g., 20-100 ohms, and apply the selected second power correction at block 1310. As an example, the 'desired power' can be 100 W, but the system can actually be measuring only 50 W. The correction factor can be applied to the measured value to ensure correct compensation is applied to the output.

The electrosurgical system can apply the power corrections using a linear calculation, such as the following equation:

$$\text{Corrected Power} = (((Z_{load} \times A) + B) \times \text{MeasuredPower})/1000 \qquad \text{Equation (1)}$$

where Zload is the measured impedance of the tissue, A and B are specific power correction values or parameters that can be selected to provide different possible power correction trajectories, and MeasuredPower is the power that the electrosurgical system believes it is providing to the tissue (V×I). The processor, e.g., the processor 54 of FIG. 2, can retrieve the A and B parameters from memory, e.g., memory 56 of FIG. 2, and calculate a corrected power setting using Equation (1) above. In a first non-limiting example for purposes of explanation only, a first calculation of a power correction for 10 ohms can use a value of 11 for A and 548 for B. In a second non-limiting example for purposes of explanation only, a first calculation of a power correction for 50 ohms can use a value of 11 for A and 419 for B.

Using the corrected power setting, the control circuit can deliver electrosurgical energy via the electrodes of the electrosurgical device. In some examples, the control circuit can reduce or terminate the application of the selected power correction to the power setting when the representation of impedance meets or exceeds a threshold value. Continuing with the example described above, the control circuit can initially apply a power correction for a measured impedance of 15 ohms, which is below 50 ohms and within the first range of 0-20 ohms, and reduce or terminate the application of that power correction when the measured impedance exceeds 20 ohms, which is above the upper limit of the first range. In some examples, the control circuit can begin applying a new power correction based on the change in impedance. Continuing with the example described above, for a measured impedance of 21 ohms, which is below 50 ohms and within the second range of 20-50 ohms, the control circuit can apply a new power correction to the power setting.

In some examples, rather than having a single impedance value, e.g., 20 ohms, be the difference between the first range, e.g., 0-20 ohms, and the second range, e.g., 20-50 ohms, it can be desirable for the control circuit to use hysteresis to prevent the system from oscillating between two power corrections. When implemented, hysteresis can dynamically change the threshold limits depending on the present 'state' of the system, which can prevent unintended oscillation between the at least two thresholds when the measured parameter is near the thresholds. It can influence one or both of the upper and lower portions of the thresholds. In this manner, the control circuit can dynamically adjust at least one of an upper limit and a lower limit of the first range when the representation of the impedance is within a predetermined percentage or value of the upper or lower limit.

For example, a specified percentage can be used at the boundaries of the ranges. As an example, for measured impedances within 20% of the 20 ohm upper limit of the first range, the control circuit can use can dynamically adjust, e.g., increase, one or both of the upper and lower limits associated with the first range.

In another example, rather than use a percentage for hysteresis, the control circuit can use a specified impedance value at the boundaries of the ranges. As an example, for measured impedances within 4 ohms of the 20 ohm upper limit of the first range, the control circuit can dynamically adjust, e.g., increase, one or both of the upper and lower limits associated with the first range.

It should be noted that although two non-limiting examples of ranges were described with two corresponding power corrections, in some examples, only one range can provide sufficient power correction. In other examples, more than two ranges with corresponding power corrections can be used.

The power correction techniques described above can significantly improve the power control of an electrosurgical system to artificially overcome the lack of accuracy. However, in some examples, a secondary parameter can be used to provide even more accuracy. For example, the power correction can be based on an output during a "tissue sampling" phase. If the tissue has one property, then a first power correction can be used. If the tissue has another property, then a second power correction can be used. Examples of properties that can be used to determine a power correction include, but are not limited to, the energy delivered over a period of time, calculated impedance, current draw, voltage phase angle, tissue temperature, and the like. The processor can use these properties alone or in combination to select a power correction. For example, the processor can use both a tissue temperature and a calculated impedance to select a power correction.

In examples that utilize one or more secondary parameters to determine a power correction, the measurement circuit can measure a representation of an impedance of the tissue positioned between two electrodes of the electrosurgical device, compare the measured representation of impedance to a first threshold, and if the impedance is less than a first threshold, e.g., 50 ohms, as described above with respect to FIG. 17, select a first power correction from two or more power corrections. Then, the control circuit can compare a representation of one or more secondary parameters to one or more thresholds.

When the representation of one (or more) secondary parameters is less than one (or more) thresholds, the control circuit can select between the previously selected first power correction and one or more other power corrections. The control circuit can determine that the previously selected first power correction is adequate or it can determine, based on the secondary parameter, e.g., output current of the power generator, a tissue temperature, and a voltage phase angle, that a different power correction would be desirable to apply to a power setting.

In some examples, if the impedance is less than a first threshold, e.g., 50 ohms, the control circuit can select the secondary power correction. As the impedance increases, the control circuit can then select the first power correction. As the increases continues to increase, the tuned power setting can utilize the standard generator control without any power correction.

In some examples, the power corrections can be used for specific periods of time, e.g., using tissue feedback. For example, using the corrected power setting, the control circuit can deliver electrosurgical energy via the electrodes of the electrosurgical device during a period of time over a range of impedance values or until an amount of energy is applied, or a combination of both. In addition, external metrics can be applied such as time periods or user settings.

Figure 24:
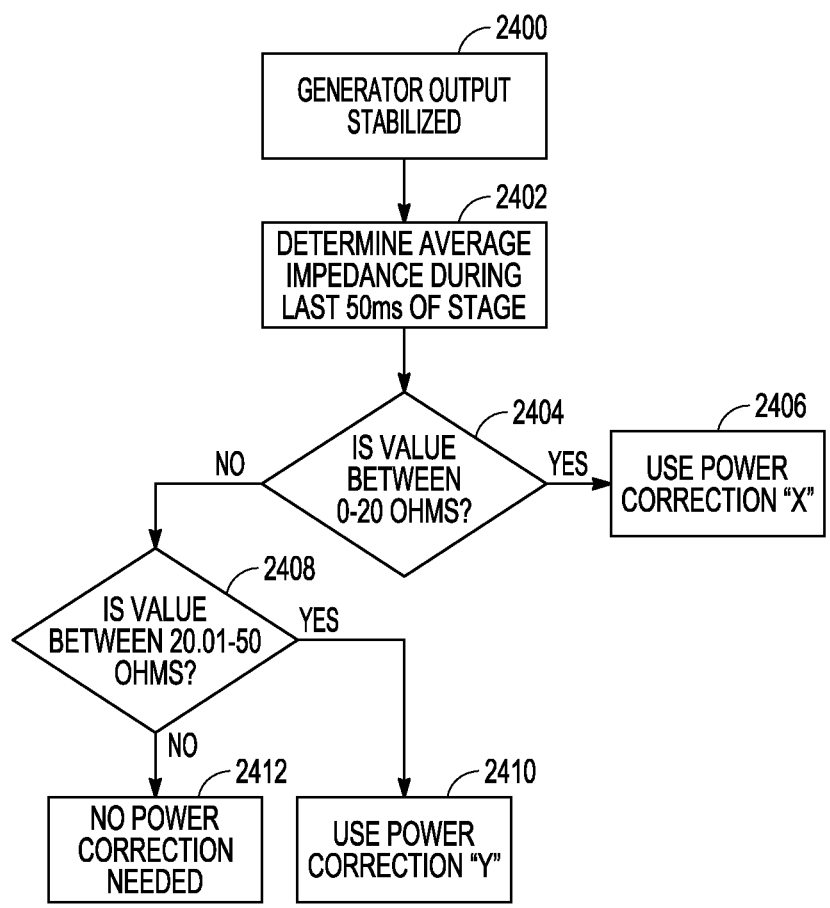
FIG. 24 is a flow diagram depicting another example of power correction techniques that can be used in a surgical system.

FIG. 24 is a flow diagram depicting another example of power correction techniques that can be used in a surgical system. FIG. 24 depicts a two-decision flow diagram that can use impedance to decide which power correction to apply. In addition, the flow diagram can also use impedance as a decision point for when to apply the power correction and when to stop applying the power correction.

At block 2400, stage 1A can be complete and the generator output can stabilize. At block 2402, stage 1B can begin and the control circuit can determine an average impedance of tissue during the last 50 ms of stage 1B. At block 2404, the control circuit can determine whether the average impedance is between 0-20 ohms. If the average impedance is between 0-20 ohms ("YES" branch of block 2404), then at block 2406 the control circuit can use a first power correction value "X" for stage 2.

If the average impedance is not between 0-20 ohms ("NO" branch of block 2404), then at block 2408 the control circuit can determine whether the average impedance is between 20.01-50 ohms. If the average impedance is between 20.01-50 ohms ("YES" branch of block 2408), then at block 2410 the control circuit can use a second power correction value "Y" for stage 2. If the average impedance is not between 20.01-50 ohms ("NO" branch of block 2408), then at block 2412 the control circuit can determine that no power correction is needed for stage 2.

Figure 18:
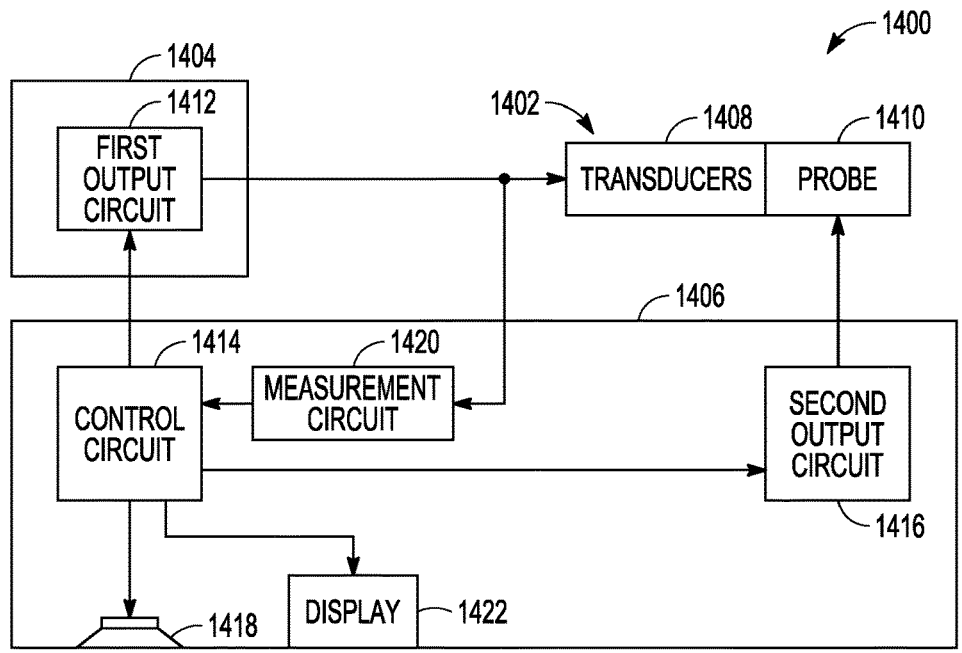
FIG. 18 is a simplified block diagram of an example of a combination ultrasonic energy and electrosurgical energy system that can implement various techniques of this disclosure.
Figure 19:
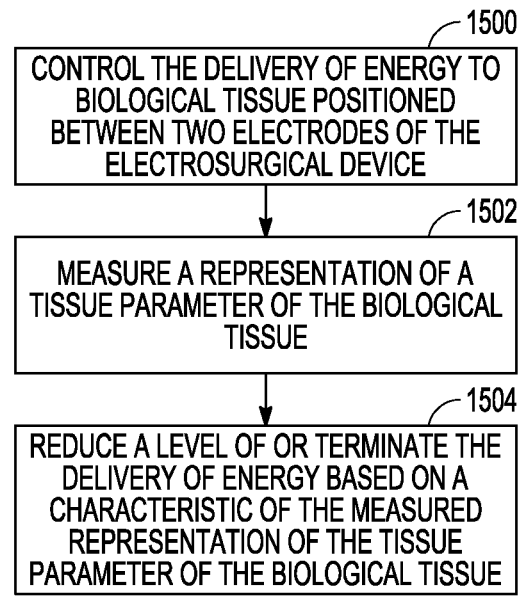
FIG. 19 is a flow diagram depicting an example of a reduced thermal margin technique that can be used in a combination ultrasonic energy and electrosurgical energy system.

Reduced Thermal Margin Combination Energy Device (FIGS. 18 and 19)

Surgical systems exist that can deliver two types of energy: ultrasonic energy and electrosurgical energy, such as high-frequency energy. The ultrasonic energy can provide rapid and precise cutting of tissue and the electrosurgical energy can provide reliable vessel sealing. The system can deliver the two types of energy simultaneously or the system can control the delivery such that the two types of energy are delivered separately.

FIG. 18 is a simplified block diagram of an example of a combination ultrasonic energy and electrosurgical energy system that can implement various techniques of this disclosure. The system 1400 can include a surgical device 1402 coupled to an ultrasonic drive unit 1404 and an electrosurgical drive unit 1406. Additional information regarding such combination ultrasonic energy and electrosurgical energy systems can be found in commonly assigned U.S. Pat. No. 8,574,228 to Okada et al. and titled "ULTRASOUND TREATMENT SYSTEM", the entire contents of which being incorporated herein by reference. The surgical device 1400 can include ultrasonic transducer 1408 and a probe 1410. The ultrasonic drive unit 1404 can include a first output circuit 1412 configured to generate a driving signal that is applied to the ultrasonic transducers 1408 to generate ultrasonic vibrations that are conveyed to biological tissue via probe 1402.

The system 1400 can include a control circuit configured to control various aspects of the operation of the ultrasonic drive unit 1404 and the electrosurgical drive unit 1406. For example, the control circuit 1414 can be configured to generate and apply signals to the first output circuit 1412 of the ultrasonic drive unit 1404 and configured to generate and apply signals to a second output circuit 1416 of the electrosurgical drive unit 1406. In some example configurations, the control circuit 1414 can include components similar to and operate similar to the control circuit 48 of FIG. 2. In some example configurations, the electrosurgical drive unit 1406 can include components similar to and operate similar to the electrosurgical generator 12 of FIG. 2. The second output circuit 1416 can generate high frequency electrotherapeutic signals to be delivered to biological tissue via the probe 1410. The first and second output circuits 1412, 1416 are coupled to the control circuit 1414 and configured to generate and deliver energy to an output terminal of the system for delivery to a patient. In some examples, the system can include a speaker 1418 and/or display 1422 to provide an alarm or other audible notification and/or a visual notification to a user.

In some examples, the surgical device 1402 can be similar to the surgical device FIG. 1 of commonly assigned U.S. Patent Application Publication No. US 20120010539 to Yachi et al. and titled OPERATION DEVICE AND SURGICAL APPARATUS," the entire contents of which being incorporated herein by reference. The surgical device of FIG. 1 of U.S. Patent Application Publication No. US 20120010539 can perform a treatment such as incision, resection, and the like of the living tissue by utilizing the ultrasonic waves together with the application of the high-frequency waves. In addition, it is also possible to perform a coagulation treatment of the living tissue by utilizing the ultrasonic waves.

In some examples, the electrosurgical drive unit 1406 can include a measurement circuit 1420. The measurement circuit 1420 can be similar to the measurement circuit 46 of FIG. 2 and can be configured to measure one or more electrical parameters of biological tissue coupled to the surgical device 1402.

Appropriate power delivery can be an important factor to gaining optimal tissue performance in vessel sealing. Too much energy too quickly can cause steam pockets to form within the tissue, which can cause damage to tissue surrounding the surgical device. This phenomenon is often termed "thermal margin". Combination ultrasonic energy and electrosurgical energy systems often use waveforms such as a constant pulse rate or ramped output of high frequency energy, e.g., RF energy, along with ultrasonic energy and layer them on top of each other. This can result in undesirable consequences, such as surgical device tips getting hot and thermal margins increasing.

The present inventors have recognized the need in a combination ultrasonic energy and electrosurgical energy system to monitor feedback from the tissue to determine whether a desirable steam pocket has been created. Using various techniques described below, the combination ultrasonic energy and electrosurgical energy system can monitor feedback from the tissue, such as a change in the current drawn, a change in the impedance value, or a change in the impedance over time, to provide an indication that a desirable steam pocket has been created. At this point, instead of continuing to apply energy to the tissue, one or both of the high frequency energy, e.g., RF energy, and the ultrasonic energy can be reduced or stopped.

A non-limiting specific example of using a combination ultrasonic energy and electrosurgical energy system, e.g., the system 1400 of FIG. 18, to modify biological tissue using various techniques of this disclosure will now be described. The combination ultrasonic energy and electrosurgical energy system can deliver at least two modes of energy: a first mode including ultrasonic energy and second mode including bipolar energy. A control circuit, e.g., the control circuit 1414 of FIG. 18, can monitor feedback from the tissue in contact with the surgical device by controlling a measurement circuit, e.g., the measurement circuit 1420 of FIG. 18, to measure a representation of an impedance of the tissue. For example, the control circuit can monitor a change in the impedance value, which can indicate that a maximum preferable amount of steam has been created in the tissue and further steam creation could lead to excessive thermal margin. In other example implementations, the control circuit can monitor a change in the current drawn, and/or an impedance value, e.g., an absolute impedance value.

Once the change in impedance values meets or exceeds a threshold value, the control circuit can control the ultrasonic drive unit, e.g., the ultrasonic drive unit 1404 of FIG. 18, to stop the ultrasonic output. In addition, the control circuit can control the electrosurgical drive unit, e.g., the electrosurgical drive unit 1406 of FIG. 18, to reduce the output of the high frequency electrotherapeutic signals generated by the second output circuit 1416 of the electrosurgical drive unit 1406. For example, the high frequency output can be reduced to such an extent that the generated steam in the tissue can partially or totally revert back to liquid. Once this liquid state is achieved, as determined by the control circuit using a set time, feedback control, or both, the system 1400 can apply power again, until such time, either the steam production limit is met, or the end of an energy application cycle is met, e.g., either by user decision or by feedback control.

FIG. 19 is a flow diagram depicting an example of a reduced thermal margin technique that can be used in a combination ultrasonic energy and electrosurgical energy system. At block 1500, a control circuit can control the delivery of energy to biological tissue positioned between two electrodes of the electrosurgical device, where the delivered energy includes at least some ultrasonic energy. For example, the control circuit 1414 of FIG. 18 can control the first output circuit 1412 to deliver ultrasonic energy and the second output circuit 1416 to deliver high frequency energy, e.g., RF energy, to tissue in contact with the surgical device 1402 of FIG. 18. As an example, the surgical device can include an ultrasonic forceps with HF electrodes on its jaws.

At block 1502, a measurement circuit can measure a representation of a tissue parameter, such as an impedance, of the biological tissue. For example, the measurement circuit 1420 of FIG. 18 to measure a change in the current drawn, and/or an impedance value, such as an absolute impedance value or a change in impedance (a relative value).

At block 1504, the control circuit can reduce a level of or terminate the delivery of energy based on a characteristic of the measured representation of the tissue parameter, of the biological tissue. Example characteristics can include but are not limited to the following: resistance, impedance, current, phase angle, consumed current, and/or required voltage, as well as changes (deltas) in one or more of these characteristics, and combinations of these characteristics. For example, the control circuit 1420 of FIG. 18 can control the first output circuit 1412 of FIG. 18 to reduce the level of ultrasonic energy. In some examples, the control circuit 1420 can control the first output circuit 1412 to terminate, or reduce, the delivery of ultrasonic energy. Termination is an example of a reduction of the delivery of ultrasonic energy.

In some examples, the delivered energy can be modified, such as by increasing the energy or by temporarily reducing it but allowing it to return to its previous level after a short interval. Temporarily reducing the energy can mean temporarily reduce to, or near to, no energy delivery, e.g., suspend.

In some examples, the control circuit can pause the delivery of energy to allow for steam condensing, in contrast to a pause in the energy as an endpoint to the activation. By pausing the delivery of energy, the system can establish a fluid condensation dwell time. The system does not need to monitor the tissue parameters to identify the endpoint of a joint high frequency/ultrasound therapy pulse.

In other examples, the control circuit 1420 can control the first output circuit 1412 to reduce the level of electrosurgical energy. In some examples, the control circuit 1420 can control the first output circuit 1412 to terminate the delivery of electrosurgical energy.

The electrosurgical energy can be power-controlled or voltage-controlled, for example, as described above. In a power-controlled implementation, the control circuit 1420 can control the second output circuit 1416 to deliver, e.g., according to a plan, regimen, or schedule, the electrosurgical energy using a product of the voltage applied across the engaged biological tissue and the electrical current output by second output circuit 1416. For example, the control circuit can control the second output circuit 1416 to deliver a constant power or a monotonically increasing power during a particular phase, e.g., drying phase.

In a voltage-controlled implementation, the control circuit can control the voltage of the electrosurgical energy delivered by the second output circuit 1416, e.g., according to a plan, regimen, or schedule. For example, the control circuit can control the second output circuit 1416 to deliver a constant voltage or a monotonically increasing voltage during a particular phase, e.g., drying phase.

As mentioned above, the control circuit can reduce a level of or terminating the delivery of energy based on a characteristic of the measured representation of impedance of the biological tissue. In some examples, the characteristic of the measured representation of impedance is an impedance value, such as an absolute value of impedance or a relative value. In some such examples, the control circuit can be configured to compare the measured impedance value to a threshold value and reduce the level of or terminate the delivery of energy based on the comparison. For example, the control circuit can reduce the level of, periodically reduce the level of, or terminate the delivery of one or both of the ultrasonic energy and electrosurgical energy based on the comparison. By periodically reducing the level, the system can reduce the power at various stages during a single output, where an output is during the course of a full activation.

In other examples, the characteristic of the measured representation of impedance is a change in impedance value. In some such examples, the control circuit can be configured to compare the change in impedance value to a threshold value and reduce the level of or terminate the delivery of energy based on the comparison. For example, the control circuit can reduce the level of or terminate the delivery of one or both of the ultrasonic energy and electrosurgical energy based on the comparison.

Using the techniques described above for a combination ultrasonic energy and electrosurgical energy system, the overall power output of the system can be reduced when steam pockets are created, which can reduce undesirable thermal margins.

Figure 20:
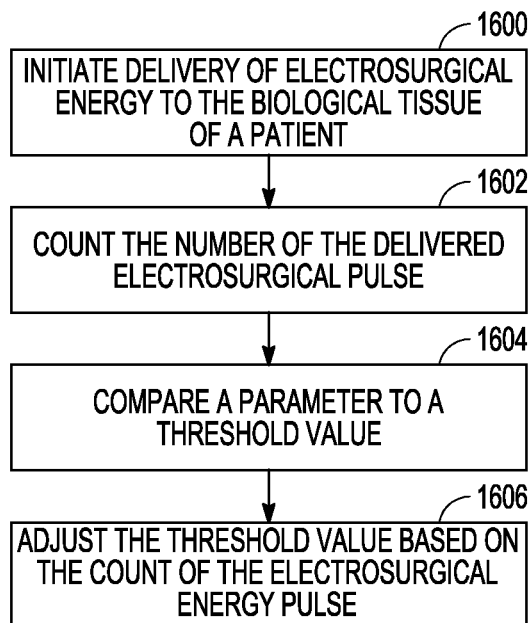
FIG. 20 is a flow diagram depicting an example of a thermal margin control technique that can be used in an electrosurgical system.
Figure 21:
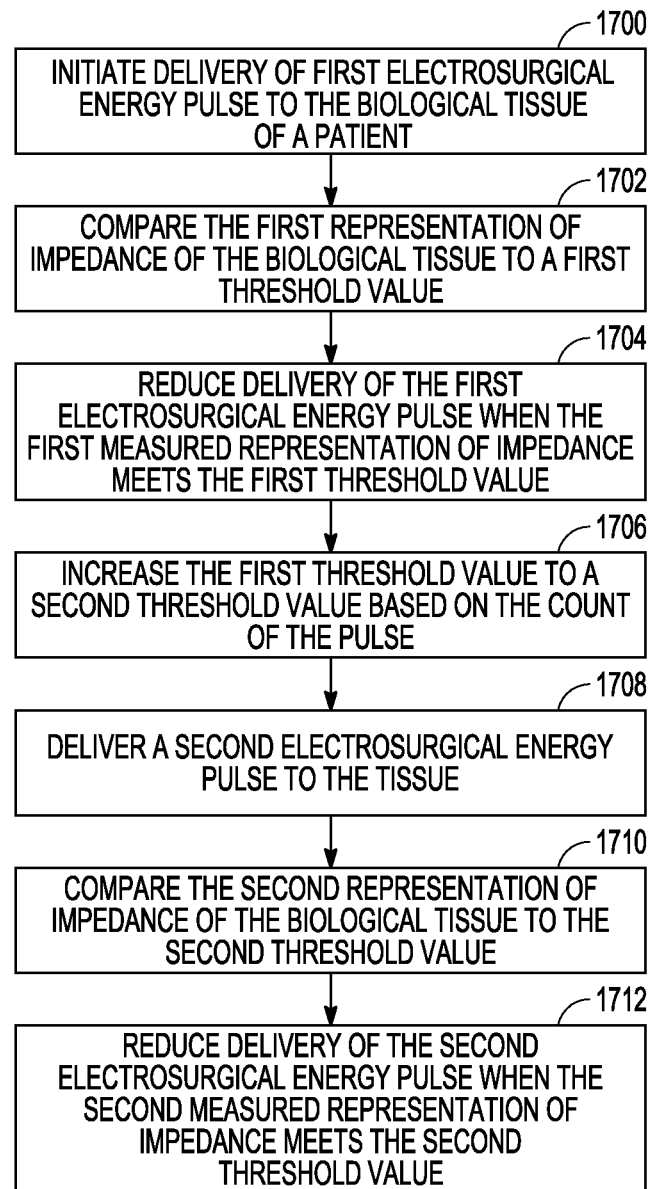
FIG. 21 is a flow diagram depicting another example of a thermal margin control technique that can be used in an electrosurgical system.

Staged Impedance Values to Control Thermal Margins in Systems with Slow CPUs (FIGS. 20 and 21)

There is often a desire to obtain high performance without increasing the processing burden on a system. Slower systems, which may be less expensive to purchase or maintain, can perform better if processing is kept low.

Typically, steam control and thermal margin control of devices used for vessel sealing can be achieved by monitoring one or more feedback systems. This can be a single true feedback element or multiple feedback elements that are interdependent, such as a calculation based on one or a number of events, or through a decision tree type structure.

An example of such a system can monitor a difference (or delta) between the lowest encountered calculated impedance and a rolling upper impedance. In other examples, a rate of impedance rise with respect to time, a change in phase angle, a change in current draw, and a change in voltage can be used as indicators of steam generation within tissues.

In monitoring a difference (or delta) between the lowest encountered calculated impedance and a rolling upper impedance, for example, newer, fast reaction hardware can use a specific boundary or decision point to determine whether an expected steam pocket has been created and, if so, whether the pocket is sized such that power should be reduced, momentarily stopped, or stopped completely. In older, slower reaction systems, the speed at which the steam pocket is created is the same, but the reaction time to reduce or stop the power is slower, which can result in "steam pocket overshoots" that can cause greater thermal margin.

By way of example, if an impedance threshold is set at 55 ohms, the older, slower-to-react system can overshoot the 55-ohm threshold and stop at 70 ohms. In contrast, newer electrosurgical systems can include faster analog-to-digital converters, processors, and other hardware that can allow sampling at millions of samples per second. In such systems, if an impedance threshold is set at 55 ohms, the newer system can stop at about the desired 55 ohms.

The present inventors have recognized the need to improve the thermal margin control in legacy electrosurgical systems. Through extensive observation of tissue effects, the present inventors have recognized that overshoot typically occurs through the early pulse phases of an electrosurgical waveform and that the rate of steam generation reduces throughout the waveform as the tissue becomes desiccated through the expulsion of fluid. Therefore, to solve the problem of overshoot and improve the thermal margin control, the present inventors have recognized the desirability of incorporating an intelligence within the output. In particular, the present inventors have recognized that the electrosurgical system can count the pulses of the electrosurgical signal and can assign different values of the trigger or threshold, e.g., an impedance value or impedance delta, based on the pulse number. In this manner, the threshold value of one or more of the initial electrosurgical energy pulses can be lowered, which can allow for overshoot and thus reduce the thermal margin of legacy electrosurgical systems.

FIG. 2, described above, depicts an example of a surgical system that can be used to implement various aspects of the thermal margin control techniques of this disclosure. As shown in FIG. 1, the surgical system of FIG. 1 can include an electrosurgical device such as the forceps 14. The forceps 14 can include two jaws, e.g., the first jaw member 36 and the second jaw member 38. In some examples, one of the two jaws can be moveable and the other jaw can be stationary. In other examples, both jaws can be moveable.

It should be noted that the thermal margin control techniques of this disclosure are not limited to electrosurgical devices that include jaws. Rather, the thermal margin control techniques can be implemented using devices such as spatulas and snares.

The electrosurgical device, e.g., the forceps 14, can include two or more electrodes sized, shaped, and/or otherwise configured to deliver the electrotherapeutic signal to the biological tissue, e.g., the tissue 16 of FIG. 1. In some examples, the electrodes can be integral with the jaws, e.g., the first jaw member 36 and the second jaw member 38, as in FIG. 1. In other examples, the electrodes can be coupled to the jaws.

An output circuit, such as including the power source 44 of FIG. 2, can be configured to generate and deliver electrosurgical energy to an output terminal, e.g., the instrument interface 42 of FIG. 2, for delivery to a patient. The output terminal can be configured to couple to an electrosurgical device, such as the forceps 14 of FIG. 1, and deliver electrosurgical energy, e.g., high frequency, such as RF energy, to biological tissue via electrotherapeutic signals. A control circuit of the surgical system, e.g., the control circuit 48 of the surgical system of FIG. 1, can be coupled to the output circuit and the control circuit can be configured to perform various aspects of the thermal margin control techniques.

FIG. 20 is a flow diagram depicting an example of a thermal margin control technique that can be used in an electrosurgical system. At block 1600, a user, such as a surgeon or clinician, can initiate delivery of electrosurgical energy to the biological tissue of a patient, such as tissue positioned between two jaws of the electrosurgical device. At block 1602, a control circuit, e.g., the control circuit 48 of the system 10 of FIG. 2, can count the number of the delivered electrosurgical pulse.

At block 1604, the control circuit can compare a parameter to a threshold value. In some examples, the parameter can be an impedance of the biological tissue, a change in impedance (or delta) of the biological tissue, a rate of change of the impedance of the biological tissue, a change in a current of the delivered electrosurgical energy pulse, a change in an output voltage of the delivered electrosurgical energy pulse, or a change in a phase angle, e.g., the phase angle between the voltage difference delivered across and electrical current conducted by the biological tissue. In some examples, a measurement circuit, e.g., the measurement circuit 46 of FIG. 2, to measure the parameter or measure electrical characteristics that can be used by the control unit, e.g., the processor 54 of FIG. 2, to calculate the parameter. In some examples, the control circuit can reduce the delivery of the plurality of electrosurgical energy pulses when a measured representation of impedance meets or exceeds an endpoint value, e.g., an endpoint value of about 100-600 ohms.

At block 1606, the control circuit can adjust the threshold value based on the count of the electrosurgical energy pulse. That is, the threshold value can be changed from one pulse to another pulse. For example, for a second pulse, the control circuit can adjust the impedance delta to 45 ohms, e.g., up from 40 ohms. In this manner, the control circuit can set a threshold value or boundary based on the count of the pulse. Tailoring the threshold value of one or more of the initial electrosurgical pulses based on the count of the pulse can help account for any overshoot caused by the delay in older, slower-to-react electrosurgical generator systems.

By way of a non-limiting example, it can be desirable to deliver an energy pulse that creates a change in impedance (or an impedance delta) of about 55 ohms in biological tissue. When a user initiates delivery of a first pulse of electrosurgical energy, the control circuit, e.g., the control circuit 48 of FIG. 2, can reset a counter, e.g., within the processor 54 of FIG. 2, and set a threshold value of a parameter, e.g., a change in impedance, to a first value. For example, the control circuit can retrieve data representing the threshold value for a first pulse from a memory device, e.g., the memory 56 of FIG. 2, and set the threshold value of an impedance delta for a first pulse to the retrieved data, e.g., representing 40 ohms.

The system can deliver the first pulse of energy and the control circuit can compare a measured parameter, e.g., the impedance delta, to the threshold value of 40 ohms. Once the measured parameter reaches 40 ohms, the control circuit can stop delivery of the first pulse. Because of the delay in older, slower-to-react electrosurgical generator systems, the system can overshoot the 40-ohm threshold and can actually stop once the impedance delta reaches about 55 ohms. The lowered threshold value for the first pulse can allow for the rapid rise of the first pulse, with overshoot, providing an actual impedance of 55 ohms due to slow reaction of the system. As mentioned above, in some examples, an impedance delta 55 ohms can be desirable.

Next, in preparation for delivering a second pulse, the control circuit can adjust the threshold value based on the count of the electrosurgical pulse. Here, the count is two and the control circuit can retrieve data representing the threshold value for a second pulse from the memory device and set the threshold value of the impedance delta for a second pulse to the retrieved data, e.g., representing 45 ohms.

The system can deliver the second pulse of energy and the control circuit can compare the measured parameter to the adjusted threshold value of 45 ohms. Once the measured parameter reaches 45 ohms, the control circuit can stop delivery of the second pulse. Because of the delay, the system can overshoot the 45-ohm threshold and can actually stop once the impedance delta reaches about 55 ohms. The adjusted threshold value for the second pulse can allow for the slightly slower ramp rate of the second pulse, providing an actual impedance of 55 ohms due to slow reaction of the system.

Next, in preparation for delivering a third pulse, the control circuit can adjust the threshold value based on the count of the electrosurgical pulse. Here, the count is three and the control circuit can retrieve data (or use previously retrieved data) representing the threshold value for a third pulse from the memory device and set the threshold value of the impedance delta for a third pulse to the retrieved data, e.g., representing 55 ohms.

The system can deliver the third pulse of energy and the control circuit can compare the measured parameter to the adjusted threshold value of 55 ohms. Once the measured parameter reaches 55 ohms, the control circuit can stop delivery of the third pulse. With the third pulse, the ramp rate can be slow enough that the system can react in time and stop once the impedance delta reaches 55 ohms.

In this manner, the threshold value of one or more of the initial electrosurgical energy pulses can be artificially lowered in that the desired threshold of 55 ohms, for example, remains the same despite the adjustments of 40 ohms, 45 ohms, etc. This artificial lowering of the threshold can allow for overshoot and thus reduce the thermal margin of legacy electrosurgical systems. Threshold values for additional pulses, such as the fourth, fifth, and higher pulses, may not need to be adjusted. For example, the fourth, fifth, and higher pulses can be set at 55 ohms, for example. In other examples, the third, fourth, fifth, and higher pulses can be adjusted.

In addition to the stratified pulse capability described above, the control circuit can use predictors to determine or select a set of pulse ratios to use. For example, a ratio can be between each of the adjusted threshold values to the desired threshold value. By way of non-limiting examples for purposes of illustration only, if the desired threshold is 55 ohms and the first, second, and third pulse thresholds are 40, 45, 50, respectively, the ratios can be 40/55, 45/50, and 50/55.

The predictors can identify the likelihood of impedance rise and allow for that in the calculation of the adjusted threshold values. For example, a tissue with a high initial impedance that drops to a low impedance in the first pulse can indicate a rapid rise and therefore a percentage reduction in the impedance delta being searched for. This can be because tissue with a higher initial impedance that drops suddenly can be indicative of tissue with a lot of fluid and therefore rapid steam rise. However, a tissue for which the impedance delta starts low and goes lower can have a different ratio selector or set of threshold values.

Various parameters that can be used as predictors can include an impedance of the biological tissue, a change in impedance (or delta) of the biological tissue, a rate of change of the impedance of the biological tissue, a change in a current of the delivered electrosurgical energy pulse, a change in an output voltage of the delivered electrosurgical energy pulse, or a change in a phase angle, e.g., the phase angle between the voltage difference delivered across and electrical current conducted by the biological tissue.

In some examples, the control circuit, e.g., the control circuit 48 of FIG. 2, can compare a first measured parameter to a second measured parameter and adjust the threshold value based on a difference between the first measured parameter and the second measured parameter. For example, a measurement circuit, e.g., the measurement circuit 46 of FIG. 2, can measure a first impedance delta, e.g., before a first pulse is delivered, and a second impedance delta, e.g., after the first pulse is delivered. Based on the difference between the first and second impedance deltas, the control circuit can select a particular set of adjusted impedance.

As a non-limiting example, the control circuit can have initially selected a first set of adjusted impedance delta threshold values for the first, second, and third pulses, such as 40 ohms, 45 ohms, and 55 ohms, respectively. However, based on the difference between the first and second impedance deltas, the control circuit can select a second set of adjusted impedance delta threshold values for the first, second, and third pulses, such as 45 ohms, 50 ohms, and 55 ohms, respectively.

In some examples, the control circuit can adjust the threshold value based on the first measured parameter being greater than the second measured parameter. In other examples, the control circuit can adjust the threshold value based on the first measured parameter less than the second measured parameter. In some examples, the control circuit can adjust the threshold value based on the rate of change between the first measured parameter and a second measured parameter.

Other factors can also be used to predict the correct ratios to use. For example, the rate of decrease with respect to time of the initial impedance can be used to indicate the rate of rise and therefore the correct threshold value or trigger. In addition, the initial impedance or even the prior tissue activation can be used to as predictors. Prior issue activation can be the last time that the surgeon, for example, grasped tissue and pushed the activation button.

FIG. 21 is a flow diagram depicting another example of a thermal margin control technique that can be used in an electrosurgical system. A control circuit, e.g., the control circuit 48 of the system 10 of FIG. 2, can count the number of the delivered electrosurgical pulse. In some examples, the control circuit can retrieve data representing the first (and more) threshold values from a memory device, such as the memory 56 of FIG. 2. At block 1700, a user, such as a surgeon or clinician, can initiate delivery of a first electrosurgical energy pulse to the biological tissue of a patient, such as tissue positioned between two jaws of the electrosurgical device.

At block 1702, the control circuit can compare a first measured representation of impedance, e.g., an impedance delta, of the biological tissue to a first threshold value, e.g., 40 ohms. In some examples, the measured representation of impedance can be an impedance of the biological tissue, a change in impedance (or delta) of the biological tissue, a rate of change of the impedance of the biological tissue, or a change in a current of the delivered electrosurgical energy pulse. In some examples, a measurement circuit, e.g., the measurement circuit 46 of FIG. 2, to measure the representation of impedance or measure electrical characteristics that can be used by the control unit, e.g., the processor 54 of FIG. 2, to calculate the representation of impedance. In some examples, the control circuit can reduce the delivery of the plurality of electrosurgical energy pulses when a measured representation of impedance meets or exceeds an endpoint value, e.g., an endpoint value of about 250-350 ohms.

At block 1704, the control circuit can reduce or terminate delivery of the first electrosurgical energy pulse when the first measured representation of impedance meets or exceeds the first threshold value. For example, the control circuit can reduce or terminate delivery of the first pulse when the measured impedance delta meets or exceeds the 40-ohm threshold value associated with the first pulse.

At block 1706, the control circuit can increase the first threshold value to a second threshold value based on the count of the pulse. For example, based on the count being two, the control circuit can increase a 40-ohm impedance delta threshold value associated with the first pulse to a 45-ohm threshold impedance delta value associated with the second pulse.

At block 1708, the control circuit can control the electrosurgical generator, e.g., electrosurgical generator 12 of FIG. 2, to deliver a second electrosurgical energy pulse to the tissue. At block 1710, the control circuit can compare a second measured representation of impedance, e.g., an impedance delta, of the biological tissue to the second threshold value, e.g., 45 ohms. At block 1712, the control circuit can reduce or terminate delivery of the second electrosurgical energy pulse when the second measured representation of impedance meets or exceeds the second threshold value. For example, the control circuit can reduce or terminate delivery of the second pulse when the measured impedance delta meets or exceeds the adjusted 45-ohm threshold value of the second pulse.

In some examples, in preparation for delivering a third pulse, the control circuit can adjust the threshold value based on the count of the electrosurgical pulse. Here, the count is three and the control circuit can retrieve data (or use previously retrieved data) representing the threshold value for a third pulse from the memory device and set the threshold value of the impedance delta for a third pulse to the retrieved data, e.g., representing 55 ohms.

As described above with respect to FIG. 20, predictors can be used to determine or select a set of pulse ratios to use. For example, the control circuit, e.g., the control circuit 48 of FIG. 2, can compare a first measured parameter to a second measured parameter and adjust the threshold value based on a difference between the first measured parameter and the second measured parameter. For example, a measurement circuit, e.g., the measurement circuit 46 of FIG. 2, can measure a first impedance delta, e.g., before a first pulse is delivered, and a second impedance delta, e.g., after the first pulse is delivered. Based on the difference between the first and second impedance deltas, the control circuit can select a particular set of adjusted impedance.

By using the thermal margin control techniques described above, e.g., with respect to FIGS. 20 and 21, the threshold value of one or more of the initial electrosurgical energy pulses can be artificially lowered. This artificial lowering of the threshold can allow for overshoot and thus reduce the thermal margin of legacy electrosurgical systems.

Although described separately, the two-boundary threshold techniques, open circuit check techniques, power correction techniques, reduced thermal margin techniques for combination ultrasonic energy and electrosurgical energy systems, and thermal margin control techniques described above can be implemented individually or in combinations of two or more of the techniques described in this disclosure, as desired.

For example, a system that implements the two-boundary threshold techniques can also implement one or more of the power correction techniques, reduced thermal margin techniques for combination ultrasonic energy and electrosurgical energy systems, and thermal margin control techniques described above. By way of a non-limiting example, for purposes of illustration only, a system that implements the two-boundary threshold techniques can also implement the thermal margin control techniques that can artificially lower threshold values.

In another non-limiting example, for purposes of illustration only, a combination ultrasonic energy and electrosurgical energy systems that implements reduced thermal margin techniques by reducing a level of or terminating the delivery of energy based on a characteristic of a measured representation of impedance of the biological tissue can also implement power correction techniques that can apply a power correction to the power control of the electrosurgical generator based on whether a measured impedance is within a range of impedances, e.g., 0-20 ohms.

Consumed Energy Monitoring and Open Circuit Evaluation (FIGS. 22A-22D)

To assist with determining whether to continue with additional tissue drying phases, the present inventor has recognized that at the end of a drying phase, the amount of energy (and/or charge) delivered to the tissue during the just completed drying phase (or just completed interrogation phase and drying phase) can be evaluated, as described in detail below. If the amount of energy (and/or charge) applied is below the energy (and/or charge) threshold value and has created a sufficient impedance delta value, then the tissue is sufficiently dry, and the process can continue to the next stage. However, if the amount of energy (and/or charge) applied is above the energy (and/or charge) threshold value and has created a sufficient impedance delta value, then the tissue is too wet and needs another drying phase.

FIGS. 22A-22D depict a flow diagram of an example of an energy delivery technique that can use, among other things, an amount of energy delivered to a biological tissue in its decision-making process. Although the technique depicted in the flow diagram of FIGS. 22A-22D is described as power-controlled, in some examples, the technique can be voltage-controlled.

Three steps are depicted in the flow diagram of FIGS. 22A-22D and are described in detail below. The portion of the flow diagram labeled Step 1, which can be an interrogation phase or other low energy phase, can be a power-controlled step (or, in other examples, a voltage-controlled step) where an electrosurgical generator, such as the electrosurgical generator 12 of FIG. 2, can control delivery of a low power electrotherapeutic signal, such as 10 W, to the biological tissue. In some examples, Step 1 can considered to be a steam-dissipation phase in which steam in the tissue generated during Step 2 is allowed to dissipate in order to prevent thermal margins.

In some examples, Step 1 can be set to run for a specific duration, such as 250 ms, during which time the electrosurgical generator can control the power as closely as possible to ensure a consistent delivery level. During Step 1, a control circuit, such the control circuit 48 of FIG. 2, in combination with a measurement circuit, such as the measurement circuit 46 of FIG. 2, can track various parameters. For example, the control circuit and the measurement circuit can begin measuring and storing the maximum and minimum impedances associated with a particular delivered pulse (pulse RMax and pulse RMin)(also tracked in Step 2). In addition, during the application of power in Steps 1 and 2, the control circuit and the measurement circuit can store the values of the amount of energy (and/or charge) delivered to the tissue.

The amount of energy delivered to the tissue can be measured in joules and is the integration of the amount of power delivered in watts. The amount of charge delivered to the tissue can be measured in coulombs and is the integration of amount of current in amps. Although generally shown and described below with respect to an amount of energy delivered to the tissue, the techniques of FIGS. 22A-22D can additionally or alternatively use an amount of charge delivered to the tissue.

Figure 22A:
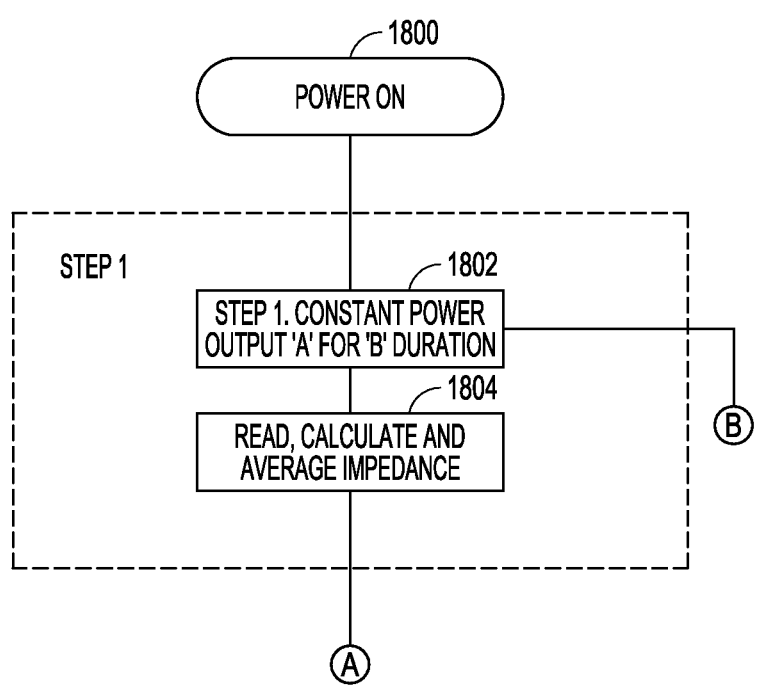
FIGS. 22A-22D depict a flow diagram of an example of an energy delivery technique that can use, among other things, an amount of energy delivered to a biological tissue in its decision-making process.

The method shown in FIG. 22A begins at block 1800 with the power of the electrosurgical generator, such as the electrosurgical generator 12 of FIG. 2, turned ON. At block 1802, the method enters Step 1 and the electrosurgical generator can deliver a constant power output "A" for a duration of time "B". At block 1804, the measurement circuit and the control circuit can read or calculate the impedance values of the tissue and then the control circuit can average those values. In some examples, the average impedance determined during Step 1 can have an effect on the ramp rate selected for applying energy in Step 2, the next power-control phase.

Figure 22B:
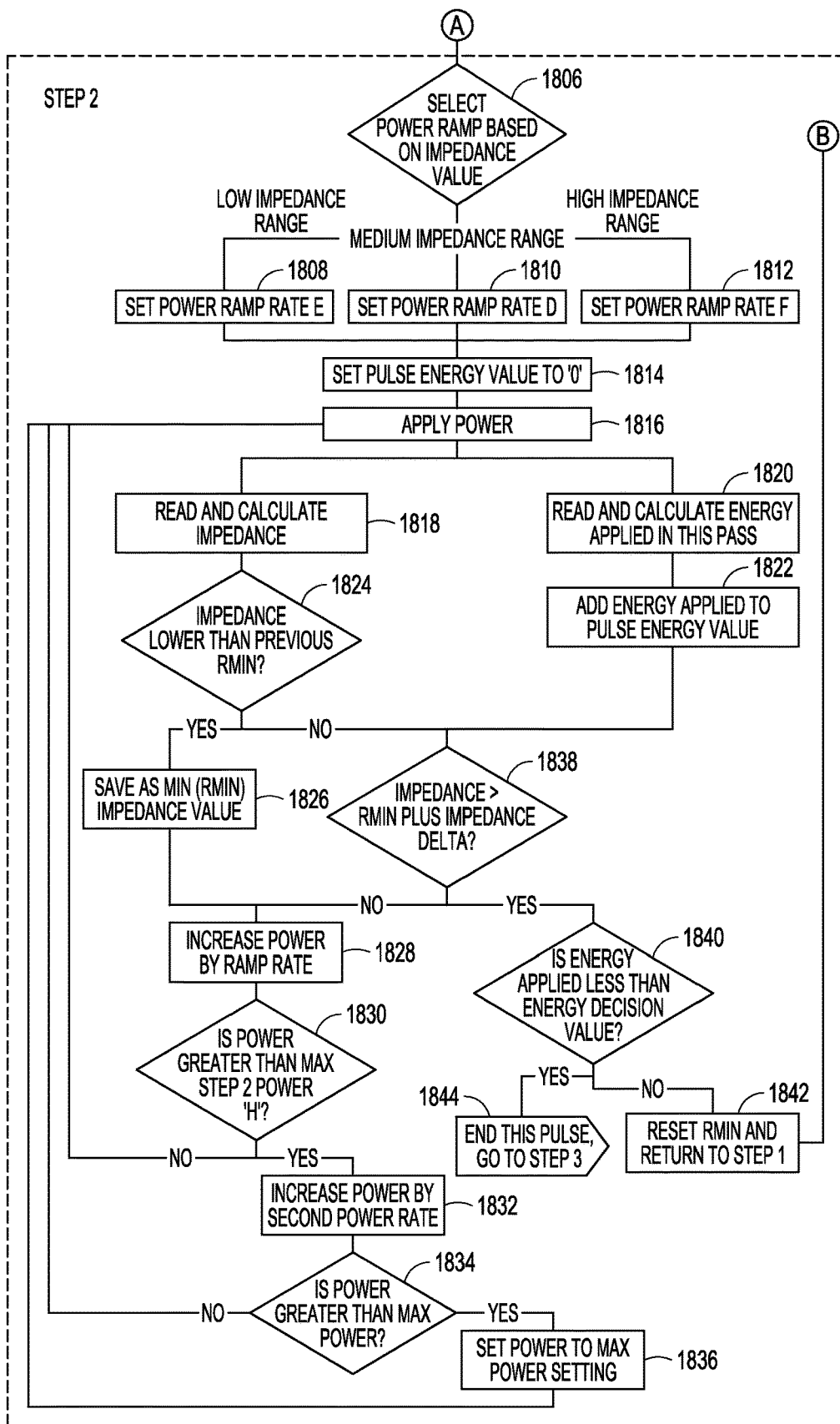

In FIG. 22B at block 1806, the method enters Step 2, which can be a drying phase. At block 1806, the control circuit can automatically select a power ramp rate based on the impedance value determined in Step 1. Different bands or ranges of impedance values can result in different output power ramp rates. For instance, for a lower impedance range, such as 1 ohm to 15 ohms, the control circuit can select a ramp rate "E" (block 1808)(such as 0.05 W/ms), while for a medium impedance range, such as 15 ohms to 75 ohms, the control circuit can select a ramp rate "D" (block 1810)(such as 0.035 W/ms), and for a high impedance range, such as 75 ohm to 400 ohms, the control circuit can select a power ramp rate "F" (block 1812)(such as 0.035 W/ms). In some examples, there can be only two ramp rates, such as a fast first ramp rate and a slower second ramp rate, such as shown in FIG. 4 in t1-t2 and t2-t3. At block 1814, after the power ramp rate has been selected, the control circuit can set the cumulative pulse energy (and/or charge) value to 0 and apply power to the tissue via an electrotherapeutic signal at block 1816.

Next, the method can perform activities in parallel, including the control circuit reading or calculating the impedance of the tissue at block 1818 and reading or calculating the energy (and/or charge) applied during this particular pass at block 1820. In some examples, rather than being run in parallel, the activities can be mixed in a single process.

At block 1820, the control circuit can read and calculate the energy (e.g., in joules) (and/or charge, e.g., in coulombs) applied during this pass to the biological tissue. Then, at block 1822, the control circuit can add the energy (and/or charge) applied during this pass to the pulse energy (and/or charge) value to generate a cumulative applied energy (and/or charge) value.

In the example shown in FIG. 22A and in parallel with the calculation of the energy applied, after calculating the impedance in block 1818, the control circuit 48 of FIG. 2 can determine at block 1824 whether the impedance is lower than a previous impedance Rmin. In some examples, in determining the minimum impedance Rmin, the control circuit can start with a default initial impedance, such as 1000 ohms. If the next measured or calculated impedance is 20 ohms, for examples, then 20 ohms is the new minimum impedance Rmin. Similarly, if a subsequent measured or calculated impedance is 15 ohms, then 15 ohms is the new minimum impedance Rmin. The minimum impedance Rmin can be from Step 1 or from a present impedance reading.

If the present impedance reading is lower than a previous impedance Rmin ("YES" branch of block 1824), then at block 1826 the control circuit can store the present impedance reading as the new minimum resistance value Rmin. Then, at block 1828, the control circuit can increase the power, such as along a specific power ramp rate trajectory (power increased against time).

At block 1830, the control circuit can determine whether the power is greater than a maximum power level for Step 2 (power "H"). If the power is not greater than the maximum power level ("NO" branch of block 1830), then the process returns to block 1816 and another pass is started. However, if the power is greater than the maximum power level ("YES" branch of block 1830), then the control circuit can adjust or change the power ramp rate to a second ramp rate at block 1832. In some examples, the second ramp rate is slower than the first ramp rate.

At block 1834, the control circuit can determine whether the applied power is greater than the maximum power level. If the power is not greater than the maximum power level ("NO" branch of block 1834), then the process returns to block 1816 and another pass is started. However, if the power is greater than the maximum power level ("YES" branch of block 1834), then the control circuit can change the power ramp rate to the maximum power level setting at block 1836 and then the process returns to block 1816 and another pass is started.

Referring back to decision block 1824, if the present impedance reading is not lower than a minimum impedance Rmin ("NO" branch of block 1824), then the control circuit can determine whether the present impedance reading is greater than the minimum impedance Rmin plus an impedance delta at block 1838. If the present impedance reading is not more than the minimum impedance Rmin plus the impedance delta ("NO" branch of block 1838), then the control circuit can move to block 1828 and the method can continue as described above.

In some examples and in contrast to determining whether the measured electrical current is less than the predetermined faction of the maximum electrical current at step 1824, the control circuit 48 can determine whether the measured electrical current is less than the predetermined fraction (or offset) of a current value measured at a predetermined time interval following the initiation of the pulse. For impedance monitoring systems, the control circuit 48 can determine whether the measured impedance is greater than the predetermined fraction (or offset) of a resistance value measured at a predetermined time interval following the initiation of the pulse.

However, if the present impedance reading is more than the minimum impedance Rmin plus the impedance delta ("YES" branch of block 1838), then the control circuit can move to decision block 1840. By way of a non-limiting example, the impedance delta can be 55 ohms, the present impedance reading can be 75 ohms, and the minimum impedance Rmin can be 15 ohms. In this non-limiting example, the present impedance reading, e.g., 75 ohms, is more than the minimum impedance Rmin, e.g., 15 ohms, plus the impedance delta, e.g., 55 ohms ("YES" branch of block 1838), then the control circuit can move to decision block 1840.

As described above, the control circuit determined whether there was a set difference between the present impedance reading and the minimum impedance Rmin. If the difference was greater than a set amount, e.g., 55 ohms, then the control circuit can now check how much energy was delivered during the previous Step 1 and the current Step 2 phase at this point in time. At block 1840, the control circuit can determine whether the amount of energy (or charge) applied is less than an energy threshold value (or charge threshold value), such as 20 Joules (or 2 Coulombs of charge). If the amount of energy applied is not less the energy threshold value ("NO" branch of block 1840), then the control circuit can reset the minimum impedance Rmin and return to Step 1 at block 1842. Eventually, the system will return to a second drying cycle in Step 2. In this manner, the control circuit can control the energy delivery of the therapeutic signal provided to the engaged biological tissue during a second drying phase if the amount of energy delivered exceeds the threshold energy value.

However, if the amount of energy applied (or charge applied) is less the energy threshold value (or charge threshold value) ("YES" branch of block 1840), then the control circuit can end the pulse and go to Step 3 as shown at block 1844. In this manner, the control circuit can control the energy delivery of the therapeutic signal provided to the engaged biological tissue during a finishing phase if the amount of energy delivered is less than the threshold energy value.

Figure 22C:
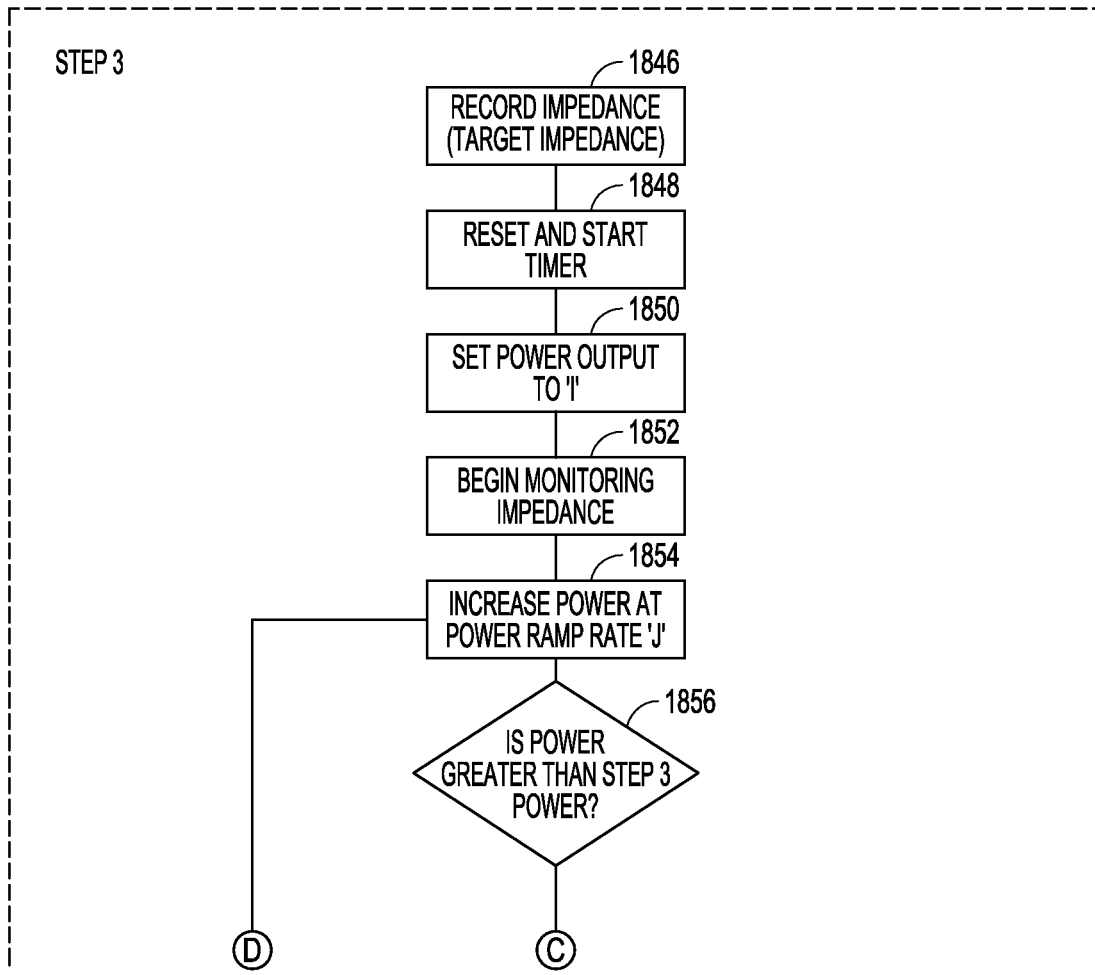
Figure 22D:
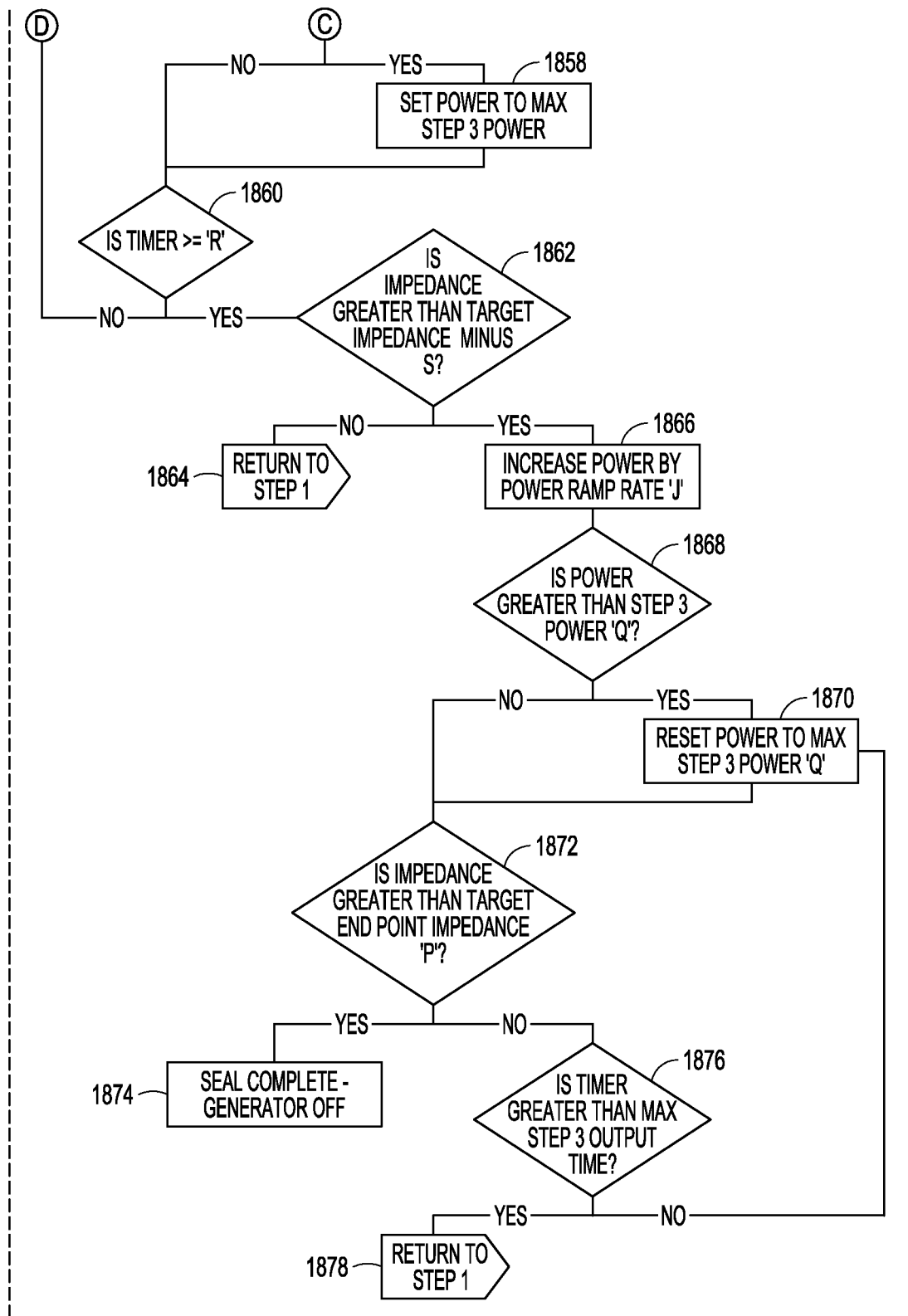

Step 3, which can be a finishing phase, begins at block 1846 in FIG. 22C. At block 1846, the control circuit can store or record the target final impedance. In some examples, the target final impedance can be a set final number. In some examples, the target final impedance can be a delta calculation from the lowest impedance value read or calculated in this step plus a predetermined percentage or delta value. For example, if the minimum impedance Rmin for this step is measured to be 20 ohms, then a predetermined delta of 280 ohms can be added to the final target impedance, to set the value of the target final impedance to be 300 ohms. In some examples, the target final impedance can be a delta calculation from an impedance measurement taken after a predetermined time interval following the initiation of the pulse plus a predetermined percentage or delta value.

In some examples, the target final impedance can be dependent on the number of pulses, such as drying pulses. For example, if the end point is dependent on the pulse number and if two pulses are delivered to the tissue, then the final impedance value might be 320 ohms. However, if five pulses are delivered to the tissue, then the final impedance might be 280 ohms. If the endpoint is not achieved within a predetermined amount of time, such as 2 seconds, then the method can return to Step 1 in an attempt to further drive fluid from the tissue and reach a satisfactory end point impedance.

At block 1848, the control circuit can reset and initiate a timer, such as in response to a delivery of electrosurgical energy to the biological tissue, such as positioned between two jaws of the electrosurgical device or in contact with one or more electrodes. If a predetermined impedance delta between the present impedance reading and the minimum impedance Rmin for this pulse is not met before a time interval is reached, then the output is returned to the first step, as this may indicate that the tissue still contains too much water.

At block 1850, the control circuit can set the power output to power level "I". In some examples, the control circuit can control delivery of the electrotherapeutic signal to the tissue using a constant power ramp rate. In some examples, the constant power ramp rate of Step 3 can be slower than the previous ramp rates, such as in Step 2. The control circuit can continue delivery using the constant power ramp rate until a final impedance value is reached, such as 320 ohms in a non-limiting example.

At block 1852, the control circuit can begin monitoring the impedance of the tissue. As described below, the control circuit can compare, e.g., intermittently, a representation of impedance of the biological tissue to a threshold value, such as at blocks 1862 and 1872, and continue the delivery of electrosurgical energy until the threshold value is met. At block 1854, the control circuit can increase the power to a constant power ramp rate "J". In some examples, before delivering the electrosurgical energy at the constant power ramp rate, the control circuit can deliver the electrosurgical energy at a constant power.

At block 1856, the control circuit can determine whether the power is greater than a maximum Step 3 power level. If the power is greater than the Step 3 maximum power level ("YES" branch of block 1856), then the control circuit can set the power to the Step 3 maximum power level at block 1858 in FIG. 22D. After either setting the power to the Step 3 maximum power level at block 1858 or if the power is not greater than the Step 3 maximum power level ("NO" branch of block 1856), then the control circuit can compare the timer value to the time interval "R" at decision block 1860.

If the timer value is not greater than or equal to the time interval "R" ("NO" branch of block 1860), then the method can return to block 1854 and the control circuit can increase the power. However, if the timer value is greater than or equal to the time interval "R" ("YES" branch of block 1860), then the control circuit can determine if the impedance is greater than the minimum value within this pulse plus a predetermined delta impedance at block 1862, where the predetermined delta impedance is the difference between the measured impedance and the lowest value of the impedance measured in the pulse.

If the control circuit determines that the impedance is not greater than the target impedance minus a predetermined delta impedance ("NO" branch of block 1862), then the method can return to Step 1 as shown at block 1864. In this manner, the control circuit can reduce or terminate the energy delivery during the therapeutic phase in response to the measured, e.g., intermittently, impedance changing by a predetermined delta impedance value.

However, if the control circuit determines that the impedance is greater than the target impedance minus a predetermined delta impedance ("YES" branch of block 1862), then the method can move to block 1866 and increase the power to power ramp rate "J".

At decision block 1868, the control circuit can determine whether the current power is greater than the maximum Step 3 power level. If the current power is greater than the maximum Step 3 power level ("YES" branch of block 1868), then the control circuit can reset the power to the maximum step 3 power level "Q" at block 1870.

After either setting the power to the Step 3 maximum power level at block 1870 or if the power is not greater than the Step 3 maximum power level ("NO" branch of block 1868), then the control circuit can determine whether the impedance is greater than the target final impedance "P" at block 1872. If the control circuit determines that the impedance is greater than the target final impedance ("YES" branch of block 1872), then the seal is complete, and the control circuit can turn the electrosurgical generator OFF at block 1874. However, if the control circuit determines that the impedance is not greater than the target final impedance ("NO" branch of block 1872), then the control circuit can determine whether the timer is greater than the maximum Step 3 output timer at block 1876.

If the timer is greater than the maximum Step 3 output timer ("YES" branch of block 1876), then the method can return to Step 1 as shown at block 1878. For example, if the timer times out, this can be an indication that the tissue was not sufficiently desiccated during the previous steps. However, if the timer is not greater than the maximum Step 3 output timer ("NO" branch of block 1876), then the method can return to block 1866 to increase the power ramp rate.

In some examples, the timer at block 1860 can be used to detect a potential open circuit condition. For example, if the jaws of an electrosurgical device, such as the forceps 14 of FIG. 1, were opened during the sealing procedure, the electrosurgical generator could mistakenly determine that the accompanying rise in impedance was the result of the tissue drying.

Non-limiting values for the parameters A-S in FIGS. 22A-22 are shown below in Table 1:

TABLE 1

| | |
|---|---|
| A | 10 W |
| B | 250 ms |
| D | 0.035 W/ms |
| E | 0.05 W/ms |
| F | 0.035 W/ms |
| H | 60 W |
| I | 15 W |
| J | 0.035 W/ms |
| P | 320 ohms |
| Q | 100 W |
| R | 100 ms |
| S | 20 ohms |

In accordance with this disclosure, during Step 3, the timer at block 1860 can be started. Upon reaching the target final impedance (or threshold value), the control circuit can record an elapsed time. If the target final impedance (or threshold value) is reached in a very short period of time, such as before the threshold time limit, then the control circuit can determine that an open circuit has occurred rather than a completed seal and declare an error state. In other words, the control circuit can declare an error state if the elapsed time is less than a time limit. The time limit may be 50 ms, 100 ms, or another time period.

For example, the control circuit can determine a difference between the minimum measured impedances Rmin and the current or maximum measured impedance and compare the determined difference to a predetermined delta impedance value. In some examples, the control circuit can increase a power ramp rate of the electrosurgical energy in response to the comparison. The control circuit can continue to increase the power ramp rate, such as at block 1854, until either the determined difference meets or exceeds the predetermined delta impedance value, such as at block 1862, or a power limit is reached, such as at block 1858.

However, in some examples, if the determined difference is equal to or greater than the predetermined delta impedance value and the timer is greater than the threshold time limit, the control circuit can declare an error state and generate an error signal. In some examples, the open circuit error signal can cause the control circuit to communicate an error message to the user, such as using the user interface 50 of FIG. 2, and to quickly terminate power to the electrosurgical device.

In some examples, the control circuit does not terminate power on a time mark. Instead, the power can continue until the final impedance is reached. At this point, the control circuit can evaluate the time interval to see if mitigating actions are needed. For example, a time interval or threshold set too long can produce false negatives, e.g., a good seal is formed, but the system has determined that an open circuit is present), especially on thin tissue that seals quickly. A time interval or threshold set too short can produce false positives, e.g., a good seal is not formed, but the system does not detect an error), which can occur when the user slowly opens the jaws, for example.

Dwell Time Between Pulses

It can be desirable to deliver electrotherapeutic signals using pulsed waveforms. Through the pulsing of an electrosurgical signal, the tissue between the device jaws can be heated. Without pulsing, the tissue can heat and as it passes through different temperature ranges, typically increasing as more and more energy is applied, the fluid within the tissue can reach a boiling point. The boiling point can be dependent on the composition of the fluid that is being boiled and also on the pressure at which the jaws are clamping the tissue (changing the pressure alters the boiling point). This results in steam generation.

The steam created can increase the tissue impedance and, as a result, less heating current flows through the tissue and more voltage is driven into the tissue. The steam grows into steam pockets and, because the steam changes phase as it evaporates, the volume of the pocket is now much greater. This new greater volume further increases the impedance and, as such, more voltage is required to achieve the same power input. In the meantime, the steam is now transitioning from its previous location between the jaws and extending into the surrounding tissues.

The higher voltages required to power through these steam pockets results in increased adherence of the tissues to the energy application surface, such as the jaws, while the steam being exuded into the surrounding tissues away from the application site is a negative called thermal margin. The thermal margin can damage structure that were not intended for tissue modification and can ultimately result in post-operative tissue necrosis and perforation of vital organs or organ structures. To overcome the propagation of steam pockets into surrounding tissues and higher required driving voltages, one control method currently utilized is pulsing.

Pulsing is where there is a pause in the application of energy delivered to the tissue of such a level that can modify the tissue. In some examples, the energy delivery is stopped for a period of time. In other examples, the energy level can be reduced to a level where the energy does not have a significant tissue effect. It can be desirable to apply at least some energy to the tissue rather than stop delivery completely to allow continuous feedback or almost instantaneous feedback of the tissue state to the control circuit.

In some approaches, a fixed period of 250 ms can be used as a pause period or "dwell time" which can ensure the tissue steam pockets have significantly condensed before energy is reapplied. A dwell time is a time interval following a first pulse and preceding a second pulse. If dwell times less than 250 ms are used, the steam pockets may not be sufficiently depleted, and the subsequent application of energy can rapidly reinstate the steam pockets.

Although typically true for the first pulse with shorter than a 250 ms pause, it is less clear for the subsequent pulses. For a second pulse, a dwell time such as 200 ms can be appropriate, depending on what volume of tissue and its related water content exists between the jaws. Subsequent pulses may need even less time (for example, a fifth pulse may need 50 ms or less) to allow the re-condensing of the now much reduced fluid content between the device jaws.

During these "dwell times", the fluid can migrate back into the target issue. During a dwell time, the generator can provide a low power signal to the tissue, which is low enough to not trigger a tissue effect. Small decreases in tissue thickness are typically noted as the outcome of vessel sealing and the extruded tissue contains fluid. Fluid can also be driven out by the steam having high pressure and pushing more mobile elements out of the area between the device application plates, such as extracellular fluid.

Unfortunately, not all tissues have the same fluid levels or tissue fluid mobility, and not even the same amount of tissue thickness or width is grasped between the device jaws for each seal. As such, a fixed standard reduction in a pause period between pulses may not provide an effective or accurate pause time controller.

In addition, there can be a product pressure to shorten the total activation as much as possible. The conservative choice of estimating a long dwell time and applying it even for dwell periods that do not require such a long time can extend total activation unnecessarily. The unnecessary extension of the total activation can lengthen surgery times and can increase user fatigue, among other things.

To overcome the problems mentioned above, the present inventors have recognized that the control circuit can utilize characteristics known about the tissue between the jaws to accurately predict the most appropriate reduced pause period. For example, the control circuit can query a stored data set, such as a look up table, and using one or more known characteristics about the tissue can determine a reduced pause period or "dwell time". The reduced dwell time can reduce the total activation time of the seal cycle, without impacting low thermal margins and while still providing high confidence in a reliable seal.

In some examples, a control circuit, such as the control circuit 48 of FIG. 2, can deliver first and second electrosurgical energy pulses to biological tissue in electrical communication with, such as physically engaged to, positioned between, or otherwise coupled to, two electrodes of the surgical device, where the first and second electrosurgical energy pulses are separated from one another by a corresponding dwell time. The control circuit can then determine the dwell time corresponding to at least one of the electrosurgical energy pulses following the first electrosurgical energy pulse.

In some examples, a control circuit, such as the control circuit 48 of FIG. 2, can determine and use the amount of energy applied to the tissue to determine an optimized dwell time. The amount of fluid between the device jaws requires a particular amount of energy in order to boil at a known energy application rate. The control circuit can estimate how much fluid is present by determining how much energy was delivered to the jaws to create a thermodynamic change to the tissue. The control circuit can query the stored data set using the determined amount of energy delivered to identify an appropriate corresponding dwell time. For large steam generation pulse cycles created using large amounts of energy, the control circuit can provide a longer dwell time to condense, and for smaller steam generation pulse cycles created using smaller amounts of energy, the control circuit can provide a shorter dwell time to condense.

In other examples, rather than use a stored data set, such as a look up table, the control circuit can determine a dwell time as a ratio of the determined energy applied to the jaws. In other examples, the control circuit can determine a dwell time as a factor of the determined energy applied to the jaws. As a non-limiting example, if the energy applied to the jaw was 20 joules, then the wait time can be 200 ms (X*10 ms). So, 30 joules can correspond to 300 ms. The equation X*10 is an example and not intended to be limiting. It can also be part of a logarithmic scale or other math-based ratio term.

In addition, the period of time it takes to boil tissue between the jaws (at a set or known variable power) is another way of determining a dwell time long enough to ensure that sufficient condensation mechanisms have occurred before applying the next tissue modifying level of energy to the tissue. In some examples, the control circuit can attempt to cut the power off short of boiling or with a little boiling as possible. The control circuit can determine that a longer dwell time is needed if it takes a longer period of time to boil tissue as more energy would have been delivered to the tissue. For example, the control circuit can initiate a timer upon delivering a pulse, determine whether the tissue has boiled or is close to boiling and if so, stop the timer, compare the timer to one or more values associated with corresponding dwell times, and determine or select a dwell time based on the comparison. As the timer value increases, the dwell times can be increased. As non-limiting examples for purposes of illustration only, a 250 ms dwell can be used if it takes 30 joules to boil or almost boil the tissue, and a 150 ms dwell can be used if it takes 18 joules to boil or almost boil the tissue. These values can may depend upon the surface area of the jaws of the device being used, or other factors.

Although the energy applied to the tissue can be a strong indicator of the amount of steam being created, the impedance of the tissue can also impact the accuracy of the setting. For example, if the tissue has a higher electrical impedance (such as fat), it can take more voltage and less current to boil the tissue, whereas if the tissue is very conductive, the current does the work and creates large steam pockets with the same amount of energy. Therefore, it can be desirable for a system that uses energy application to determine a dwell time to also determine and use the tissue impedance that the energy used to create the boiling effect.

The control circuit can use other electrical characteristics to determine a dwell time, including one or more of the following: current, reactance, inductance, impedance, resistance, power, phase angle, and energy to check or improve a signal.

Steam is the result of the delivered current, which excites the molecules within the tissue and causes heating. When more current is required to heat the tissue, it suggests that more fluid is residing within the tissue, understanding that the tissue structure itself is much higher resistivity than the fluid content. Therefore, depending on the function of the electrotherapeutic signal, e.g., how the signal applies energy, it can be desirable for the control circuit to determine a peak current applied in the previous pulse, or the current delivered as a function of time, or the total amount of current delivered in that previous pulse. The control circuit use the determined current and query a stored data set, such as a look up table, and determine or select a dwell time based on the comparison.

For example, the control circuit, such as the control circuit 48 of FIG. 2, can control and apply power to the tissue with current and voltage being allowed to float depending on the tissue impedance (this is a simplified explanation for general understanding). The control circuit can determine the total amount of current applied in the previous pulse, such as by integrating the amount of current delivered, which can assist in understanding how much steam could have been created during an energy application. Current (I) is equal to the rate of change of the electric charge (Q) with respect to time (I=dQ/dt). Therefore, the integral of the current I over a period of time is equal to the total amount of electric charge (Q) during that period of time.

Instead of using the total amount of energy delivered to the tissue, the present inventors have determined that the total amount of charge delivered can be used to determine a dwell time. In some examples, the control circuit can determine the dwell time as a ratio of the total amount of charge or as a factor of the total amount of charge. In other examples, the control circuit can use the total amount of charge to determine the dwell time using a stored data set, such as a look up table, or by using some other mathematically derived calculation to provide an appropriate dwell time that does not need to be the same for all energy pulses.

The dwell time can be further refined by including other factors, as described above, or exclusions. An example of such an exclusion can be if the current was delivered over a period of time greater than 300 ms, then the control circuit can reduce the dwell time because the amount of tissue within the jaw may be having a significant impact. As such, the control circuit can initiate a timer, compare the timer to a threshold value, such as 300 ms, and determine a dwell time based on the comparison. Alternatively, one or more feedback signals can be used, such as phase angle, to predict the composition of the tissue between the energy conduction elements. The control circuit can then factor in these feedback signals as indicators to determine an appropriate dwell time.

Incremental Adjustment of Control Parameter as a Function of a Monitored Variable An initial transition of the collagen occurs at about 58 (±10) degrees Celsius (C.), where conformal changes occur to the collagen fibrils. The main transition can occur at about 65 (±10) C, which corresponds to the process of gelatinization of collagen in a hydrated environment and is caused by the breaking of internal cross-links. Other important and notable temperatures bound tissue modification. At a general tissue temperature of between about 90-100 degrees C., additional phase changes start to occur inside the tissue, the most notable being the water converting to steam. This change is not desirable as the steam is resistive and although it drives energy robbing fluid out of the tissue, it also can damage surrounding tissues via its migration into adjacent structures. This is not desirable as this damage can be uncontrolled and can affect tissue outside of the jaw footprint.

From a clinical standpoint, this means that a surgeon should be mindful of any potential "thermal spread" when using a device and activating it close to a sensitive adjacent structure. This is not desirable and can lead to accidental tissue damage such as perforation and necrosis. Both of which may be instant or worse still, occur many days after the application of energy.

Steam containing tissue is also more electrically resistant than the same tissue with the water in a liquid state. This means that more of the energy that drives the tissue state change converts from current to voltage. Because the current typically does the work of heating via molecular excitation, it can be advantageous to limit the time in the steam phase for good vessel sealing.

The present inventors have recognized the need for improved techniques of power control (or voltage control) that attempts to maintain the power output for longer in the advantageous state of collagen transition, before control is lost and bubble field generation occurs. Using various techniques described in detail below, an electrosurgical generator, such as the electrosurgical generator 12 of FIG. 2, can control an energy delivery of the therapeutic signal provided to biological tissue during a portion of a therapeutic phase according to an incremental change in energy delivery as a function of a change in a measured electrical parameter of the biological tissue.

Applying energy to tissue can generate steam. As the amount of steam increases, the impedance increases. An increase in impedance can be an indication of steam generation. As the impedance increases, the current decreases and the voltage increases for the same amount of power being delivered (P=V*I). If, after the control circuit determines that steam is being generated, the control circuit continues to apply the same amount of power, the steam generation can undesirably increase and can adversely affect adjacent tissue. However, by using various techniques of this disclosure, the control circuit can monitor a change in an electrical parameter, such a current or impedance, and reduce the power, for example, to keep the tissue in a state in which steam is just beginning to be generated, but not generated in large amounts, which can be desirable for affecting the collagen without undesirably creating thermal margin.

A control circuit and a measurement circuit, such as the control circuit 48 and the measurement circuit 46 of FIG. 2, can monitor the current output of the generator and increases or decreases in the current can be translated into corresponding increases or decreases in the output power. In some examples, the correlation between an increase in current or a decrease in current and the subsequent control of increasing the power or decreasing the power can be directly proportional.

In some examples, the control circuit can scale the power application so as to provide different powers depending on the change in the measured electrical parameter, such as current or impedance. The scaling can be a function of the change in the measured electrical parameter of the biological tissue. In some examples, the function can define a curve. In other examples, the function can be a linear equation, such as a linear translation of the change in the value of the measured electrical parameter, such a current or impedance, to the change in power or voltage, such as in watts or volts per second. The power (or voltage) can increase or decrease as the current changes. In some examples, the linear equation can be monotonic. In some examples, one or both of a minimum value and a maximum value can be defined such that the control circuit can limit the change in power or voltage.

Figure 23:
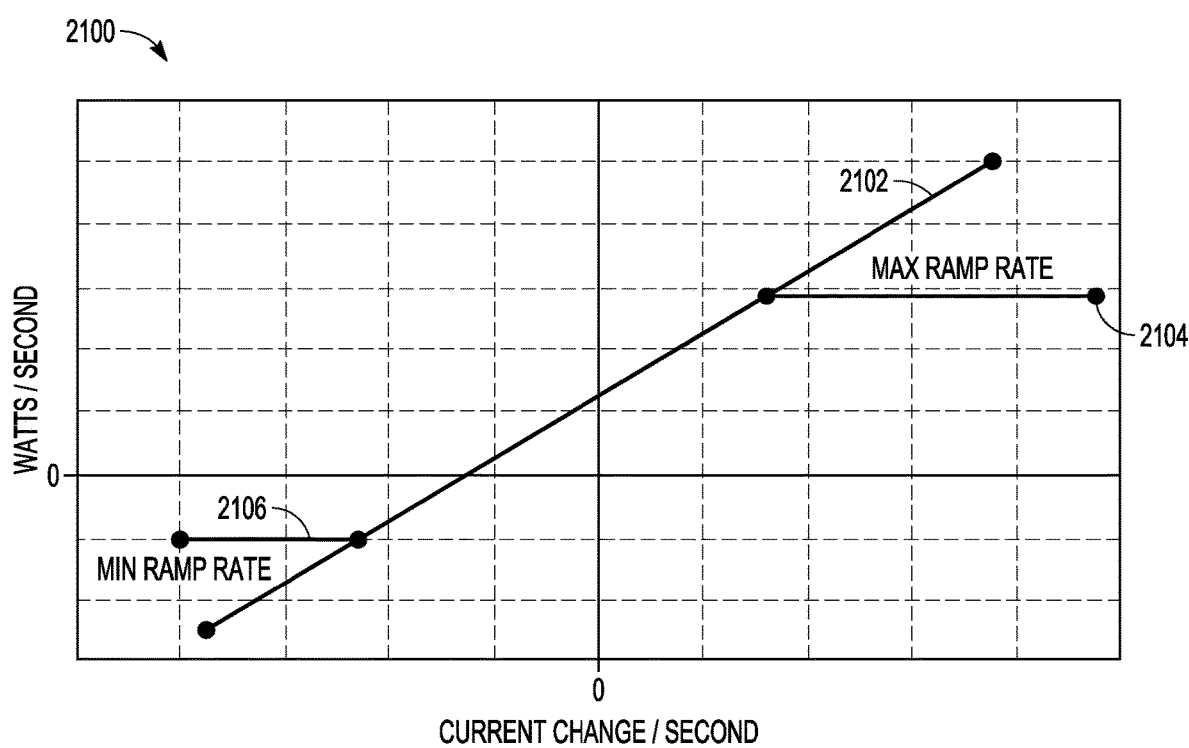
FIG. 23 is graph depicting an example of a relationship between a change in the value of a measured electrical parameter to a change in power.

FIG. 23 is graph depicting an example of a relationship between a change in the value of a measured electrical parameter to a change in power. Although depicted specifically as a change in current per unit time to a change in power in watts per unit time, the techniques described are not limited to current or power. In the example shown in FIG. 23, the y-axis of the graph 2100 can represent watts/second and the x-axis can represent the change in current/second.

In an example, the linear equation that defines the line 2102 can include an offset such that the line does not pass through the origin such that when the change in current, or delta current value, is zero the change in power is positive. For example, in the graph 2100 of a change in power versus a change in current, the line 2102 can have a positive slope and can extend through quadrants I, II, and III. As another example, in a graph of a change in voltage versus a change in current, the line can have a negative slope and can extend through quadrants I, II, and IV. In the example shown in FIG. 23, one or both of a maximum ramp rate 2104 and a minimum ramp rate 2106 can be defined such that the control circuit can limit the rate of change of power, for example.

In an example, the relationships between the change in the measured electrical parameter and the incremental change in energy can be stored in a data set, such as a look up table. The control circuit can query the stored data set, compare the change in the measured electrical parameter of the biological tissue to the stored data set, and determine the incremental change in energy delivery based on the comparison.

Whether using the function, e.g., a linear function, or the stored data set, the control circuit can monitor an electrical parameter, such as a change in current, so that the control circuit can make an adjustment in real-time (or "on the fly") to a controlling parameter, such as power or voltage, to control an energy delivery of the therapeutic signal provided to biological tissue during a portion of a therapeutic phase. In this manner, the control circuit can control the electrical power or voltage of the therapeutic signal provided to the biological tissue as a function of the change in the measured electrical parameter of the biological tissue. For example, the control circuit can incrementally modify the electrical power or voltage as a function of current.

By way of a non-limiting example, a small positive current rate change can result in a medium power rate change. As another example, a zero current rate change can result in a negative power rate change. As another example, a negative current rate change can result in a high negative power rate change. As another example, a high current rate change can result in a high power rate change. By monitoring the current delta (also referred to as a change in current), different power controls can be applied, which can drive different tissue results or be modified to accommodate different application devices.

While applying power, the current can increase because the tissue is not yet boiling and, as the tissue is heated, it becomes more electrically conductive. As such, more current is needed to increase the power. Using various techniques of this disclosure, the control circuit, such the control circuit 48 of FIG. 2, can permit the power to increase because the current is still increasing, which can desirably expedite the time it takes for the collagen denaturizing. Eventually, a condition is reached in which the power cannot be applied to the tissue any faster without tissue popping occurring. To avoid tissue popping, the control circuit can define a power (or voltage) maximum to limit the power (or voltage) applied to the tissue.

As the amount of steam increases, the impedance increases. As the impedance increases, the current decreases and the voltage increases for the same amount of power delivered (P=V*I). If the control circuit determines that steam is being generated, the control circuit can drop the power rapidly, but not so rapidly as to stop the steam from being generated. As the impedance continues to increase, the control circuit can determine the amount of energy delivered from the change in impedance. Using the determined amount of energy delivered, the control circuit can stop applying power and pause momentarily to allow the steam to collapse.

The biological tissue includes salt and when energy is applied to the tissue, the sodium can burn. The burning sodium can become highly conductive, which can skew the measurements used to determine whether to increase or decrease the power or voltage. To avoid making a real-time decision based on a minor, rapid change, such as burning sodium, the electrosurgical generator, such as the electrosurgical generator 12 of FIG. 2, can include or implement various filters. As an example, a filter can be added to the current sampling to smooth out the generator output when considering the change in current delta. The frequency of the filtering can depend on the processing speed of the generator control CPU.

In some examples, the control circuit can further determine whether the proposed power (or voltage) increase or decrease should occur. For example, the control circuit can sample the recent increase or decrease of the power (or voltage) and determine whether a continued increase (or decrease) should be continued or whether the latest change in power ramping (or voltage ramping) is noise or within expected limits. For example, if the past two (or more) power ramp values (or voltage ramp values) were positive and large, but the latest values indicate a significant negative (decrease) in power, then the control circuit can override the decision to decrease the power (or voltage) until subsequent current delta calculations are evaluated.

In some examples, the control circuit can include boundaries for the maximum allowable change and/or maximum allowable output or ramp rate, thereby preventing the generator from being limited just by its hardware or applying energy too quickly to the tissue. This can be achieved by limiting the maximum power during the stage, limiting the maximum power change (e.g., limiting the maximum watts per second ramping rate), and the like.

These power (or voltage) control techniques that can control an energy delivery of the therapeutic signal provided to biological tissue during a portion of a therapeutic phase according to an incremental change in energy delivery as a function of a change in a measured electrical parameter of the biological tissue can be used in a single ramping waveform output, or in a pulsed waveform output. An advantage of a pulsed waveform output is that the power increase quickly, if desired. For example, power can be significantly reduced (or temporarily stopped) under certain conditions to allow the steam to condense and power to be subsequently applied again in a ramping manner until a desired tissue effect "end point" has been reached.

Aspects

To further illustrate the electrosurgical techniques described above, a non-limiting list of various aspects are described below. Each of the non-limiting aspects may stand on its own, or may be combined in various permutations or combinations with one or more of the other aspects.

A. Short Circuit Error Trapping with Band Between Trigger and Escape Values

Aspect A1 can include or use subject matter (e.g., a system, apparatus, method, article, or the like) that can include or use a surgical system comprising: a control circuit; and an output circuit coupled to the control circuit and configured to deliver electrosurgical energy to an output terminal for delivery to a patient, the output terminal configured to couple to an electrosurgical device having two electrodes, wherein the control circuit is configured to: compare a first measured impedance value of biological tissue in electrical communication with the two electrodes of the electrosurgical device to a first threshold value; initiate a timer when the first measured impedance value is less than or equal to the first threshold value; compare a second measured impedance value of the tissue between the two electrodes to a second threshold value, wherein the second threshold value is greater than the first threshold value; and continue the delivery of electrosurgical energy when the second measured impedance value is less than the second threshold value and the timer has not met a time limit.

Aspect A2 can include or use or can optionally be combined with at least some features of Aspect A1 to include or use the control circuit being configured to: reduce the delivery of electrosurgical energy when the second measured impedance value is less than the second threshold value and the timer has met the time limit.

Aspect A3 can include or use or can optionally be combined with at least some features of any one or more of Aspects A1 or A2 to include or use the control circuit being configured to: generate an indication when the timer has met the time limit.

Aspect A4 can include or use or can optionally be combined with at least some features of any one or more of Aspects A1 through A3 to include or use the timer being less than 6 seconds.

Aspect A5 can include or use or can optionally be combined with at least some features of any one or more of Aspects A1 through A4 to include or use the control circuit configured to:
adjust at least one of the first threshold value, the second threshold value, and the time limit based on at least one characteristic of the electrosurgical device or based on at least one characteristic of an electrosurgical generator configured to be coupled to the electrosurgical device.

Aspect A6 can include or use or can optionally be combined with at least some features of any one or more of Aspects A1 through A5 to include or use the at least one characteristic including a surface area of at least one of the electrodes.

Aspect A7 can include or use or can optionally be combined with at least some features of any one or more of Aspects A1 through A6 to include or use the electrodes being positioned on jaws of the electrosurgical device, and where the at least one characteristic includes: a jaw force of the electrosurgical device.

Aspect A8 can include or use or can optionally be combined with at least some features of any one or more of Aspects A1 through A7 to include or use the at least one characteristic including an output current of the electrosurgical generator.

Aspect A9 can include or use or can optionally be combined with at least some features of any one or more of Aspects A1 through A8 to include or use the electrodes being positioned on jaws of the electrosurgical device, and the biological tissue being positioned between two electrodes of the electrosurgical device.

Aspect 10 can include or use a method of delivering electrical energy to an electrosurgical device, the method comprising: initiating an ongoing delivery of electrosurgical energy to biological tissue in electrical communication with two electrodes of the electrosurgical device; comparing a first measured impedance value of the tissue to a first threshold value; initiating a timer when the first measured impedance value is less than or equal to the first threshold value; comparing a second measured impedance value of the tissue to a second threshold value, wherein the second threshold value is greater than the first threshold value; and continuing the delivery of electrosurgical energy when the second measured impedance value is less than the second threshold value and the timer has not met a time limit.

Aspect A11 can include or use or can optionally be combined with at least some features of Aspect A10 to include or use reducing the delivery of electrosurgical energy when the second measured impedance value is less than the second threshold value and the timer has met the time limit.

Aspect A12 can include or use or can optionally be combined with at least some features of any one or more of Aspects A10 or A11 to include or use generating an indication when the timer has met the time limit.

Aspect A13 can include or use or can optionally be combined with at least some features of any one or more of Aspects A10 through A12 to include or use the electrodes being positioned on jaws of the electrosurgical device, and the biological tissue being positioned between two electrodes of the electrosurgical device.

Aspect A14 can include or use or can optionally be combined with at least some features of any one or more of Aspects A10 through A13, to include or use the timer being less than 6 seconds.

Aspect A15 can include or use or can optionally be combined with at least some features of any one or more of Aspects A10 through A14 to include or use adjusting at least one of the first threshold value, the second threshold value, and the time limit based on at least one characteristic of the electrosurgical device or based on at least one characteristic of an electrosurgical generator configured to be coupled to the electrosurgical device.

Aspect A16 can include or use or can optionally be combined with at least some features of any one or more of Aspects A10 through A15 to include or use the at least one characteristic of the electrosurgical device including a surface area of at least one of the electrodes.

Aspect A17 can include or use or can optionally be combined with at least some features of any one or more of Aspects A10 through A16 to include or use the electrodes being positioned on jaws of the electrosurgical device, and the at least one characteristic of the electrosurgical device including a jaw force of the electrosurgical device.

Aspect A18 can include or use or can optionally be combined with at least some features of any one or more of Aspects A10 through A17 to include or use the at least one characteristic of the electrosurgical generator including an output current of the electrosurgical generator.

B. Open Circuit Check for Resistance Limit Endpoint RF Waveform and Evaluation of Open Circuit Time in End Phase Aspect B1 can include or use subject matter (e.g., a system, apparatus, method, article, or the like) that can include or use a surgical system comprising: a control circuit; and an output circuit coupled to the control circuit and configured to deliver electrosurgical energy to an output terminal for delivery to a patient, the output terminal configured to couple to an electrosurgical device having two jaws with corresponding electrodes, wherein the control circuit is configured to: initiate a timer in response to a delivery of electrosurgical energy to biological tissue in electrical communication with two electrodes of the electrosurgical device; after the timer has met a time limit, compare a representation of impedance to a first threshold value; and continue the delivery of electrosurgical energy when the representation of impedance is less than the first threshold value.

Aspect B2 can include or use or can optionally be combined with at least some features of Aspect B1 to include or use the control circuit configured to: reduce the delivery of electrosurgical energy when the representation of impedance is greater than or equal to the first threshold value and less than a second threshold value.

Aspect B3 can include or use or can optionally be combined with at least some features of Aspects B1 or B2 to include or use the control circuit configured to: reduce the delivery of electrosurgical energy when the representation of impedance is greater than or equal to the second threshold value.

Aspect B4 can include or use or can optionally be combined with at least some features of any one or more of Aspects B1 through B3 to include or use the control circuit configured to: generate an indication when the representation of impedance is greater than or equal to the second threshold value.

Aspect B5 can include or use or can optionally be combined with at least some features of any one or more of Aspects B1 through B4 to include or use the control circuit configured to generate the indication when the representation of impedance is greater than or equal to the second threshold value is configured to: generate an audible indication.

Aspect B6 can include or use or can optionally be combined with at least some features of any one or more of Aspects B1 through B5 to include or use the control circuit configured to generate the indication when the representation of impedance is greater than or equal to the second threshold value is configured to: generate a visual indication.

Aspect B7 can include or use or can optionally be combined with at least some features of any one or more of Aspects B1 through B6 to include or use the representation of impedance including a value of the impedance.

Aspect B8 can include or use or can optionally be combined with at least some features of any one or more of Aspects B1 through B7 to include or use the representation of impedance including a change in a value of the impedance.

Aspect B9 can include or use subject matter (e.g., a system, apparatus, method, article, or the like) that can include or use a surgical system comprising: a control circuit; and an output circuit coupled to the control circuit and configured to deliver electrosurgical energy to an output terminal for delivery to a patient, the output terminal configured to couple to an electrosurgical device having two jaws with corresponding electrodes, wherein the control circuit is configured to: initiate a timer in response to a delivery of electrosurgical energy to biological tissue in electrical communication with two electrodes of the electrosurgical device; after the timer has met a time limit, compare a rate of change of impedance of the biological tissue to a first threshold value; and continue the delivery of electrosurgical energy when the rate of change of impedance is less than the first threshold value.

Aspect B10 can include or use or can optionally be combined with at least some features of Aspect B9 to include or use the control circuit is configured to: reduce delivery of the energy when the rate of change of impedance is greater than or equal to the first threshold value.

Aspect B11 can include or use or can optionally be combined with at least some features of any one or more of Aspects B9 or B10 to include or use the control circuit configured to: generate an indication when the rate of change of impedance is greater than or equal to the first threshold value.

Aspect B12 can include or use or can optionally be combined with at least some features of any one or more of Aspects B9 through B11 to include or use the control circuit configured to generate the indication when the rate of change of impedance is greater than or equal to the first threshold value is configured to: generate an indication.

Aspect B13 can include or use subject matter (e.g., a system, apparatus, method, article, or the like) that can include or use a method of delivering electrical energy to an electrosurgical device, the method comprising: initiating a timer in response to a delivery of electrosurgical energy to biological tissue in electrical communication with two electrodes of the electrosurgical device; comparing a representation of impedance of the biological tissue to a threshold value; continuing the delivery of electrosurgical energy until the threshold value is met; upon reaching the threshold value, recording an elapsed time; and declaring an error state if the elapsed time is less than a time limit.

Aspect B14 can include or use or can optionally be combined with at least some features of Aspect B13 to include or use determining a difference between first and second measured impedances and comparing the determined difference to a predetermined delta impedance value; and in response to the determined difference being equal to or greater than the predetermined delta impedance value and the timer being less than a threshold time limit, generating an error signal.

Aspect B15 can include or use or can optionally be combined with at least some features of any one or more of Aspects B13 or B14 to include or use determining a difference between first and second measured impedances and comparing the determined difference to a predetermined delta impedance value; and increasing a power ramp rate of the electrosurgical energy in response to the comparison.

Aspect B16 can include or use or can optionally be combined with at least some features of any one of or more of Aspects B13 through B15 to include or use continuing to increase the power ramp rate until either the determined difference meets or exceeds the predetermined delta impedance value or a power limit is reached.

Aspect B17 can include or use or can optionally be combined with at least some features of any one or more of Aspects B13 through B16 to include or use the power ramp rate being a first power ramp rate, and in response to reaching the power limit, adjusting the power ramp rate from the first power ramp to a second power ramp rate, wherein the second power ramp rate is slower than the first ramp rate.

Aspect B18 can include or use or can optionally be combined with at least some features of any one or more of Aspects B13 through B17 to include or use the threshold value being a first threshold value, and during a finishing phase: comparing the representation of impedance of the biological tissue to a second threshold value; and delivering the electrosurgical energy at a constant power ramp rate until the representation of impedance meets or exceeds a second threshold value.

Aspect B19 can include or use or can optionally be combined with at least some features of any one or more of Aspects B13 through B18 to include or use before the delivering the electrosurgical energy at the constant power ramp rate, delivering the electrosurgical energy at a constant power.

C. Alternate Power Correction Outputs in Low Accuracy Hardware Systems

Aspect C1 can include or use subject matter (e.g., a system, apparatus, method, article, or the like) that can include or use a surgical system comprising: a control circuit; and an output circuit coupled to the control circuit and configured to deliver electrosurgical energy to an output terminal for delivery to a patient, the output terminal configured to couple to an electrosurgical device having two jaws with corresponding electrodes, wherein the control circuit is configured to: compare a representation of an impedance of biological tissue in electrical communication with two electrodes of the electrosurgical device to a first threshold; select, from at least two power corrections, a first power correction when the representation of the impedance is within a first range; and apply the selected first power correction to a power setting of a power generator coupled the electrosurgical device.

Aspect C2 can include or use or can optionally be combined with at least some features of Aspect C1 to include or use the control circuit being configured to select, from the at least two power corrections, a second power correction when the representation of the impedance is within a second range.

Aspect C3 can include or use or can optionally be combined with at least some features of any one or more of Aspects C1 or C2 to include or use the control circuit being configured to compare a representation of at least one secondary parameter to at least one threshold; and select, from the at least two power corrections, a third power correction when the representation of the at least one secondary parameter is less than the at least one threshold.

Aspect C4 can include or use or can optionally be combined with at least some features of any one or more of Aspects C1 through C3 to include or use the at least one secondary parameter including one or more of an output current of the power generator, a tissue temperature, and a phase angle.

Aspect C5 can include or use or can optionally be combined with at least some features of any one or more of Aspects C1 through C4 to include or use the control circuit being configured to: using the corrected power setting, deliver electrosurgical energy via the electrodes of the electrosurgical device during a period of time.

Aspect C6 can include or use or can optionally be combined with at least some features of any one or more of Aspects C1 through C5 to include or use the period of time being based at least on a range of impedance values.

Aspect C7 can include or use or can optionally be combined with at least some features of any one or more of Aspects C1 through C6 to include or use the period of time being based at least on an amount of delivered electrosurgical energy.

Aspect C8 can include or use or can optionally be combined with at least some features of any one or more of Aspects C1 through C7 to include or use the control circuit being configured to: using the corrected power setting, deliver electrosurgical energy via the electrodes of the electrosurgical device; and reduce the application of the selected first power correction to the power setting when the representation of impedance meets or exceeds a second threshold.

Aspect C9 can include or use or can optionally be combined with at least some features of any one or more of Aspects C1 through C8 to include or use: using the corrected power setting, deliver electrosurgical energy via the electrodes of the electrosurgical device; and dynamically adjust at least one of an upper limit and a lower limit of the first range when the representation of the impedance is within a predetermined percentage or value of the upper or lower limit.

Aspect C10 can include or use subject matter (e.g., a system, apparatus, method, article, or the like) that can include or use a method of delivering electrical energy to an electrosurgical device, the method comprising: comparing a representation of an impedance of a biological tissue in electrical communication with two electrodes of the electrosurgical device to a first threshold; selecting, from at least two power corrections, a first power correction when the representation of the impedance is within a first range; and applying the selected first power correction to a power setting of a power generator coupled the electrosurgical device.

Aspect C11 can include or use or can optionally be combined with at least some features of Aspect C10 to include or use selecting, from the at least two power corrections, a second power correction when the representation of the impedance is within a second range.

Aspect C12 can include or use or can optionally be combined with at least some features of any one or more of Aspects C10 or C11 to include or use comparing a representation of at least one secondary parameter to at least one threshold; and selecting, from the at least two power corrections, a third power correction when the representation of the at least one secondary parameter is less than the at least one threshold.

Aspect C13 can include or use or can optionally be combined with at least some features of any one or more of Aspects C10 through C12 to include or use the at least one secondary parameter including one or more of an output current of the power generator, a tissue temperature, and a phase angle.

Aspect C14 can include or use or can optionally be combined with at least some features of any one or more of Aspects C10 through C13 to include or use: using the corrected power setting, delivering electrosurgical energy via the electrodes of the electrosurgical device during a period of time.

Aspect C15 can include or use or can optionally be combined with at least some features of any one or more of Aspects C10 through C14 to include or use the period of time being based at least on a range of impedance values.

Aspect C16 can include or use or can optionally be combined with at least some features of any one or more of Aspects C10 through C15 to include or use the period of time being based at least on an amount of delivered electrosurgical energy.

Aspect C17 can include or use or can optionally be combined with at least some features of any one or more of Aspects C10 through C16 to include or use: using the corrected power setting, delivering electrosurgical energy via the electrodes of the electrosurgical device; and reducing the application of the selected first power correction to the power setting when the representation of impedance meets or exceeds a second threshold.

Aspect C18 can include or use or can optionally be combined with at least some features of any one or more of Aspects C10 through C17 to include or use: using the corrected power setting, delivering electrosurgical energy via the electrodes of the electrosurgical device; and applying a second power correction to the power setting when the representation of the impedance is a specified percentage above an upper limit of the first range.

D. Reduced Thermal Margin Combination Energy Device

Aspect D1 can include or use subject matter (e.g., a system, apparatus, method, article, or the like) that can include or use a combination ultrasonic energy and electrosurgical energy system comprising a control circuit; and an output circuit coupled to the control circuit and configured to deliver energy to an output terminal for delivery to a patient, the output terminal configured to couple to an electrosurgical device having two jaws with corresponding electrodes, wherein the delivered energy includes at least some ultrasonic energy, wherein the control circuit is configured to: control the delivery of energy to biological tissue in electrical communication with two electrodes of the electrosurgical device; measure a representation of a tissue parameter of the biological tissue; and reduce a level of or terminate the delivery of energy based on a characteristic of the measured representation of the tissue parameter of the biological tissue, wherein the delivered energy is a combination of electrosurgical energy and ultrasonic energy, and wherein the control circuit configured to reduce the level of or terminate the delivery of energy is configured to: reduce the level of the ultrasonic energy.

Aspect D2 can include or use or can optionally be combined with at least some features of Aspect D1 to include or use the control circuit being configured to reduce the level of the ultrasonic energy is configured to: terminate the delivery of the ultrasonic energy.

Aspect D3 can include or use or can optionally be combined with at least some features of any one or more of Aspects D1 or D2 to include or use the control circuit being configured to: reduce the level of the electrosurgical energy.

Aspect D4 can include or use or can optionally be combined with at least some features of any one or more of Aspects D1 through D3 to include or use the control circuit being configured to reduce the level of the electrosurgical energy being further configured to: terminate the delivery of the electrosurgical energy.

Aspect D5 can include or use or can optionally be combined with at least some features of any one or more of Aspects D1 through D4 to include or use the delivered energy being a combination of electrosurgical energy and ultrasonic energy, and the electrosurgical energy being power-controlled.

Aspect D6 can include or use or can optionally be combined with at least some features of any one or more of Aspects D1 through D5 to include or use the delivered energy being a combination of electrosurgical energy and ultrasonic energy, and the electrosurgical energy being voltage-controlled.

Aspect D7 can include or use or can optionally be combined with at least some features of any one or more of Aspects D1 through D6 to include or use the measured representation of the tissue parameter being an impedance value, and the control circuit being configured to: compare the impedance value to a threshold value; and reduce the level of the ultrasonic energy based on the comparison.

Aspect D8 can include or use or can optionally be combined with at least some features of any one or more of Aspects D1 through D7 to include or use the measured representation of the tissue parameter being a change in impedance, the method comprising: compare the change in impedance to a threshold value; and reduce the level of the ultrasonic energy based on the comparison.

Aspect D9 can include or use subject matter (e.g., a system, apparatus, method, article, or the like) that can include or use a method of delivering energy to a combination ultrasonic energy and electrosurgical energy device, the method comprising: delivering energy to a biological tissue in electrical communication with two electrodes of an electrosurgical device, wherein the delivered energy includes at least some ultrasonic energy; measuring a representation of a tissue parameter of the biological tissue; and reducing a level of or terminating the delivery of the energy based upon a characteristic of the measured representation of the tissue parameter, wherein the delivered energy is a combination of electrosurgical energy and ultrasonic energy, and wherein reducing the level of or terminating the delivery of energy includes: reducing the level of the ultrasonic energy.

Aspect D10 can include or use or can optionally be combined with at least some features of Aspect D9 to include or use reducing the level of the ultrasonic energy including terminating the delivery of the ultrasonic energy.

Aspect D11 can include or use or can optionally be combined with at least some features of any one or more of Aspects D9 or D10 to include or use reducing the level of the electrosurgical energy.

Aspect D12 can include or use or can optionally be combined with at least some features of any one or more of Aspects D9 through D11 to include or use reducing the level of the electrosurgical energy including terminating the delivery of the electrosurgical energy.

Aspect D13 can include or use or can optionally be combined with at least some features of any one or more of Aspects D9 through D12 to include or use the delivered energy being a combination of electrosurgical energy and ultrasonic energy, and the electrosurgical energy being power-controlled.

Aspect D14 can include or use or can optionally be combined with at least some features of any one or more of Aspects D9 through D13 to include or use the delivered energy being a combination of electrosurgical energy and ultrasonic energy, and the electrosurgical energy being voltage-controlled.

Aspect D15 can include or use or can optionally be combined with at least some features of any one or more of Aspects D9 through D14 to include or use the measured representation of the tissue parameter being an impedance value, the method comprising: comparing the impedance value to a threshold value; and reducing the level of the ultrasonic energy based on the comparison.

Aspect D16 can include or use or can optionally be combined with at least some features of any one or more of Aspects D9 through D15 to include or use the measured representation of the tissue parameter being a change in impedance, the method comprising: comparing the change in impedance to a threshold value; and reducing the level of the ultrasonic energy based on the comparison.

E. Staged Resistance Values to Control Thermal Margins in Systems with Slow CPUs Aspect E1 can include or use subject matter (e.g., a system, apparatus, method, article, or the like) that can include or use a surgical system comprising: a control circuit; and an output circuit coupled to the control circuit and configured to deliver energy to an output terminal for delivery to a patient, the output terminal configured to couple to an electrosurgical device with at least one electrode, wherein the control circuit is configured to: count and deliver electrosurgical energy pulses to biological tissue in communication with the at least one electrode; and for a plurality of electrosurgical energy pulses: compare a parameter to a threshold value; and adjust the threshold value based on the count of the electrosurgical energy pulse.

Aspect E2 can include or use or can optionally be combined with at least some features of Aspect E1 to include or use the parameter being selected from the group consisting of: an impedance of the biological tissue, a change in impedance of the biological tissue, a rate of change of the impedance of the biological tissue, a change in a phase angle, a change in a current of the delivered electrosurgical energy pulse, and a change in an output voltage of the delivered electrosurgical energy pulse.

Aspect E3 can include or use or can optionally be combined with at least some features of any one or more of Aspects E1 or E2 to include or use the control circuit being configured to: retrieve data representing the threshold value from a memory device.

Aspect E4 can include or use or can optionally be combined with at least some features of any one or more of Aspects E1 through E3 to include or use the control circuit being configured to: compare a first measured parameter to a second measured parameter, and wherein the control circuit configured to adjust the threshold value based on the count of the electrosurgical energy pulse is configured to: adjust the threshold value based on a difference between the first measured parameter and the second measured parameter.

Aspect E5 can include or use or can optionally be combined with at least some features of any one or more of Aspects E1 through E4 to include or use the control circuit being configured to: compare a first measured parameter to a second measured parameter, and wherein the control circuit configured to adjust the threshold value based on the count of the electrosurgical energy pulse is configured to: adjust the threshold value based on the first measured parameter being greater than the second measured parameter.

Aspect E6 can include or use or can optionally be combined with at least some features of any one or more of Aspects E1 through E5 to include or use the control circuit being configured to: compare a first measured parameter to a second measured parameter, and wherein the control circuit configured to adjust the threshold value based on the count of the electrosurgical energy pulse is configured to: adjust the threshold value based on the first measured parameter being less than the second measured parameter.

Aspect E7 can include or use or can optionally be combined with at least some features of any one or more of Aspects E1 through E6 to include or use the control circuit being configured to: determine a rate of change between a first measured parameter and a second measured parameter, and wherein the control circuit is configured to adjust the threshold value based on the count of the electrosurgical energy pulse is configured to: adjust the threshold value based on the rate of change between the first measured parameter and a second measured parameter.

Aspect E8 can include or use or can optionally be combined with at least some features of any one or more of Aspects E1 through E7 to include or use the control circuit being configured to: adjust the threshold value based on the parameter.

Aspect E9 can include or use or can optionally be combined with at least some features of any one or more of Aspects E1 through E8 to include or use the control circuit being configured to: reduce the delivery of the plurality of electrosurgical energy pulses when a measured representation of impedance meets or exceeds an endpoint value.

Aspect E10 can include or use subject matter (e.g., a system, apparatus, method, article, or the like) that can include or use a surgical system comprising: a control circuit; and an output circuit coupled to the control circuit and configured to deliver energy to an output terminal for delivery to a patient, the output terminal configured to couple to an electrosurgical device having two jaws with corresponding electrodes, wherein the control circuit is configured to: count and deliver electrosurgical energy pulses to biological tissue in electrical communication with two electrodes of the surgical device; and for a plurality of electrosurgical energy pulses: deliver a first electrosurgical energy pulse to biological tissue in electrical communication with two electrodes of the electrosurgical device; compare a first measured representation of impedance of the biological tissue to a first threshold value; reduce delivery of the first electrosurgical energy pulse when the first measured representation of impedance meets or exceeds the first threshold value; increase the first threshold value to a second threshold value based on the count of the pulse; deliver a second electrosurgical energy pulse to the tissue; compare a second measured representation of impedance of the tissue to the second threshold value; and reduce delivery of the second electrosurgical energy pulse when the second measured representation of impedance meets or exceeds the second threshold value.

Aspect E11 can include or use or can optionally be combined with at least some features of Aspect E10 to include or use the control circuit being configured to: retrieve data representing the first and second threshold values from a memory device.

Aspect E12 can include or use or can optionally be combined with at least some features of any one or more of Aspects E10 or E11 to include or use the control circuit being configured to: compare the first measured representation of impedance to the second measured representation of impedance; and determine the second threshold value based on a difference between the first measured representation of impedance and the second measured representation of impedance.

Aspect E13 can include or use or can optionally be combined with at least some features of any one or more of Aspects E10 through E12 to include or use the control circuit being configured to: compare the first measured representation of impedance to the second measured representation of impedance; and determine the second threshold value based on the first measured representation of impedance being greater than the second measured representation of impedance.

Aspect E14 can include or use or can optionally be combined with at least some features of any one or more of Aspects E10 through E13 to include or use the control circuit being configured to: compare the first measured representation of impedance to the second measured representation of impedance; and determine the second threshold value based on the first measured representation of impedance being less than the second measured representation of impedance.

Aspect E15 can include or use or can optionally be combined with at least some features of any one or more of Aspects E10 through E14 to include or use the control circuit being configured to: determine a rate of change between the first measured representation of impedance and the second measured representation of impedance; and determine the second threshold value based on the rate of change.

Aspect E16 can include or use or can optionally be combined with at least some features of any one or more of Aspects E10 through E15 to include or use the control circuit being configured to: determine the second threshold value based on the first measured representation of impedance.

Aspect E17 can include or use subject matter (e.g., a system, apparatus, method, article, or the like) that can include or use a method of delivering electrical energy to an electrosurgical device, the method comprising: counting and delivering a plurality of electrosurgical energy pulses to biological tissue in electrical communication with two electrodes of the electrosurgical device; for a plurality of electrosurgical energy pulses: comparing a parameter to a threshold value; and adjusting the threshold value based on the count of the electrosurgical energy pulses.

Aspect E18 can include or use or can optionally be combined with at least some features of Aspect E17 to include or use the parameter being selected from the group consisting of: an impedance of the biological tissue, a change in impedance of the biological tissue, a rate of change of the impedance of the biological tissue, a change in a phase angle, a change in a current of the delivered electrosurgical energy pulse, and a change in an output voltage of the delivered electrosurgical energy pulse.

Aspect E19 can include or use or can optionally be combined with at least some features of any one or more of Aspects E17 or E18 to include or use retrieving data representing the threshold value from a memory device.

Aspect E20 can include or use or can optionally be combined with at least some features of any one or more of Aspects E17 through E19 to include or use comparing a first measured parameter to a second measured parameter, wherein adjusting the threshold value based on the count of the electrosurgical energy pulse includes: adjusting the threshold value based on a difference between the first measured parameter and the second measured parameter.

Aspect E21 can include or use or can optionally be combined with at least some features of any one or more of Aspects E17 through E20 to include or use comparing a first measured parameter to a second measured parameter, wherein adjusting the threshold value based on the count of the electrosurgical energy pulse includes: adjusting the threshold value based on the first measured parameter being greater than the second measured parameter.

Aspect E22 can include or use or can optionally be combined with at least some features of any one or more of Aspects E17 through E21 to include or use comparing a first measured parameter to a second measured parameter, wherein adjusting the threshold value based on the count of the electrosurgical energy pulse includes: adjusting the threshold value based on the first measured parameter being less than the second measured parameter.

Aspect E23 can include or use or can optionally be combined with at least some features of any one or more of Aspects E17 through E22 to include or use determining a rate of change between a first measured parameter and a second measured parameter, wherein adjusting the threshold value based on the count of the electrosurgical energy pulse includes: adjusting the threshold value based on the rate of change between the first measured parameter and a second measured parameter.

Aspect E24 can include or use or can optionally be combined with at least some features of any one or more of Aspects E17 through E23 to include or use adjusting the threshold value based on the parameter.

Aspect E25 can include or use or can optionally be combined with at least some features of any one or more of Aspects E17 through E24 to include or use reducing the delivery of the plurality of electrosurgical energy pulses when a measured representation of impedance meets or exceeds an endpoint value.

F. Power-Controlled Waveform

Aspect F1 can include or use subject matter (e.g., a system, apparatus, method, article, or the like) that can include or use a surgical generator configured to generate and provide controlled electrical power of a therapeutic signal to biological tissue in electrical communication with an instrument, the surgical generator comprising: a control circuit in communication with an electrical-energy source, the electrical-energy source electrically coupled to the instrument and configured to generate the therapeutic signal, the control circuit configured to: control the electrical power of the therapeutic signal provided to the biological tissue during a portion of a therapeutic phase according to a therapeutic plan.

Aspect F2 can include or use or can optionally be combined with at least some features of Aspect F1 to include or use the control circuit being configured to control a voltage of the therapeutic signal provided to the biological tissue during a portion of a drying phase according to the therapeutic plan.

Aspect F3 can include or use or can optionally be combined with at least some features of any one or more of Aspects F1 or F2 to include or use the control circuit being configured to: monitor the voltage of the therapeutic signal; and maintain the voltage when the voltage meets a voltage threshold.

Aspect F4 can include or use or can optionally be combined with at least some features of any one or more of Aspects F1 through F3 to include or use the control circuit being configured to: control the electrical power of the therapeutic signal provided to the biological tissue during the portion of the therapeutic phase using a pre-defined power curve.

Aspect F5 can include or use or can optionally be combined with at least some features of any one or more of Aspects F1 through F4 to include or use the pre-defined power curve including a linear portion.

Aspect F6 can include or use or can optionally be combined with at least some features of any one or more of Aspects F1 through F5 to include or use the pre-defined power curve including two or more linear portions.

Aspect F7 can include or use or can optionally be combined with at least some features of any one or more of Aspects F1 through F6 to include or use the control circuit configured to control the electrical power of the therapeutic signal provided to the biological tissue being configured to: incrementally modify the electrical power as a function of current.

Aspect F8 can include or use or can optionally be combined with at least some features of any one or more of Aspects F1 through F7 to include or use the function of current being a function of an instantaneous measured change in current.

Aspect F9 can include or use or can optionally be combined with at least some features of any one or more of Aspects F1 through F8 to include or use the control circuit configured to control the electrical power of the therapeutic signal provided to the biological tissue being configured to: incrementally modify the electrical power as a function of resistance.

Aspect F10 can include or use subject matter (e.g., a system, apparatus, method, article, or the like) that can include or use a method of delivering controlled electrical power of a therapeutic signal to biological tissue in electrical communication with an instrument, the method comprising: generating, using an electrical-energy source electrically coupled to the instrument, the therapeutic signal; and controlling the electrical power of the therapeutic signal provided to the biological tissue during a portion of the therapeutic phase according to a therapeutic plan.

Aspect F11 can include or use or can optionally be combined with at least some features of Aspect F10 to include or use controlling a voltage of the therapeutic signal provided to the biological tissue during a portion of a drying phase according to the therapeutic plan.

Aspect F12 can include or use or can optionally be combined with at least some features of any one or more of Aspects F10 or F11 to include or use monitoring the voltage of the therapeutic signal; and maintaining the voltage when the voltage meets a voltage threshold.

Aspect F13 can include or use or can optionally be combined with at least some features of any one or more of Aspects F10 through F12 to include or use controlling the electrical power of the therapeutic signal provided to the biological tissue during the portion of the therapeutic phase using a pre-defined power curve.

Aspect F14 can include or use or can optionally be combined with at least some features of any one or more of Aspects F10 through F13 to include or use the pre-defined power curve including a linear portion.

Aspect F15 can include or use or can optionally be combined with at least some features of any one or more of Aspects F10 through F14 to include or use the pre-defined power curve including two or more linear portions.

Aspect F16 can include or use or can optionally be combined with at least some features of any one or more of Aspects F10 through F15 to include or use incrementally modifying the electrical power as a function of current.

Aspect F17 can include or use or can optionally be combined with at least some features of any one or more of Aspects F10 through F16 to include or use the function of current being a function of an instantaneous measured change in current.

Aspect F18 can include or use or can optionally be combined with at least some features of any one or more of Aspects F10 through F17 to include or use the function of the instantaneous measured change in current being a linear function.

Aspect F19 can include or use or can optionally be combined with at least some features of any one or more of Aspects F10 through F18 to include or use incrementally modifying the electrical power as a function of resistance.

G. Incremental Adjustment of Control Parameter as a Function of a Monitored Variable Aspect G1 can include or use subject matter (e.g., a system, apparatus, method, article, or the like) that can include or use a surgical generator configured to generate and provide controlled electrical power of a therapeutic signal to biological tissue in electrical communication with an instrument, the surgical generator comprising: a control circuit in communication with an electrical-energy source, the electrical-energy source electrically coupled to the instrument and configured to generate the therapeutic signal, the control circuit configured to: control an energy delivery of the therapeutic signal provided to the biological tissue during a portion of a therapeutic phase according to an incremental change in energy delivery as a function of a change in a measured electrical parameter of the biological tissue.

Aspect G2 can include or use or can optionally be combined with at least some features of Aspect G1 to include or use the control circuit configured to control the energy deliver of the therapeutic signal being configured to: control the electrical power of the therapeutic signal provided to the biological tissue.

Aspect G3 can include or use or can optionally be combined with at least some features of any one or more of Aspects G1 or G2 to include or use the control circuit configured to control the electrical power of the therapeutic signal provided to the biological tissue being configured to: incrementally modify the electrical power as a function of current.

Aspect G4 can include or use or can optionally be combined with at least some features of any one or more of Aspects G1 through G3 to include or use the control circuit configured to control the energy deliver of the therapeutic signal being configured to: control a voltage of the therapeutic signal provided to the biological tissue.

Aspect G5 can include or use or can optionally be combined with at least some features of any one or more of Aspects G1 through G4 to include or use the control circuit configured to control the electrical power of the therapeutic signal provided to the biological tissue being configured to: incrementally modify the voltage as a function of current.

Aspect G6 can include or use or can optionally be combined with at least some features of any one or more of Aspects G1 through G5 to include or use the measured electrical parameter including a change in impedance.

Aspect G7 can include or use or can optionally be combined with at least some features of any one or more of Aspects G1 through G6 to include or use the measured electrical parameter including a change in current.

Aspect G8 can include or use or can optionally be combined with at least some features of any one or more of Aspects G1 through G7 to include or use the control circuit being configured to: compare the change in the measured electrical parameter of the biological tissue to a stored data set; and determine the incremental change in energy delivery based on the comparison.

H. Terminating Drying Cycles by Monitoring Impedance

Aspect H1 can include or use subject matter (e.g., a system, apparatus, method, article, or the like) that can include or use a surgical generator configured to generate and provide controlled electrical power of a therapeutic signal to biological tissue in electrical communication with a surgical instrument, the surgical generator comprising: a measurement circuit coupled to a control circuit and configured to measure an impedance of the biological tissue during a therapeutic phase; the control circuit in communication with an electrical-energy source, the electrical-energy source electrically coupled to the instrument and configured to generate the therapeutic signal, the control circuit configured to: control an energy delivery of the therapeutic signal provided to the biological tissue during a therapeutic phase; and in response to the measured impedance changing by a predetermined delta impedance value, reduce the energy delivery during the therapeutic phase, wherein the predetermined delta impedance is a change in impedance relative to a minimum impedance measurement during a pulse of the therapeutic signal.

Aspect H2 can include or use or can optionally be combined with at least some features of Aspect H1 to include or use the control circuit being configured to: control an electrical power of the therapeutic signal provided to the biological tissue.

Aspect H3 can include or use or can optionally be combined with at least some features of any one or more of Aspects H1 or H2 to include or use the control circuit being configured to: control a voltage of the therapeutic signal provided to the biological tissue.

Aspect H4 can include or use or can optionally be combined with at least some features of any one or more of Aspects H1 through H3 to include or use the control circuit being configured to: monitor the voltage of the therapeutic signal; and maintain the voltage when the voltage meets a voltage threshold.

Aspect H5 can include or use or can optionally be combined with at least some features of any one or more of Aspects H1 through H4 to include or use the therapeutic phase being a drying phase.

Aspect H6 can include or use or can optionally be combined with at least some features of any one or more of Aspects H1 through H5 to include or use the measurement circuit being configured to: measure a first impedance conducted by the biological tissue and measure a second impedance conducted by the biological tissue during the drying phase; wherein the control circuit is configured to: control the electrical-energy source to provide a drying signal to the biological tissue during the drying phase; and reduce the drying phase in response to a comparison between first impedance and the second impedance indicating a phase change of liquid in the biological tissue.

Aspect H7 can include or use or can optionally be combined with at least some features of any one or more of Aspects H1 through H6 to include or use the control circuit being configured to control the drying signal according to a drying schedule.

Aspect H8 can include or use or can optionally be combined with at least some features of any one or more of Aspects H1 through H7 to include or use the measurement circuit being configured to measure the impedance conducted by the biological tissue during the drying phase.

Aspect H9 can include or use or can optionally be combined with at least some features of any one or more of Aspects H1 through H8 to include or use the control circuit being configured to: compare the measured impedance to the minimum impedance measurement; and store the measured impedance as the minimum impedance measurement when the measured impedance is less than the minimum impedance measurement.

Aspect H10 can include or use subject matter (e.g., a system, apparatus, method, article, or the like) that can include or use a surgical generator configured to generate and provide controlled electrical power of a therapeutic signal to biological tissue in electrical communication with a surgical instrument, the surgical generator comprising: a measurement circuit coupled to a control circuit and configured to measure an impedance of the biological tissue during a therapeutic phase; the control circuit in communication with an electrical-energy source, the electrical-energy source electrically coupled to the instrument and configured to generate the therapeutic signal, the control circuit configured to: control an energy delivery of the therapeutic signal provided to the biological tissue during a therapeutic phase; and in response to the measured impedance changing by a predetermined delta impedance value, reduce the energy delivery during the therapeutic phase, wherein the predetermined delta impedance is a change in impedance relative to an impedance measurement taken at a set time interval after the therapeutic phase has begun.

I. Terminating Drying Cycles by Monitoring Current, and Current in One Phase and Impedance in One Phase Aspect I1 can include or use subject matter (e.g., a system, apparatus, method, article, or the like) that can include or use a surgical generator configured to generate and provide controlled electrical power of a therapeutic signal to biological tissue in electrical communication with a surgical instrument, the surgical generator comprising: a measurement circuit coupled to a control circuit and configured to measure a current provided to the biological tissue during a therapeutic phase; the control circuit in communication with an electrical-energy source, the electrical-energy source electrically coupled to the instrument and configured to generate the therapeutic signal, the control circuit configured to: control an energy delivery of the therapeutic signal provided to the biological tissue during a therapeutic phase; and in response to the measured electrical current of the biological tissue satisfying a predetermined value, reduce the energy delivery during the therapeutic phase.

Aspect I2 can include or use or can optionally be combined with at least some features of Aspect C10 to include or use the predetermined value being an absolute current threshold value.

Aspect I3 can include or use or can optionally be combined with at least some features of any one or more of Aspects I1 or I2 to include or use the predetermined value is a change in current relative to an initial current measurement.

Aspect I4 can include or use or can optionally be combined with at least some features of any one or more of Aspects I1 through I3 to include or use the predetermined value being a change in current relative to a maximum current measurement during a pulse of the therapeutic signal.

Aspect I5 can include or use or can optionally be combined with at least some features of any one or more of Aspects I1 through I4 to include or use the control circuit being configured to: control an electrical power of the therapeutic signal provided to the biological tissue.

Aspect I6 can include or use or can optionally be combined with at least some features of any one or more of Aspects I1 through I5 to include or use the control circuit being configured to control a voltage of the therapeutic signal provided to the biological tissue.

Aspect I7 can include or use or can optionally be combined with at least some features of any one or more of Aspects I1 through I6 to include or use the therapeutic phase being a drying phase.

Aspect I8 can include or use or can optionally be combined with at least some features of any one or more of Aspects I1 through I7 to include or use the measurement circuit being configured to: measure a first electrical current conducted by the biological tissue and measure a second electrical current conducted by the biological tissue during the drying phase; and wherein the control circuit is configured to control the electrical-energy source to provide a drying signal to the biological tissue during the drying phase; and reduce the drying signal in response to a ratio of the measured first electrical current to the measured second electrical current exceeding a predetermined factor indicating a phase change of liquid in the biological tissue.

Aspect I9 can include or use or can optionally be combined with at least some features of any one or more of Aspects I1 through I8 to include or use the control circuit being configured to control the drying signal according to a drying schedule.

Aspect I10 can include or use or can optionally be combined with at least some features of any one or more of Aspects I1 through I9 to include or use the drying schedule being a monotonically-increasing electrical-power schedule.

Aspect I11 can include or use or can optionally be combined with at least some features of any one or more of Aspects I1 through I10 to include or use the measurement circuit being configured to measure electrical current conducted by the biological tissue during the drying phase.

Aspect I12 can include or use subject matter (e.g., a system, apparatus, method, article, or the like) that can include or use a surgical generator configured to generate and provide controlled electrical power of a therapeutic signal to biological tissue in electrical communication with a surgical instrument, the surgical generator comprising: a measurement circuit coupled to a control circuit and configured to measure first and second electrical parameters of the biological tissue during first and second pulses, respectively, of the plurality of therapeutic pulses; the control circuit in communication with an electrical-energy source, the electrical-energy source electrically coupled to the instrument and configured to generate the therapeutic signal, the control circuit configured to: control an energy delivery of the therapeutic signal provided to the biological tissue during a plurality of therapeutic pulses; in response to the measured first electrical parameter of the biological tissue meeting a first threshold value, modify the energy delivery during the first pulse; and in response to the measured second parameter of the biological tissue meeting a second threshold value, modify the energy delivery during the second pulse.

Aspect I13 can include or use or can optionally be combined with at least some features of Aspect I12 to include or use the first phase being during a drying phase.

Aspect I14 can include or use or can optionally be combined with at least some features of any one or more of Aspects I12 or I13 to include or use the first parameter being a current, and wherein the first threshold value is a change in current relative to an initial current measurement.

Aspect I15 can include or use or can optionally be combined with at least some features of any one or more of Aspects I12 through I14 to include or use the first parameter being a current, and wherein the first threshold value is a change in current relative to a maximum current measurement during the first pulse.

Aspect I16 can include or use or can optionally be combined with at least some features of any one or more of Aspects I12 through I15 to include or use the second phase being a sealing phase.

Aspect I17 can include or use or can optionally be combined with at least some features of any one or more of Aspects I12 through I16 to include or use the second parameter being an impedance.

Aspect I18 can include or use or can optionally be combined with at least some features of any one or more of Aspects I12 through I17 to include or use the control circuit being configured to control an electrical power of the therapeutic signal provided to the biological tissue.

Aspect I19 can include or use or can optionally be combined with at least some features of any one or more of Aspects I12 through I18 to include or use the control circuit being configured to control a voltage of the therapeutic signal provided to the biological tissue.

J. Evaluation of Consumed Energy

Aspect J1 can include or use subject matter (e.g., a system, apparatus, method, article, or the like) that can include or use a surgical generator configured to generate and provide a therapeutic signal to biological tissue in electrical communication with a surgical instrument, the surgical generator comprising: a control circuit in communication with an electrical-energy source, the electrical-energy source electrically coupled to the instrument and configured to generate the therapeutic signal, the control circuit configured to: control an energy delivery of the therapeutic signal provided to the biological tissue during at least one of an interrogation phase and a first drying phase; after completion of at least the first drying phase, compare an amount of energy delivered to the biological tissue during the at least one of the interrogation and the first drying phase to a threshold energy value; and adjust delivery of the therapeutic signal based on the comparison.

Aspect J2 can include or use or can optionally be combined with at least some features of Aspect J1 to include or use the control circuit being configured to control an electrical power of the therapeutic signal provided to the biological tissue.

Aspect J3 can include or use or can optionally be combined with at least some features of any one or more of Aspects J1 or J2 to include or use the control circuit being configured to control a voltage of the therapeutic signal provided to the biological tissue.

Aspect J4 can include or use or can optionally be combined with at least some features of any one or more of Aspects J1 through J3 to include or use the control circuit configured to adjust delivery of the therapeutic signal based on the comparison being configured to control the energy delivery of the therapeutic signal provided to the biological tissue during a second drying phase if the amount of energy delivered exceeds the threshold energy value.

Aspect J5 can include or use or can optionally be combined with at least some features of any one or more of Aspects J1 through J4 to include or use the control circuit configured to adjust delivery of the therapeutic signal based on the comparison being configured to: control the energy delivery of the therapeutic signal provided to the biological tissue during a finishing phase if the amount of energy delivered is less than the threshold energy value.

Aspect J6 can include or use or can optionally be combined with at least some features of any one or more of Aspects J1 through J5 to include or use a measurement circuit coupled to the control circuit and configured to measure an impedance of the biological tissue; wherein the control circuit is configured to: determine a power ramp rate for delivery of the therapeutic signal based on the measured impedance.

Aspect J7 can include or use or can optionally be combined with at least some features of any one or more of Aspects J1 through J6 to include or use the control circuit being configured to: determine a difference between first and second measured impedances; and adjust the power ramp rate in response to the determined difference being less than a predetermined delta impedance value.

Aspect J8 can include or use or can optionally be combined with at least some features of any one or more of Aspects J1 through J7 to include or use the control circuit configured to adjust the power ramp rate in response to the determined difference being less than the predetermined delta impedance value being configured to increase the power ramp rate until either the determined difference is equal to or greater than the predetermined delta impedance value or the amount of energy delivered is equal to or greater than the threshold energy value.

Aspect J9 can include or use or can optionally be combined with at least some features of any one or more of Aspects J1 through J8 to include or use a measurement circuit coupled to the control circuit and configured to measure an impedance of the biological tissue; wherein the control circuit is configured to: during a finishing phase: initiate a timer; determine a difference between measured impedances and compare the determined difference to a predetermined delta impedance value; in response to the determined difference being equal to or greater than the predetermined delta impedance value and the timer being greater than a threshold time limit, generate an error signal.

Aspect J10 can include or use or can optionally be combined with at least some features of any one or more of Aspects J1 through J9 to include or use the error signal being an open circuit error signal.

Aspect J11 can include or use or can optionally be combined with at least some features of any one or more of Aspects J1 through J10 to include or use the control circuit configured to adjust delivery of the therapeutic signal based on the comparison being configured to repeat a drying phase.

Aspect J12 can include or use subject matter (e.g., a system, apparatus, method, article, or the like) that can include or use a surgical generator configured to generate and provide a therapeutic signal to biological tissue in electrical communication with a surgical instrument, the surgical generator comprising: a control circuit in communication with an electrical-energy source, the electrical-energy source electrically coupled to the instrument and configured to generate the therapeutic signal, the control circuit configured to: control an energy delivery of the therapeutic signal provided to the biological tissue during at least one of an interrogation phase and a first drying phase; after completion of at least the first drying phase, compare an amount of current delivered to the biological tissue during the at least one of the interrogation and the first drying phase to a threshold energy value; and adjust delivery of the therapeutic signal based on the comparison.

K. Phase Angle Measurement

Aspect K1 can include or use subject matter (e.g., a system, apparatus, method, article, or the like) that can include or use an electrosurgical generator configured to generate and provide a therapeutic signal to biological tissue in electrical communication with a surgical instrument, the surgical generator comprising: a measurement circuit coupled to a control circuit and configured to measure a reference impedance angle of the biological tissue during an interrogation phase; and the control circuit in communication with an electrical-energy source, the electrical-energy source electrically coupled to the instrument and configured to generate the therapeutic signal, the control circuit configured to: control delivery of the therapeutic signal provided to the biological tissue; compare the measured reference impedance angle with an angle threshold; and generate a response indicative of an environmental condition of the instrument based on the comparison of the measured reference impedance angle with the angle threshold.

Aspect K2 can include or use or can optionally be combined with at least some features of Aspect K1 to include or use the measured reference impedance angle is substantially equal to an angular difference between a voltage across and current conducted by the biological tissue as measured by the measurement circuit.

Aspect K3 can include or use or can optionally be combined with at least some features of any one or more of Aspects K1 or K2 to include or use the angle threshold is a first angle threshold, and wherein the control circuit configured to generate the response indicative of the environmental condition of the instrument is configured to: in response to the measured reference impedance angle being greater than the first angle threshold, reduce the delivery of the therapeutic signal and generate a notification signal.

Aspect K4 can include or use or can optionally be combined with at least some features of any one or more of Aspects K1 through K3 to include or use the error notification indicating a presence of a conductive foreign body in the biological tissue.

Aspect K5 can include or use or can optionally be combined with at least some features of any one or more of Aspects K1 through K4 to include or use the angle threshold being a first angle threshold, and wherein the control circuit configured to generate the response indicative of the environmental condition of the instrument is configured to: in response to the measured reference impedance angle being greater than a first angle and less than a second angle, reduce a power level of the therapeutic signal.

Aspect K6 can include or use or can optionally be combined with at least some features of any one or more of Aspects K1 through K5 to include or use the angle threshold being a first angle threshold, and wherein the control circuit is configured to: in response to the measured reference impedance angle being less than the first angle threshold, reduce the delivery of the therapeutic signal.

Aspect K7 can include or use or can optionally be combined with at least some features of any one or more of Aspects K1 through K6 to include or use the error notification indicating an open circuit.

Aspect K8 can include or use or can optionally be combined with at least some features of any one or more of Aspects K1 through K7 to include or use a timer to measure an elapsed therapy time, wherein the control circuit is configured to: compare the elapsed therapy time to a time constant; and in response to the elapsed therapy time exceeding the time constant, the measurement circuit is configured to measure the reference impedance angle of the biological tissue.

L. Correction to Measured Tissue Resistance to Account for Electrode Temperature Aspect L1 can include or use subject matter (e.g., a system, apparatus, method, article, or the like) that can include or use a method of delivering electrical energy to an electrosurgical device, the method comprising: delivering an electrotherapeutic signal to biological tissue to the electrosurgical device; measuring an impedance of the biological tissue; measuring an electrosurgical device sealing parameter; and determining an adjusted impedance based on a relationship between the electrosurgical device sealing parameter and the measured impedance.

Aspect L2 can include or use or can optionally be combined with at least some features of Aspect L1 to include or use the electrosurgical device sealing parameter including a temperature.

Aspect L3 can include or use or can optionally be combined with at least some features of any one or more of Aspects L1 or L2 to include or use the electrosurgical device including jaws, and wherein the temperature is a temperature of the jaws.

Aspect L4 can include or use or can optionally be combined with at least some features of any one or more of Aspects L1 through L3 to include or use wherein determining the adjusted impedance based on the relationship between the electrosurgical device sealing parameter and the measured impedance includes: comparing the electrosurgical device sealing parameter and the measured impedance to a stored data set; and determining the adjusted impedance based on the comparison.

Aspect L5 can include or use or can optionally be combined with at least some features of any one or more of Aspects L1 through L4 to include or use determining a vessel size using the determined adjusted impedance.

Aspect L6 can include or use or can optionally be combined with at least some features of any one or more of Aspects L1 through L5 to include or use determining at least one electrical parameter of an electrosurgical signal for delivery to the biological tissue.

Aspect L7 can include or use or can optionally be combined with at least some features of any one or more of Aspects L1 through L6 to include or use the electrosurgical device sealing parameter including an elapsed time after delivery of the electrotherapeutic signal.

M. Dwell Time Between Pulses

Aspect M1 can include or use subject matter (e.g., a system, apparatus, method, article, or the like) that can include or use a surgical system comprising: a control circuit; and an output circuit coupled to the control circuit and configured to deliver energy to an output terminal for delivery to a patient, the output terminal configured to couple to an electrosurgical device having two jaws with corresponding electrodes, wherein the control circuit is configured to: deliver first and second electrosurgical energy pulses to biological tissue in electrical communication with two electrodes of the surgical device, wherein the first and second electrosurgical energy pulses are separated from one another by a dwell time; and determine the dwell time following the first electrosurgical energy pulse.

Aspect M2 can include or use or can optionally be combined with at least some features of Aspect M1 to include or use the control circuit configured to determine the dwell time following the first electrosurgical energy pulse being configured to: determine an amount of energy delivered to the jaws; and determine the dwell time following the first electrosurgical energy pulse based on the determined amount of energy.

Aspect M3 can include or use or can optionally be combined with at least some features of any one or more of Aspects M1 or M2 to include or use the control circuit configured to determine the dwell time following the first electrosurgical energy pulse based on the determined amount of energy is configured to: compare the determined amount of energy to a stored data set; and determine the dwell time based on the comparison.

Aspect M4 can include or use or can optionally be combined with at least some features of any one or more of Aspects M1 through M3 to include or use the control circuit configured to determine the dwell time following the first electrosurgical energy pulse being configured to: initiate a timer upon delivery of one of the electrosurgical energy pulses; determine that the biological tissue has boiled and stop the timer; compare the timer to one or more values; and determine the dwell time based on the comparison.

Aspect M5 can include or use or can optionally be combined with at least some features of any one or more of Aspects M1 through M4 to include or use the control circuit configured to determine the dwell time following the first electrosurgical energy pulse being configured to: determine an amount of energy delivered to the jaws; determine an electrical characteristic of the tissue; and determine the dwell time following the first electrosurgical energy pulse based on the determined amount of energy and the determined electrical characteristic.

Aspect M6 can include or use or can optionally be combined with at least some features of any one or more of Aspects M1 through M5 to include or use the determined electrical characteristic being impedance.

Aspect M7 can include or use or can optionally be combined with at least some features of any one or more of Aspects M1 through M6 to include or use the determined electrical characteristic being a phase angle.

Aspect M8 can include or use or can optionally be combined with at least some features of any one or more of Aspects M1 through M7 to include or use the control circuit configured to determine the dwell time following the first electrosurgical energy pulse being configured to: determine an amount of current delivered during a previous electrosurgical energy pulse; and determine the dwell time following the first electrosurgical energy pulse based on the determined amount of current.

Aspect M9 can include or use or can optionally be combined with at least some features of any one or more of Aspects M1 through M8 to include or use the control circuit configured to determine the dwell time following the first electrosurgical energy pulse being configured to: determine an amount of charge delivered during a previous electrosurgical energy pulse; and determine the dwell time following the first electrosurgical energy pulse based on the determined amount of charge.

Aspect M10 can include or use or can optionally be combined with at least some features of any one or more of Aspects M1 through M9 to include or use the control circuit configured to determine the dwell time following the first electrosurgical energy pulse being configured to: initiate a timer upon delivery of a current of one of the electrosurgical energy pulses and stop the timer after the current is delivered; compare the timer to one or more values; and determine the dwell time based on the comparison.

N. Pulsing at the End of the Drying Cycle

Aspect N1 can include or use subject matter (e.g., a system, apparatus, method, article, or the like) that can include or use an electrosurgical system for providing an electrotherapeutic signal to a biological tissue, the electrosurgical system comprising: a forceps including: opposable jaw members configured to open and close; and wherein the opposable jaw members, when closed, are configured to clamp the biological tissue therebetween in a manner that provides electrical communication between the opposable jaw members via the clamped biological tissue; and a control circuit in communication with an electrical-energy source, the electrical-energy source electrically coupled to the electrodes and configured to generate the therapeutic signal, the control circuit configured to: cause the electrical-energy source to provide the electrotherapeutic signal to the biological tissue during an electrotherapeutic phase, the electrotherapeutic signal provided according to an electrotherapeutic plan; and cause the electrical-energy source to pulse the electrotherapeutic signal provided to the biological tissue during a sticking reduction phase that follows the electrotherapeutic phase, the electrotherapeutic signal pulsed according to a sticking-reduction plan configured to permit fluid to return to the clamped biological tissue thereby reducing sticking of the biological tissue to the forceps.

Aspect N2 can include or use or can optionally be combined with at least some features of Aspect N1 to include or use a measurement circuit in electrical communication with the opposable jaw members when the electrical-energy source is electrically coupled to the forceps, the measurement circuit configured to measure an electrical parameter of the clamped biological tissue including a reference impedance of the biological tissue, wherein the control circuit is further configured to: determine a therapy time duration based on the measured reference impedance; reduce the electrotherapeutic phase when after determined therapy time duration has expired; and commence the sticking-reduction phase after the therapy time duration has expired.

Aspect N3 can include or use or can optionally be combined with at least some features of any one or more of Aspects N1 or N2 to include or use the reference impedance being measured during an interrogation phase.

Aspect N4 can include or use or can optionally be combined with at least some features of any one or more of Aspects N1 through N3 to include or use the reference impedance being measured during the electrotherapeutic phase.

Aspect N5 can include or use or can optionally be combined with at least some features of any one or more of Aspects N1 through N4 to include or use the sticking-reduction plan has alternating electrical-power minima and maxima, each of the electrical-power minima are below a predetermined threshold.

Aspect N6 can include or use or can optionally be combined with at least some features of any one or more of Aspects N1 through N5 to include or use wherein each of the electrical-power minima of the sticking-reduction plan is maintained for a first predetermined time duration.

Aspect N7 can include or use or can optionally be combined with at least some features of any one or more of Aspects N1 through N6 to include or use the first predetermined time duration being greater than 10 milli-seconds.

Aspect N8 can include or use or can optionally be combined with at least some features of any one or more of Aspects N1 through N7 to include or use each of the electrical-power maxima of the sticking-reduction plan is maintained for a second predetermined time duration.

Aspect N9 can include or use or can optionally be combined with at least some features of any one or more of Aspects N1 through N8 to include or use the second predetermined time duration being greater than 50 milli-seconds.

Aspect N10 can include or use or can optionally be combined with at least some features of any one or more of Aspects N1 through N9 to include or use the sticking-reduction plan being reduced after a third predetermined time duration.

Aspect N11 can include or use or can optionally be combined with at least some features of any one or more of Aspects N1 through N10 to include or use the third predetermined time duration is greater than 200 milli-seconds.

Aspect N12 can include or use or can optionally be combined with at least some features of any one or more of Aspects N1 through N11 to include or use the control circuit configured to pulse the electrotherapeutic signal being configured to pulse the electrotherapeutic signal according to a power-controlled plan.

Aspect N13 can include or use or can optionally be combined with at least some features of any one or more of Aspects N1 through N12 to include or use the control circuit configured to pulse the electrotherapeutic signal is configured to pulse the electrotherapeutic signal according to a voltage-controlled plan.

Aspect N14 can include or use subject matter (e.g., a system, apparatus, method, article, or the like) that can include or use an electrosurgical generator for providing an electrotherapeutic signal to a biological tissue in electrical communication with an electrosurgical instrument, the electrosurgical generator including: an electrical connector configured to electrically couple the electrosurgical instrument to the electrosurgical generator so as to provide electrical communication between the electrosurgical generator and the biological tissue; an electrical-energy source coupled to the electrical connector and configured to generate the electrotherapeutic signal; and a control circuit configured to: cause the electrical-energy source to provide the electrotherapeutic signal to the biological tissue during an electrotherapeutic phase, the electrotherapeutic signal provided according to an electrotherapeutic plan; and cause the electrical-energy source to pulse the electrotherapeutic signal provided to the biological tissue during a sticking reduction phase that follows the electrotherapeutic phase, the electrotherapeutic signal pulsed according to a sticking-reduction plan configured to permit fluid to return to the biological tissue thereby reducing sticking of the biological tissue to the electrosurgical instrument.

Aspect N15 can include or use or can optionally be combined with at least some features of Aspect N14 to include or use a measurement circuit electrically coupled to the electrical connector and configured to measure an electrical parameter of the biological tissue including a reference impedance of the biological tissue, wherein the control circuit is further configured to: determine a therapy time duration based on the measured reference impedance; reduce the electrotherapeutic phase when after determined therapy time duration has expired; and commence the sticking-reduction phase after the therapy time duration has expired.

Aspect N16 can include or use or can optionally be combined with at least some features of any one or more of Aspects N14 or N15 to include or use the sticking-reduction plan has alternating electrical-power minima and maxima, and wherein each of the electrical-power minima of the sticking-reduction plan is maintained for a first predetermined time duration greater than 50 milli-seconds.

Aspect N17 can include or use or can optionally be combined with at least some features of any one or more of Aspects N14 through N16 to include or use wherein each of the electrical-power maxima of the sticking-reduction plan is maintained for a second predetermined time duration greater than 50 milli-seconds.

Aspect N18 can include or use subject matter (e.g., a system, apparatus, method, article, or the like) that can include or use a method for delivering an electrotherapeutic signal to a biological tissue in electrical communication with an electrosurgical instrument, the electrosurgical instrument including a forceps having opposable jaw members, the method including: providing, via an electrical-energy source, the electrotherapeutic signal to the biological tissue during an electrotherapeutic phase, the electrotherapeutic signal provided according to an electrotherapeutic plan; and pulsing, via the electrical-energy source, the electrotherapeutic signal provided to the biological tissue during a sticking reduction phase that follows the electrotherapeutic phase, the electrotherapeutic signal pulsed according to a sticking-reduction plan configured to permit fluid to return to the biological tissue thereby reducing sticking of the biological tissue to the electrosurgical instrument; releasing the biological tissue from the opposable jaw members of the forceps, after the pulsing reduction phase.

Aspect N19 can include or use or can optionally be combined with at least some features of Aspect N18 to include or use measuring, via a measurement circuit, a reference impedance of the biological tissue; determining a therapy time duration based on the measured reference impedance; reducing the electrotherapeutic phase when after determined therapy time duration has expired; and commencing the sticking-reduction phase after the therapy time duration has expired.

O. Terminating a Pulse Based Upon Measurements Taken Within the Pulse

Aspect O1 can include or use subject matter (e.g., a system, apparatus, method, article, or the like) that can include or use a method for delivering an electrotherapeutic signal to biological tissue in electrical communication with an electrosurgical instrument, the method including: measuring a reference impedance of the biological tissue after a time interval following commencement of a therapeutic phase; determining a termination criterion for the therapeutic phase based on the measured reference impedance following commencement of the therapeutic phase; delivering the electrotherapeutic signal to the biological tissue during the therapeutic phase, the delivered electrotherapeutic signal controlled according to an electrotherapeutic plan; and terminating the therapeutic phase in response to the termination criterion being met.

Aspect O2 can include or use or can optionally be combined with at least some features of Aspect O1 to include or use the termination criterion being a temporal criterion.

Aspect O3 can include or use or can optionally be combined with at least some features of any one or more of Aspects O1 or O2 to include or use the termination criterion being an impedance criterion.

Aspect O4 can include or use or can optionally be combined with at least some features of any one or more of Aspects O1 through O3 to include or use wherein determining a termination criterion for the therapeutic phase based on the measured reference impedance following commencement of the therapeutic phase includes: selecting between a temporal criterion and an impedance criterion based on the measured reference impedance.

Aspect O5 can include or use or can optionally be combined with at least some features of any one or more of Aspects O1 through O4 to include or use the delivered electrotherapeutic signal being controlled according to a power-controlled therapeutic plan.

Aspect O6 can include or use or can optionally be combined with at least some features of any one or more of Aspects O1 through O5 to include or use the delivered electrotherapeutic signal being controlled according to a voltage-controlled therapeutic plan.

Aspect O7 can include or use or can optionally be combined with at least some features of any one or more of Aspects O1 through O6 to include or use the therapeutic phase being a desiccation phase.

Aspect O8 can include or use or can optionally be combined with at least some features of any one or more of Aspects O1 through O7 to include or use wherein determining a termination criterion for the electrotherapeutic phase based on the measured reference impedance includes: comparing the measured reference impedance to a threshold impedance value, wherein the threshold impedance value is an absolute impedance value.

Aspect O9 can include or use or can optionally be combined with at least some features of any one or more of Aspects O1 through O8 to include or use wherein determining a termination criterion for the electrotherapeutic phase based on the measured reference impedance includes: comparing the measured reference impedance to a threshold impedance value, wherein the threshold impedance value is a delta impedance value.

Aspect O10 can include or use or can optionally be combined with at least some features of any one or more of Aspects O1 through O9 to include or use the termination criterion being a first termination criterion, wherein the electrotherapeutic signal is a first electrotherapeutic signal, wherein the therapeutic phase is a desiccation phase, and wherein the reference impedance is a first reference impedance, the method comprising: measuring a second reference impedance of the biological tissue following termination of the desiccation phase; determining a second termination criterion for a vessel welding phase based on the measured second reference impedance prior to commencement of the vessel welding phase; delivering a second electrotherapeutic signal to the biological tissue during the vessel welding phase; and terminating the vessel welding phase in response to the second termination criterion being met.

Aspect O11 can include or use or can optionally be combined with at least some features of any one or more of Aspects O1 through O10 to include or use the second termination criterion being a temporal criterion.

Aspect O12 can include or use or can optionally be combined with at least some features of any one or more of Aspects O1 through O11 to include or use the second termination criterion being an impedance criterion.

Aspect O13 can include or use or can optionally be combined with at least some features of any one or more of Aspects O1 through O12 to include or use wherein determining a second termination criterion for a vessel welding phase based on the measured second reference impedance prior to commencement of the vessel welding phase includes: selecting between a temporal criterion and an impedance criterion based on the measured reference impedance.

Notes

Each of the non-limiting aspects or examples described herein may stand on its own, or may be combined in various permutations or combinations with one or more of the other examples.

The above detailed description includes references to the accompanying drawings, which form a part of the detailed description. The drawings show, by way of illustration, specific examples in which the invention may be practiced. These examples are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact discs and digital video discs), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other examples may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples may be combined with each other in various combinations or permutations. The scope of the invention should be determined with reference to the appended claims, along with the full scope of equivalents to which such claims are entitled.

The invention claimed is:

1. An electrosurgical generator configured to generate and provide a therapeutic signal to biological tissue in electrical communication with a surgical instrument, the surgical generator comprising:
a measurement circuit coupled to a control circuit and configured to measure a reference impedance angle of the biological tissue during an interrogation phase; and
the control circuit in communication with an electrical-energy source, the electrical-energy source electrically coupled to the instrument and configured to generate the therapeutic signal, the control circuit configured to:
control delivery of the therapeutic signal provided to the biological tissue;
compare the measured reference impedance angle with an angle threshold; and
in response to the measured reference impedance angle being greater than the angle threshold;
terminate the delivery of the therapeutic signal; and
generate an error notification signal, wherein the error notification indicates a presence of a conductive foreign body in the biological tissue.

2. The electrosurgical generator of claim 1, wherein the measured reference impedance angle is substantially equal to an angular difference between a voltage across and current conducted by the biological tissue as measured by the measurement circuit.

3. The electrosurgical generator of claim 2, wherein the control circuit is configured to:
in response to the measured reference impedance angle being greater than a first angle and less than a second angle, reduce a power level of the therapeutic signal.

4. The electrosurgical generator of claim 3, wherein the first angle is 70 degrees.

5. The electrosurgical generator of claim 2, wherein the control circuit is configured to:
in response to the measured reference impedance angle being less than the angle threshold, reduce or terminate the delivery of the therapeutic signal.

6. The electrosurgical generator of claim 5, wherein the control circuit is configured to generate an error notification signal, wherein the error notification indicates an open circuit.

7. The electrosurgical generator of claim 1, comprising:
a timer to measure an elapsed therapy time, wherein the control circuit is configured to:
compare the elapsed therapy time to a time constant; and
in response to the elapsed therapy time exceeding the time constant, the measurement circuit is configured to measure the reference impedance angle of the biological tissue.

8. The electrosurgical generator of claim 1, wherein the angle threshold is greater than 70 degrees.

9. An electrosurgical generator configured to generate and provide a therapeutic signal to biological tissue in electrical communication with a surgical instrument, the surgical generator comprising:
a measurement circuit coupled to a control circuit and configured to measure a reference impedance angle of the biological tissue during an interrogation phase; and
the control circuit in communication with an electrical-energy source, the electrical-energy source electrically coupled to the instrument and configured to generate the therapeutic signal, the control circuit configured to:
control delivery of the therapeutic signal provided to the biological tissue;
compare the measured reference impedance angle with an angle threshold;
determine a presence of a conductive foreign body in the biological tissue based on the comparison; and
terminate the delivery of the therapeutic signal.

10. The electrosurgical generator of claim 9, wherein the measured reference impedance angle is substantially equal to an angular difference between a voltage across and current conducted by the biological tissue as measured by the measurement circuit.

11. The electrosurgical generator of claim 9, wherein the control circuit is configured to:
generate an error notification signal in response to the measured reference impedance angle being greater than the angle threshold, wherein the error notification indicates the presence of the conductive foreign body in the biological tissue.

12. The electrosurgical generator of claim 9, wherein the conductive foreign body is selected from the group consisting of: a surgical tool, metal clip, and staple.

13. The electrosurgical generator of claim 9, wherein the control circuit is configured to:
in response to the measured reference impedance angle being greater than a first angle and less than a second angle, reduce a power level of the therapeutic signal.

14. The electrosurgical generator of claim 13, wherein the first angle is 70 degrees.

15. The electrosurgical generator of claim 9, wherein the angle threshold is greater than 70 degrees.

16. The electrosurgical generator of claim 9, comprising:
a tinier to measure an elapsed therapy time, wherein the control circuit is configured to:
compare the elapsed therapy time to a time constant; and
in response to the elapsed therapy time exceeding the time constant, the measurement circuit is configured to measure the reference impedance angle of the biological tissue.

17. A method of operating an electrosurgical generator, wherein the electrosurgical generator is configured to generate and provide a therapeutic signal to biological tissue in electrical communication with a surgical instrument, the method comprising:
  measuring a reference impedance angle of the biological tissue during an interrogation phase;
  controlling delivery of the therapeutic signal provided to the biological tissue;
  comparing the measured reference impedance angle with an angle threshold; and
  in response to the measured reference impedance angle being greater than the angle threshold;
    terminate the delivery of the therapeutic signal; and
    generate an error notification signal, wherein the error notification indicates a presence of a conductive foreign body in the biological tissue.

* * * * *